(12) United States Patent
Edmonds et al.

(10) Patent No.: US 11,471,458 B2
(45) Date of Patent: *Oct. 18, 2022

(54) DIACYLGLYCEROL ACYL TRANSFERASE 2 INHIBITOR

(71) Applicant: Pfizer Inc., New York, NY (US)

(72) Inventors: David James Edmonds, Arlington, MA (US); Kevin James Filipski, Reading, MA (US); Kentaro Futatsugi, Sharon, MA (US); Michelle Renee Garnsey, Medford, MA (US); Jack Chang Hung Lee, Mystic, CT (US); Daniel Jonathan Smaltz, Cambridge, MA (US)

(73) Assignee: Pfizer Inc., New York, NY (US)

( * ) Notice: Subject to any disclaimer, the term of this patent is extended or adjusted under 35 U.S.C. 154(b) by 185 days.

This patent is subject to a terminal disclaimer.

(21) Appl. No.: 17/062,982

(22) Filed: Oct. 5, 2020

(65) Prior Publication Data

US 2021/0100796 A1 Apr. 8, 2021

Related U.S. Application Data

(60) Provisional application No. 63/074,123, filed on Sep. 3, 2020, provisional application No. 62/911,094, filed on Oct. 4, 2019.

(51) Int. Cl.
| | | |
|---|---|---|
| *A61K 31/506* | (2006.01) | |
| *A61P 3/06* | (2006.01) | |
| *A61K 31/155* | (2006.01) | |
| *A61K 31/4545* | (2006.01) | |
| *C07D 401/14* | (2006.01) | |
| *A61K 31/4985* | (2006.01) | |
| *A61K 31/7048* | (2006.01) | |
| *A61K 45/06* | (2006.01) | |

(52) U.S. Cl.
CPC ........ *A61K 31/506* (2013.01); *A61K 31/155* (2013.01); *A61K 31/4545* (2013.01); *A61K 31/4985* (2013.01); *A61K 31/7048* (2013.01); *A61K 45/06* (2013.01); *A61P 3/06* (2018.01); *C07D 401/14* (2013.01)

(58) Field of Classification Search
CPC ............. A61K 31/506; A61K 31/155; A61K 31/4545; A61P 3/06
See application file for complete search history.

(56) References Cited

U.S. PATENT DOCUMENTS 10,071,992 B2  9/2018  Boehm et al.
2015/0259323 A1  9/2015  Cabral et al.

FOREIGN PATENT DOCUMENTS

| WO | 2013137628 | 9/2013 |
| WO | 2013150416 | 10/2013 |
| WO | 2015077299 | 5/2015 |
| WO | 2016036633 | 3/2016 |
| WO | 2016036636 | 3/2016 |
| WO | 2016036638 | 3/2016 |
| WO | 2018033832 | 2/2018 |

OTHER PUBLICATIONS

Choi, C.S., et al., "Suppression of Diacylglycerol Acyltransferase-2 (DGAT2), but not DGAT1, with Antisense Oligonucleotides Reverses Diet-induced Hepatic Steatosis and Insulin Resistance", Journal of Biological Chemistry, Aug. 3, 2007, pp. 22678-22688, 282(31).
International Written Opinion and Search Report dated Nov. 25, 2020 for Application No. PCT/IB2020/059145, filed on Sep. 30, 2020, 12 pages.

*Primary Examiner* — Yong S. Chong
(74) *Attorney, Agent, or Firm* — Lisa A. Samuels

(57) ABSTRACT

Described herein are compounds of Formula (I)

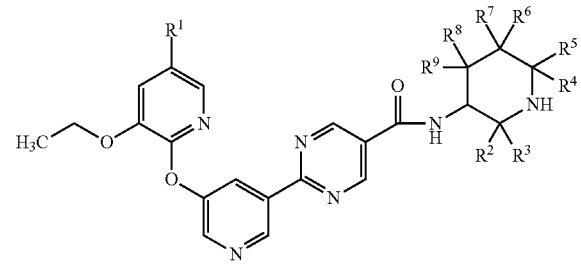

wherein $R^1$, $R^2$, $R^3$, $R^4$, $R^5$, $R^6$, $R^7$, $R^8$ and $R^9$ are defined herein, their use as diacylglycerol acyltransferase 2 (DGAT2) inhibitors, pharmaceutical compositions containing such inhibitors and the use of such inhibitors to treat, for example, NASH.

17 Claims, 8 Drawing Sheets

DIACYLGLYCEROL ACYL TRANSFERASE 2 INHIBITOR

This application is a Non-Provisional application under 35 U.S.C. 119(e) which claims the benefit of U.S. Provisional Patent Application No. 63/073,123, filed on Sep. 3, 2020 and U.S. Provisional Patent Application No. 62,911,094, filed on Oct. 4, 2019.

FIELD OF THE INVENTION

The present invention relates to new pharmaceutical compounds, pharmaceutical compositions containing the compounds, and use of the compounds to inhibit the activity of the diacylglycerol acyltransferase 2 (DGAT2).

BACKGROUND OF THE INVENTION

Diacylglycerol acyltransferases (DGAT) catalyze the terminal step in triacylglyceride (TAG) synthesis, specifically, the esterification of a fatty acid with diacylglycerol resulting in the formation of TAG. In mammals, two DGAT enzymes (DGAT1 and DGAT2) have been characterized. Although these enzymes catalyze the same enzymatic reaction their respective amino acid sequences are unrelated and they occupy distinct gene families. DGAT2 is highly expressed in liver and adipose, and unlike DGAT1, exhibits exquisite substrate specificity for diacylglyceride (DAG). Deletion of the DGAT2 gene in rodents results in defective intrauterine growth, severe lipemia, impaired skin barrier function, and early post-natal death. It is clear that suppression of DGAT2 results in a down-regulation of the expression of multiple genes encoding proteins involved in lipogensis, including sterol regulatory element-binding proteins 1c (SREBP1c) and stearoyl CoA-desaturase 1 (SCD1). In parallel, oxidative pathways are induced as evidenced by increased expression of genes such as carnitine palmitoyl transfersase 1 (CPT1). The net result of these changes is to decrease the levels of hepatic DAG and TAG lipid which, in turn, leads to improved insulin responsiveness in the liver. Furthermore, DGAT2 inhibition suppresses hepatic VLDL TAG secretion and leads to reduction in circulating cholesterol levels. Finally, plasma apolipoprotein B (APOB) levels are suppressed, possibly due to decreased supply of TAG for lipidation of the newly synthesized APOB protein. The beneficial effects of DGAT2 inhibition on both glycemic control and plasma cholesterol profile suggest that this target is valuable in the treatment of metabolic disease (Choi, C. S. et. al. 2007. *J Biol Chem* 282: 22678-22688).

In addition, the observation that suppression of DGAT2 activity results in reduced hepatic lipid accumulation suggests that inhibitors of this enzyme might have utility in the treatment of non-alcoholic steatohepatitis (NASH), a highly prevalent liver disease characterized by the deposition of excess fat in the liver.

In recent years, several small molecule inhbitors of DGAT2 have been reported in the literature and patent applications (WO2013150416, WO2013137628, US20150259323, WO2015077299, WO2016036633, WO2016036638, WO2016036636). Recently, commonly assigned PCT application PCT/IB2017/054862 was published as WO2018/033832 on Feb. 22, 2018 disclosing small molecule inhibitors of DGAT2.

Nevertheless, there remains a need for pharmaceutical agents that have DGAT2 inhibiting activity and are useful in the treatment, prevention or diminution of the manifestations of the maladies described herein. Moreover, there remains a need for DGAT2 inhibitors having improved pharmacokinetic properties such as solubility, clearance and half life. A longer half life in humans may result from lower clearance and/or increased volume of distribution.

SUMMARY OF THE INVENTION

The present application is directed to compounds of Formula (I)

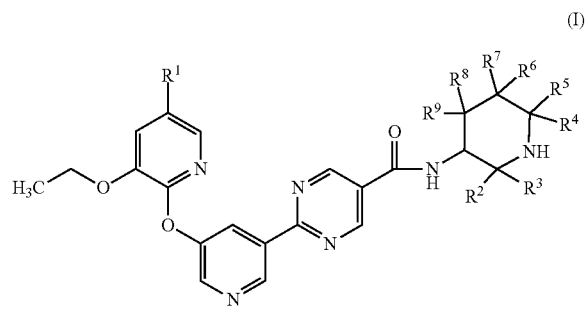

wherein
$R^1$ is H or fluoro;
$R^2$, $R^3$, $R^4$ and $R^5$ are each independently selected from H, $(C_1-C_3)$alkyl, $(C_1-C_3)$fluoroalkyl, $(C_1-C_3)$hydroxyalkyl, and $-(C_1-C_3)$alkyl-$(C_1-C_2)$alkoxy, and
$R^6$, $R^7$, $R^8$, and $R^9$ are each independently selected from H, fluoro, hydroxyl, $(C_1-C_3)$alkyl, $(C_1-C_3)$fluoroalkyl, $(C_1-C_3)$hydroxyalkyl, $(C_1-C_2)$alkoxy, $C_2)$fluoroalkoxy, and $-(C_1-C_3)$alkyl-$(C_1-C_2)$alkoxy, and
wherein 0, 1 or 2 of $R^2$, $R^3$, $R^4$, $R^5$, $R^6$, $R^7$, $R^8$, and $R^9$ are other than H;
or a pharmaceutically acceptable salt thereof.

The present invention is also directed at methods of treating fatty liver, nonalcoholic fatty liver disease, nonalcoholic steatohepatitis, nonalcoholic steatohepatitis with liver fibrosis, nonalcoholic steatohepatitis with cirrhosis or nonalcoholic steatohepatitis with cirrhosis and hepatocellular carcinoma including administering to a mammal, such as a human, in need of such treatment a therapeutically effective amount of a compound of Formula (I) or (II) or a pharmaceutically acceptable salt of said compound.

The present invention is also directed at methods of treating heart failure, congestive heart failure, coronary heart disease, peripheral vascular disease, renovascular disease, pulmonary hypertension, vasculitis, acute coronary syndromes and modification of cardiovascular risk including administering to a mammal, such as a human, in need of such treatment a therapeutically effective amount of a compound of Formula (I) or (II) or a pharmaceutically acceptable salt of said compound.

The present invention is also directed at methods of treating Type I diabetes, Type II diabetes mellitus, idiopathic Type I diabetes (Type Ib), latent autoimmune diabetes in adults (LADA), early-onset Type 2 diabetes (EOD), youth-onset atypical diabetes (YOAD), maturity onset diabetes of the young (MODY), malnutrition-related diabetes, gestational diabetes, coronary heart disease, ischemic stroke, restenosis after angioplasty, peripheral vascular disease, intermittent claudication, myocardial infarction, dyslipidemia, post-prandial lipemia, conditions of impaired glucose tolerance (IGT), conditions of impaired fasting plasma glucose, metabolic acidosis, ketosis, arthritis, diabetic retinopathy, macular degeneration, cataract, diabetic nephropathy, glomerulosclerosis, chronic renal failure, diabetic neuropathy, metabolic syndrome, syndrome X, hyperglycemia, hyperinsulinemia, hypertriglyceridemia, insulin resistance, impaired glucose metabolism, skin and connective tissue disorders, foot ulcerations and ulcerative colitis, endothelial dysfunction and impaired vascular compliance, hyper apo B lipoproteinemia, and maple syrup urine disease including administering to a mammal, such as a human, in need of such treatment a therapeutically effective amount of a compound of Formula (I) or (II) or a pharmaceutically acceptable salt of said compound.

The present invention is also directed at a method of treating hepatocellular carcinoma, kidney renal clear cell carcinoma, head and neck squamous cell carcinoma, colorectal adenocarcinoma, mesothelioma, stomach adenocarcinoma, adrenocortical carcinoma, kidney papillary cell carcinoma, cervical and endocervical carcinoma, bladder urothelial carcinoma, or lung adenocarcinoma comprising administering to a mammal, such as a human, in need of such treatment a therapeutically effective amount of a compound of Formula (I) or (II) or a pharmaceutically acceptable salt of said compound.

The present invention is also directed at a method for the reduction of at least one or two points in severity of nonalcoholic fatty liver disease (NAFLD) Activity Score (NAS) from baseline comprising the step of measuring the baseline NAS in a human, administering to said human an effective amount of a compound of Formula (I) or (II) or a pharmaceutically acceptable salt of said compound, and measuring the NAS of said human.

The present invention is also directed at pharmaceutical compositions having a therapeutically effective amount of a compound of Formula (I) or (II) or a pharmaceutically acceptable salt of said compound and a pharmaceutically acceptable carrier, vehicle or diluent.

The present invention is also directed at pharmaceutical combination compositions that include: a therapeutically effective amount of a composition having:

a first compound, said first compound being a compound of Formula (I) or (II) or a pharmaceutically acceptable salt of said compound;

a second compound, said second compound being an anti-diabetic agent; a non-alcoholic steatohepatitis treatment agent, a non-alcoholic fatty liver disease treatment agent or an anti-heart failure treatment agent and a pharmaceutical carrier, vehicle or diluent.

It is to be understood that both the foregoing general description and the following detailed description are exemplary and explanatory only and are not restrictive of the invention, as claimed.

DETAILED DESCRIPTION OF THE INVENTION

Figure 1:
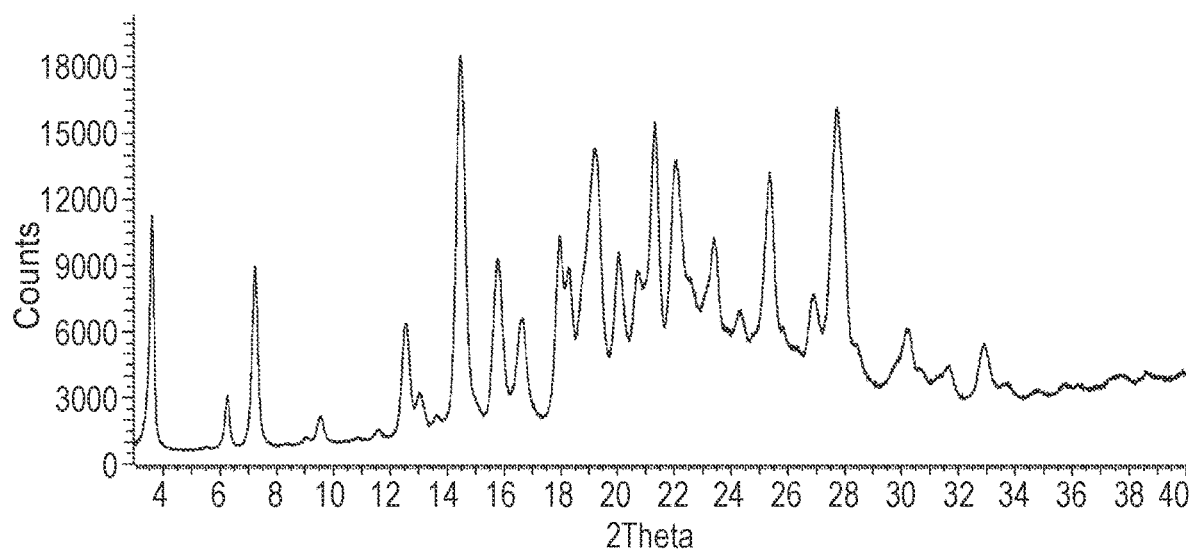
FIG. 1 is a characteristic x-ray powder diffraction pattern showing Example 4, Form 1 (Vertical Axis: Intensity (CPS); Horizontal Axis: Two theta (degrees)).

The present invention may be understood more readily by reference to the following detailed description of exemplary embodiments of the invention and the examples included therein.

It is to be understood that this invention is not limited to specific synthetic methods of making that may of course vary. It is also to be understood that the terminology used herein is for the purpose of describing particular embodiments only and is not intended to be limiting. In this specification and in the claims that follow, reference will be made to a number of terms that shall be defined to have the following meanings:

As used herein in the specification, "a" or "an" may mean one or more. As used herein in the claim(s), when used in conjunction with the word "comprising", the words "a" or "an" may mean one or more than one. As used herein "another" may mean at least a second or more.

The term "about" refers to a relative term denoting an approximation of plus or minus 10% of the nominal value it refers, in one embodiment, to plus or minus 5%, in another embodiment, to plus or minus 2%. For the field of this disclosure, this level of approximation is appropriate unless the value is specifically stated to require a tighter range.

"Compounds" when used herein includes any pharmaceutically acceptable derivative or variation, including conformational isomers (e.g., cis and trans isomers) and all optical isomers (e.g., enantiomers and diastereomers), racemic, diastereomeric and other mixtures of such isomers, as well as solvates, hydrates, isomorphs, polymorphs, tautomers, esters, salt forms, and prodrugs. The expression "prodrug" refers to compounds that are drug precursors which following administration, release the drug in vivo via some chemical or physiological process (e.g., a prodrug on being brought to the physiological pH or through enzyme action is converted to the desired drug form).

The term "alkyl", alone or in combination, means an acyclic, saturated hydrocarbon group of the formula $C_nH_{2n+1}$ which may be linear or branched. Examples of such groups include, but are not limited to, methyl, ethyl, n-propyl, isopropyl, butyl, sec-butyl, isobutyl and t-butyl. The carbon atom content of alkyl and various other hydrocarbon-containing moieties is indicated by a prefix designating a lower and upper number of carbon atoms in the moiety, that is, the prefix Ci-Cj indicates a moiety of the integer "i" to the integer "j" carbon atoms, inclusive. Thus, for example, $C_1$-$C_3$ alkyl refers to alkyl of one to three carbon atoms, inclusive.

"Fluoroalkyl" means an alkyl as defined herein substituted with one, two or three fluoro atoms. Exemplary $(C_1)$fluoroalkyl compounds include fluoromethyl, difluoromethyl and trifluoromethyl; exemplary $(C_2)$fluoroalkyl compounds include 1-fluoroethyl, 2-fluoroethyl, 1,1-difluoroethyl, 1,2-difluoroethyl, 1,1,1-trifluoroethyl, 1,1,2-trifluoroethyl, and the like.

"Hydroxyalkyl" means an alkyl as defined herein substituted with one atoms. Exemplary hydroxyalkyl compounds include hydroxymethyl, 1-hydroxyethyl, 2-hydroxyethyl, and the like.

By "alkoxy" is meant straight chain saturated alkyl or branched chain saturated alkyl bonded through an oxy. Exemplary of such alkoxy groups (assuming the designated length encompasses the particular example) are methoxy, ethoxy, propoxy, isopropoxy, butoxy, isobutoxy, tertiary butoxy, pentoxy, isopentoxy, neopentoxy, tertiary pentoxy, hexoxy, isohexoxy, heptoxy and octoxy.

By "fluoroalkoxy" means an alkoxy as defined herein substituted with one, two or three fluoro atoms. Exemplary $(C_1)$fluoroalkoxy compounds include fluoromethoxy, difluoromethoxy and trifluoromethoxy; exemplary $(C_2)$fluoroalkyl compounds include 1-fluoroethoxy, 2-fluoroethoxy, 1,1-difluoroethoxy, 1,2-difluoroethoxy, 1,1,1-trifluoroethoxy, 1,1,2-trifluoroethoxy, and the like.

"Patient" refers to warm blooded animals such as, for example, guinea pigs, mice, rats, gerbils, cats, rabbits, dogs, cattle, goats, sheep, horses, monkeys, chimpanzees, and humans.

The term "pharmaceutically acceptable" means the substance (e.g., the compounds of the invention) and any salt thereof, or composition containing the substance or salt of the invention that is suitable for administration to a patient.

As used herein, the expressions "reaction-inert solvent" and "inert solvent" refer to a solvent or a mixture thereof which does not interact with starting materials, reagents, intermediates or products in a manner which adversely affects the yield of the desired product.

As used herein, the term "selectivity" or "selective" refers to a greater effect of a compound in a first assay, compared to the effect of the same compound in a second assay. For example, in "gut selective" compounds, the first assay is for the half life of the compound in the intestine and the second assay is for the half life of the compound in the liver.

"Therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "treating", "treat" or "treatment" as used herein embraces both preventative, i.e., prophylactic, and palliative treatment, i.e., relieve, alleviate, or slow the progression of the patient's disease (or condition) or any tissue damage associated with the disease.

The present application is further directed to compounds of Formula (II)

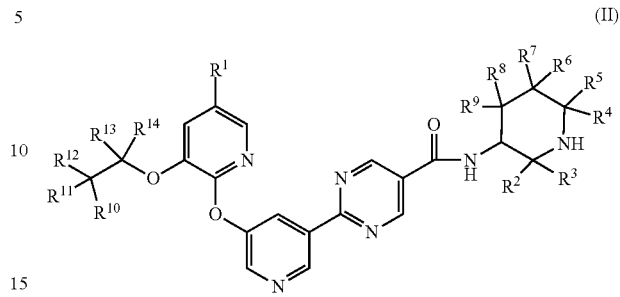

(II)

wherein:

$R^1$ is H or fluoro;

$R^2$, $R^3$, $R^4$ and $R^5$ are each independently selected from H, $(C_1$-$C_3)$alkyl, $(C_1$-$C_3)$fluoroalkyl, $(C_1$-$C_3)$hydroxyalkyl, and —$(C_1$-$C_3)$alkyl-$(C_1$-$C_2)$alkoxy;

$R^6$, $R^7$, $R^8$, and $R^9$ are each independently selected from H, fluoro, hydroxyl, $(C_1$-$C_3)$alkyl, $(C_1$-$C_3)$fluoroalkyl, $(C_1$-$C_3)$hydroxyalkyl, $(C_1$-$C_2)$alkoxy, $(C_1$-$C_2)$fluoroalkoxy, and —$(C_1$-$C_3)$alkyl-$(C_1$-$C_2)$alkoxy, and $R^{10}$, $R^{11}$, $R^{12}$, $R^{13}$ and $R^{14}$ are each independently selected from H and deuterium; and wherein 0, 1 or 2 of $R^2$, $R^3$, $R^4$, $R^5$, $R^6$, $R^7$, $R^8$, and $R^9$ are other than H;

or a pharmaceutically acceptable salt thereof.

One embodiment of the present invention includes compounds of Formula (I) or (II) wherein $R^2$, $R^3$, $R^4$ and $R^5$ are each independently selected from H and $(C_1)$fluoroalkyl and $R^6$, $R^7$, $R^8$, and $R^9$ are each independently selected from H, $(C_1)$fluoroalkyl, and fluoro; wherein 0, 1 or 2 of $R^2$, $R^3$, $R^4$, $R^5$, $R^6$, $R^7$, $R^8$, and $R^9$ are other than H; or a pharmaceutically acceptable salt thereof.

Another embodiment of the present invention includes compounds of Formula (I) or (II) wherein $R^2$, $R^3$, $R^4$, $R^5$, $R^6$, and $R^7$ are H; and $R^8$ and $R^9$ are independently selected from H, $(C_1)$fluoroalkyl and fluoro; wherein at least one of $R^8$, and $R^9$ are $(C_1)$fluoroalkyl or fluoro; or a pharmaceutically acceptable salt thereof.

Another embodiment of the present invention includes compounds of Formula (I) or (II) wherein $R^2$, $R^3$, $R^4$, $R^5$, $R^8$, and $R^9$ are H; and $R^6$ and $R^7$ are each independently selected from H, $(C_1)$fluoroalkyl and fluoro wherein at least one of $R^6$ and $R^7$ are $(C_1)$fluoroalkyl or fluoro; or a pharmaceutically acceptable salt thereof.

Another embodiment of the present invention includes compounds of Formula (I) or (II) wherein $R^2$, $R^3$, $R^4$, $R^5$, $R^6$, and $R^9$ are H; and $R^7$ and $R^8$ are each independently selected from H, $(C_1)$fluoroalkyl and fluoro wherein at least one of $R^7$ and $R^8$ are $(C_1)$fluoroalkyl or fluoro; or a pharmaceutically acceptable salt thereof.

Another embodiment of the present invention includes compounds of Formula (I) or (II) wherein $R^2$, $R^3$, $R^4$, $R^5$, $R^6$, $R^8$ and $R^9$ are H; and $R^7$ is $(C_1)$fluoroalkyl or fluoro; or a pharmaceutically acceptable salt thereof.

Another embodiment of the present invention includes compounds of Formula (I) or (II) wherein $R^2$, $R^3$, $R^4$, $R^5$, $R^6$, $R^8$ and $R^9$ are H; and $R^7$ is fluoro; or a pharmaceutically acceptable salt thereof.

Another embodiment of the present invention includes a compound selected from
2-(5-((3-ethoxy-5-fluoropyridin-2-yl)oxy)pyridin-3-yl)-N-((3R,4S)-4-fluoropiperidin-3-yl)pyrimidine-5-carboxamide;
2-(5-((3-ethoxy-5-fluoropyridin-2-yl)oxy)pyridin-3-yl)-N-((3S,5S)-5-fluoropiperidin-3-yl)pyrimidine-5-carboxamide;
2-(5-((3-ethoxypyridin-2-yl)oxy)pyridin-3-yl)-N-((3R,4S)-4-fluoropiperidin-3-yl)pyrimidine-5-carboxamide;
2-(5-((3-ethoxypyridin-2-yl)oxy)pyridin-3-yl)-N-((3R,4R)-4-fluoropiperidin-3-yl)pyrimidine-5-carboxamide;
2-(5-((3-ethoxy-5-fluoropyridin-2-yl)oxy)pyridin-3-yl)-N-((3R,4R)-4-fluoropiperidin-3-yl)pyrimidine-5-carboxamide; and
2-(5-((3-ethoxypyridin-2-yl)oxy)pyridin-3-yl)-N-((3S,5S)-5-fluoropiperidin-3-yl)pyrimidine-5-carboxamide,
or a pharmaceutically acceptable salt thereof;

Another embodiment includes a compound having the structure:

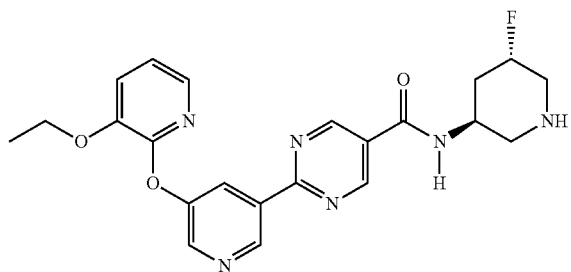 [SMILES: CCOc1cccnc1Oc1cncc(-c2ncc(C(=O)N[C@@H]3CNC[C@@H](F)C3)cn2)c1]

or a pharmaceutically acceptable salt thereof and crystals including said compound or pharmaceutically acceptable salt thereof.

In another embodiment, the compound is 2-(5-((3-ethoxypyridin-2-yl)oxy)pyridin-3-yl)-N-(5-fluoropiperidin-3-yl)pyrimidine-5-carboxamide.

Every Example or pharmaceutically acceptable salt thereof may be claimed individually or grouped together in any combination with any number of each and every embodiment described herein.

Another embodiment of the present invention includes use of a compound of Formula (I) or (II) or a pharmaceutically acceptable salt of said compound for use as a medicament, particularly wherein said medicament is for use in the treatment of fatty liver, nonalcoholic fatty liver disease, nonalcoholic steatohepatitis, nonalcoholic steatohepatitis with liver fibrosis, nonalcoholic steatohepatitis with cirrhosis or nonalcoholic steatohepatitis with cirrhosis and hepatocellular carcinoma including administering to a mammal, such as a human, in need of such treatment a therapeutically effective amount.

Another embodiment of the present invention includes use of a compound of Formula (I) or (II) or a pharmaceutically acceptable salt of said compound for the manufacture of a medicament in treating fatty liver, nonalcoholic fatty liver disease, nonalcoholic steatohepatitis, nonalcoholic steatohepatitis with liver fibrosis, nonalcoholic steatohepatitis with cirrhosis or nonalcoholic steatohepatitis with cirrhosis and hepatocellular carcinoma including administering to a mammal, such as a human, in need of such treatment a therapeutically effective amount.

Another embodiment of the present invention includes use of a compound of Formula (I) or (II) or a pharmaceutically acceptable salt of said compound for use as a medicament, particularly wherein said medicament is for use in the treatment of heart failure, congestive heart failure, coronary heart disease, peripheral vascular disease, renovascular disease, pulmonary hypertension, vasculitis, acute coronary syndromes and modification of cardiovascular risk including administering to a mammal, such as a human, in need of such treatment a therapeutically effective amount of a compound of Formula (I) or (II) or a pharmaceutically acceptable salt of said compound.

Another embodiment of the present invention includes use of a compound of Formula (I) or (II) or a pharmaceutically acceptable salt of said compound for the manufacture of a medicament in treating heart failure, congestive heart failure, coronary heart disease, peripheral vascular disease, renovascular disease, pulmonary hypertension, vasculitis, acute coronary syndromes and modification of cardiovascular risk including administering to a mammal, such as a human, in need of such treatment a therapeutically effective amount of a compound of Formula (I) or (II) or a pharmaceutically acceptable salt of said compound.

Another embodiment of the present invention includes use of a compound of Formula (I) or (II) or a pharmaceutically acceptable salt of said compound for use as a medicament, particularly wherein said medicament is for use in the treatment of Type I diabetes, Type II diabetes mellitus, idiopathic Type I diabetes (Type Ib), latent autoimmune diabetes in adults (LADA), early-onset Type 2 diabetes (EOD), youth-onset atypical diabetes (YOAD), maturity onset diabetes of the young (MODY), malnutrition-related diabetes, gestational diabetes, coronary heart disease, ischemic stroke, restenosis after angioplasty, peripheral vascular disease, intermittent claudication, myocardial infarction, dyslipidemia, post-prandial lipemia, conditions of impaired glucose tolerance (IGT), conditions of impaired fasting plasma glucose, metabolic acidosis, ketosis, arthritis, diabetic retinopathy, macular degeneration, cataract, diabetic nephropathy, glomerulosclerosis, chronic renal failure, diabetic neuropathy, metabolic syndrome, syndrome X, hyperglycemia, hyperinsulinemia, hypertriglyceridemia, insulin resistance, impaired glucose metabolism, skin and connective tissue disorders, foot ulcerations and ulcerative colitis, endothelial dysfunction and impaired vascular compliance, hyper apo B lipoproteinemia, and maple syrup urine disease including administering to a mammal, such as a human, in need of such treatment a therapeutically effective amount of a compound of Formula (I) or (II) or a pharmaceutically acceptable salt of said compound.

Another embodiment of the present invention includes use of a compound of Formula (I) or (II) or a pharmaceutically acceptable salt of said compound for the manufacture of a medicament in treating Type I diabetes, Type II diabetes mellitus, idiopathic Type I diabetes (Type Ib), latent autoimmune diabetes in adults (LADA), early-onset Type 2 diabetes (EOD), youth-onset atypical diabetes (YOAD), maturity onset diabetes of the young (MODY), malnutrition-related diabetes, gestational diabetes, coronary heart disease, ischemic stroke, restenosis after angioplasty, peripheral vascular disease, intermittent claudication, myocardial infarction, dyslipidemia, post-prandial lipemia, conditions of impaired glucose tolerance (IGT), conditions of impaired fasting plasma glucose, metabolic acidosis, ketosis, arthritis, diabetic retinopathy, macular degeneration, cataract, diabetic nephropathy, glomerulosclerosis, chronic renal failure, diabetic neuropathy, metabolic syndrome, syndrome X, hyperglycemia, hyperinsulinemia, hypertriglyceridemia, insulin resistance, impaired glucose metabolism, skin and connective tissue disorders, foot ulcerations and ulcerative colitis, endothelial dysfunction and impaired vascular compliance, hyper apo B lipoproteinemia, and maple syrup urine disease including administering to a mammal, such as a human, in need of such treatment a therapeutically effective amount of a compound of Formula (I) or (II) or a pharmaceutically acceptable salt of said compound.

Another embodiment of the present invention includes use of a compound of Formula (I) or (II) or a pharmaceutically acceptable salt of said compound for use as a medicament, particularly wherein said medicament is for use in the treatment of hepatocellular carcinoma, kidney renal clear cell carcinoma, head and neck squamous cell carcinoma, colorectal adenocarcinoma, mesothelioma, stomach adenocarcinoma, adrenocortical carcinoma, kidney papillary cell carcinoma, cervical and endocervical carcinoma, bladder urothelial carcinoma, or lung adenocarcinoma comprising administering to a mammal, such as a human, in need of such treatment a therapeutically effective amount of a compound of Formula (I) or (II) or a pharmaceutically acceptable salt of said compound.

Another embodiment of the present invention includes use of a compound of Formula (I) or (II) or a pharmaceutically acceptable salt of said compound for the manufacture of a medicament in treating hepatocellular carcinoma, kidney renal clear cell carcinoma, head and neck squamous cell carcinoma, colorectal adenocarcinoma, mesothelioma, stomach adenocarcinoma, adrenocortical carcinoma, kidney papillary cell carcinoma, cervical and endocervical carcinoma, bladder urothelial carcinoma, or lung adenocarcinoma comprising administering to a mammal, such as a human, in need of such treatment a therapeutically effective amount of a compound of Formula (I) or (II) or a pharmaceutically acceptable salt of said compound.

The compounds of the present invention may contain asymmetric or chiral centers, and, therefore, exist in different stereoisomeric forms. Unless specified otherwise, it is intended that all stereoisomeric forms of the compounds of the present invention as well as mixtures thereof, including racemic mixtures, form part of the present invention. In addition, the present invention embraces all geometric and positional isomers. For example, if a compound of the present invention incorporates a double bond or a fused ring, both the cis- and trans-forms, as well as mixtures, are embraced within the scope of the invention.

Chiral compounds of the invention (and chiral precursors thereof) may be obtained in enantiomerically-enriched form using chromatography, typically high pressure liquid chromatography (HPLC) or supercritical fluid chromatography (SFC), on a resin with an asymmetric stationary phase and with a mobile phase consisting of a hydrocarbon, typically heptane or hexane, containing from 0 to 50% isopropanol, typically from 2 to 20%, and from 0 to 5% of an alkylamine, typically 0.1% diethylamine (DEA) or isopropylamine. Concentration of the eluent affords the enriched mixture. In the case where SFC is used, the mobile phase may consist of a supercritical fluid, typically carbon dioxide, containing 2-50% of an alcohol, such as methanol, ethanol or isopropanol.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereoisomers and converting (e.g. hydrolyzing) the individual diastereoisomers to the corresponding pure enantiomers. Enantiomers can also be separated by use of a chiral HPLC column. Alternatively, the specific stereoisomers may be synthesized by using an optically active starting material, by asymmetric synthesis using optically active reagents, substrates, catalysts or solvents, or by converting one stereoisomer into the other by asymmetric transformation.

Where the compounds of the present invention possess two or more stereogenic centers and the absolute or relative stereochemistry is given in the name, the designations R and S refer respectively to each stereogenic center in ascending numerical order (1, 2, 3, etc.) according to the conventional IUPAC number schemes for each molecule. Where the compounds of the present invention possess one or more stereogenic centers and no stereochemistry is given in the name or structure, it is understood that the name or structure is intended to encompass all forms of the compound, including the racemic form.

The compounds of this invention may contain olefin-like double bonds. When such bonds are present, the compounds of the invention exist as cis and trans configurations and as mixtures thereof. The term "cis" refers to the orientation of two substituents with reference to each other and the plane of the ring (either both "up" or both "down"). Analogously, the term "trans" refers to the orientation of two substituents with reference to each other and the plane of the ring (the substituents being on opposite sides of the ring).

It is also possible that the intermediates and compounds of the present invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations.

Valence tautomers include interconversions by reorganization of some of the bonding electrons.

Included within the scope of the claimed compounds present invention are all stereoisomers, geometric isomers and tautomeric forms of the compounds of Formula (I) or (II), including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

The present invention includes all pharmaceutically acceptable isotopically-labelled compounds of Formula (I) or (II) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$, $^{124}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of Formula (I) or (II), for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Tomography (PET) studies for examining substrate receptor occupancy.

Isotopically-labelled compounds of Formula (I) or (II) can generally be prepared by conventional techniques known to those skilled in the art or by processes analogous to those described in the accompanying Examples and Preparations using an appropriate isotopically-labelled reagents in place of the non-labelled reagent previously employed.

The compounds of the present invention may be isolated and used per se, or when possible, in the form of its pharmaceutically acceptable salt. The term "salts" refers to inorganic and organic salts of a compound of the present invention. These salts can be prepared in situ during the final isolation and purification of a compound, or by separately treating the compound with a suitable organic or inorganic acid and isolating the salt thus formed.

Salts encompassed within the term "pharmaceutically acceptable salts" refer to the compounds of this invention which are generally prepared by reacting the free base with a suitable organic or inorganic acid to provide a salt of the compound of the invention that is suitable for administration to a patient. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. See e.g. Berge, et al. *J. Pharm. Sci.* 66, 1-19 (1977); *Handbook of Pharmaceutical Salts: Properties, Selection, and Use* by Stahl and Wermuth (Wiley-VCH, 2002).

The compounds of Formula (I) or (II), and pharmaceutically acceptable salts thereof, may exist in unsolvated and solvated forms. The term 'solvate' is used herein to describe a molecular complex comprising the compound of Formula (I) or (II), or a pharmaceutically acceptable salt thereof, and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see Polymorphism in Pharmaceutical Solids by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex may have a well-defined stoichiometry independent of humidity. When, however, the solvent or water is weakly bound, as in channel solvates and hygroscopic compounds, the water/solvent content may be dependent on humidity and drying conditions. In such cases, non-stoichiometry will be the norm.

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallization, by recrystallization from solvents, or by physically grinding the components together—see Chem Commun, 17, 1889-1896, by O. Almarsson and M. J. Zaworotko (2004). For a general review of multi-component complexes, see J Pharm Sci, 64 (8), 1269-1288, by Haleblian (August 1975).

The compounds of the invention include compounds of Formula (I) or (II) as hereinbefore defined, polymorphs, and isomers thereof (including optical, geometric and tautomeric isomers) as hereinafter defined and isotopically labelled compounds of Formula (I) or (II).

The compounds of the present invention may be administered as prodrugs. Thus certain derivatives of compounds of Formula (I) or (II) which may have little or no pharmacological activity themselves can, when administered into or onto the body, be converted into compounds of Formula (I) or (II) having the desired activity, for example, by hydrolytic cleavage. Such derivatives are referred to as 'prodrugs'. [Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E. B. Roche, American Pharmaceutical Association).]

Prodrugs can, for example, be produced by replacing appropriate functionalities present in the compounds of Formula (I) or (II) with certain moieties known to those skilled in the art as 'pro-moieties' as described, for example, in "Design of Prodrugs" by H. Bundgaard (Elsevier, 1985).

Some examples of such prodrugs include:

(i) where the compound of Formula (I) or (II) contains an alcohol functionality (—OH), an ether thereof, for example, replacement of the hydrogen with $(C_1-C_6)$alkanoyloxymethyl, or a phosphate ester $(PO_3H_2)$ or pharmaceutically acceptable salts thereof; and (ii) an amide or carbamate of the amino functionality present in Formula (I) or (II), wherein the hydrogen of the amino NH group is replaced with $(C_1-C_{10})$alkanoyl or $(C_1-C_{10})$alkoxycarbonyl, respectively.

Also included within the scope of the invention are active metabolites of compounds of Formula (I) or (II) (including prodrugs), that is, compounds formed in vivo upon administration of the drug, often by oxidation or dealkylation. Some examples of metabolites in accordance with the invention include:

(i) where the compound of Formula (I) or (II) contains a methyl group, a hydroxymethyl derivative thereof (—$CH_3$→—$CH_2OH$) and (ii) where the compound of Formula (I) or (II) contains an alkoxy group, a hydroxy derivative thereof (—OR→—OH).

Certain compounds of the present invention may exist in more than one crystal form (generally referred to as "polymorphs"). Polymorphs may be prepared by crystallization under various conditions, for example, using different solvents or different solvent mixtures for recrystallization;

crystallization at different temperatures; and/or various modes of cooling, ranging from very fast to very slow cooling during crystallization. Polymorphs may also be obtained by heating or melting the compound of the present invention followed by gradual or fast cooling. The presence of polymorphs may be determined by solid probe NMR spectroscopy, IR spectroscopy, differential scanning calorimetry, powder X-ray diffraction or such other techniques.

In general the compounds of this invention can be made by processes which include processes analogous to those known in the chemical arts, particularly in light of the description contained herein. Certain processes for the manufacture of the compounds of this invention are provided as further features of the invention and are illustrated by the following reaction schemes. Other processes may be described in the experimental section. Specific synthetic schemes for preparation of the compounds of Formula (I) or (II) are outlined below. Note that tetrazoles are generally a high energy functional group and care should be taken in the synthesis and handling of tetrazole containing molecules.

As an initial note, in the preparation of the Formula (I) or (II) compounds it is noted that some of the preparation methods useful for the preparation of the compounds described herein may require protection of remote functionality (e.g., primary amine, secondary amine, carboxyl in Formula (I) or (II) precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene, *Protective Groups in Organic Synthesis*, John Wiley & Sons, New York, 1991.

For example, certain compounds contain primary amines or carboxylic acid functionalities which may interfere with reactions at other sites of the molecule if left unprotected. Accordingly, such functionalities may be protected by an appropriate protecting group which may be removed in a subsequent step. Suitable protecting groups for amine and carboxylic acid protection include those protecting groups commonly used in peptide synthesis (such as N-tert-butoxycarbonyl, benzyloxycarbonyl, and 9-fluorenylmethylenoxycarbonyl for amines and lower alkyl or benzyl esters for carboxylic acids), which are generally not chemically reactive under the reaction conditions described and can typically be removed without chemically altering other functionality in the Formula (I) or (II) compound.

The compounds of the present invention may be synthesized by synthetic routes that include processes analogous to those well-known in the chemical arts, particularly in light of the description contained herein. The starting materials are generally available from commercial sources such as MilliporeSigma (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, New York (1967-1999 ed.), or *Beilsteins Handbuch der organischen Chemie*, 4, Aufl. ed. Springer-Verlag, Berlin, including supplements (also available via the *Beilstein* online database)). Many of the so compounds used herein, are related to, or are derived from compounds in which there is a large scientific interest and commercial need, and accordingly many such compounds are commercially available or are reported in the literature or are easily prepared from other commonly available substances by methods which are reported in the literature.

A detailed description of the individual reaction steps is provided in the Example section below. Those skilled in the art will appreciate that other synthetic routes may be used to synthesize the compounds. Although specific starting materials and reagents are discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

Combination Agents

The compounds of the present invention can be administered alone or in combination with one or more additional therapeutic agents. By "administered in combination" or "combination therapy" it is meant that a compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect. The phrases "concurrent administration," "co-administration," "simultaneous administration," and "administered simultaneously" mean that the compounds are administered in combination. Thus, the methods of prevention and treatment described herein include use of combination agents.

The combination agents are administered to a mammal in a therapeutically effective amount. By "therapeutically effective amount" it is meant an amount of a compound of the present invention that, when administered alone or in combination with an additional therapeutic agent to a mammal, is effective to treat the desired disease/condition (e.g., NASH, heart failure or diabetes).

Given the NASH/NAFLD activity of the compounds of this invention, they may be co-administered with other agents for the treatment of non-alcoholic steatohepatitis (NASH) and/or non-alcoholic fatty liver disease (NAFLD) and associated disease/conditions, such as Orlistat, TZDs and other insulin-sensitizing agents, FGF21 analogs, Metformin, Omega-3-acid ethyl esters (e.g. Lovaza), Fibrates, HMG CoA-reductase Inhibitors, Ezetimibe, Probucol, Ursodeoxycholic acid, TGR5 agonists, FXR agonists, Vitamin E, Betaine, Pentoxifylline, CB1 antagonists, Carnitine, N-acetylcysteine, Reduced glutathione, lorcaserin, the combination of naltrexone with buprorion, SGLT2 inhibitors (including dapagliflozin, canagliflozin, empagliflozin, tofogliflozin, ertugliflozin, ASP-1941, THR1474, TS-071, ISIS388626 and LX4211 as well as those in WO2010023594), Phentermine, Topiramate, GLP-1 receptor agonists, GIP receptor agonists, dual GLP-1 receptor/glucagon receptor agonists (e.g., OPK88003, MEDI0382, JNJ-64565111, NN9277, BI 456906), dual GLP-1 receprtor/GIP receptor agonists (e.g., Tirzepatide (LY3298176), NN9423), Angiotensin-receptor blockers an acetyl-CoA carboxylase (ACC) inhibitor, a BCKDK inhibitor, a ketohexokinase (KHK) inhibitor, ASK1 inhibitors, branched-chain alpha keto acid dehydrogenase kinase inhibitors (BCKDK inhibitors), inhibitors of CCR2 and/or CCR5, PNPLA3 inhibitors, DGAT1 inhibitors, an FGF21 analog, FGF19 analogs, PPAR agonists, FXR agonists, AMPK activators (e.g. ETC-1002 (bempedoic acid)), SCD1 inhibitors or MPO inhibitors.

Exemplary GLP-1 receptor agonists include liraglutide, albiglutide, exenatide, albiglutide, lixisenatide, dulaglutide, semaglutide, HM15211, LY3298176, Medi-0382, NN-9924, TTP-054, TTP-273, efpeglenatide, those described in WO2018109607, those described in PCT/IB2019/054867 filed Jun. 11, 2019, and those described in PCT/IB2019/054961 filed Jun. 13, 2019, including the following:

2-({4-[2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid;

2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-4-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(pyridin-3-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-5-ylmethyl)-1H-benzimidazole-6-carboxylic acid;

2-({4-[2-(4-chloro-2-fluorophenyl)-2-methyl-1,3-benzodioxol-4-yl]piperidin-1-yl}methyl)-1-[(1-ethyl-1H-1,2,3-triazol-5-yl)methyl]-1H-benzimidazole-6-carboxylic acid;

2-({4-[2-(4-chloro-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[2-(4-chloro-2-fluorophenyl)-7-fluoro-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(4-cyano-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;

2-({4-[(2S)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[(2R)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2;

2-[(4-{2-[(4-chloro-2-fluorobenzyl)oxy]pyridin-3-yl}piperid in-1-yl)methyl]-1-[(2S)-oxetan-2-ylmethyl]-1H-benzimidazole-6-carboxylic acid;

2-[(4-{2-[(4-chloro-2-fluorobenzyl)oxy]pyridin-3-yl}piperidin-1-yl)methyl]-1-(1,3-oxazol-2-ylmethyl)-1H-benzimidazole-6-carboxylic acid;

2-[(4-{2-[(4-cyano-2-fluorobenzyl)oxy]pyridin-3-yl}piperidin-1-yl)methyl]-1-(1,3-oxazol-2-ylmethyl)-1H-benzimidazole-6-carboxylic acid;

2-[(4-{2-[(4-cyano-2-fluorobenzyl)oxy]pyridin-3-yl}piperidin-1-yl)methyl]-1-[(2S)-oxetan-2-ylmethyl]-1H-benzimidazole-6-carboxylic acid;

2-[(4-{3-[(4-chloro-2-fluorobenzyl)oxy]pyrazin-2-yl}piperidin-1-yl)methyl]-1-[(2S)-oxetan-2-ylmethyl]-1H-benzimidazole-6-carboxylic acid;

2-(6-{6-[(4-cyano-2-fluorobenzyl)oxy]pyridin-2-yl}-6-azaspiro[2.5]oct-1-yl)-1-[(2S)-oxetan-2-ylmethyl]-1H-benzimidazole-6-carboxylic acid;

2-(6-{2-[(4-chloro-2-fluorobenzyl)oxy]-5-fluoropyrimidin-4-yl}-6-azaspiro[2.5]oct-1-yl)-1-[(2S)-oxetan-2-ylmethyl]-1H-benzimidazole-6-carboxylic acid;

2-(6-{2-[(4-chloro-2-fluorobenzyl)oxy]-5-fluoropyrimidin-4-yl}-6-azaspiro[2.5]oct-1-yl)-1-(1,3-oxazol-2-ylmethyl)-1H-benzimidazole-6-carboxylic acid;

2-(6-{6-[(4-cyano-2-fluorobenzyl)oxy]-5-fluoropyridin-2-yl}-6-azaspiro[2.5]oct-1-yl)-1-[(2S)-oxetan-2-ylmethyl]-1H-benzimidazole-6-carboxylic acid;

2-(6-{6-[(4-cyano-2-fluorobenzyl)oxy]-3-fluoropyridin-2-yl}-6-azaspiro[2.5]oct-1-yl)-1-[(2S)-oxetan-2-ylmethyl]-1H-benzimidazole-6-carboxylic acid;

2-[(4-{2-[(4-chloro-2-fluorobenzyl)oxy]pyrimidin-4-yl}piperidin-1-yl)methyl]-1-[(2S)-oxetan-2-ylmethyl]-1H-benzimidazole-6-carboxylic acid;

2-{[(2S)-4-{2-[(4-chloro-2-fluorobenzyl)oxy]-5-fluoropyrimidin-4-yl}-2-methylpiperazin-1-yl]methyl}-1-[(2S)-oxetan-2-ylmethyl]-1H-benzimidazole-6-carboxylic acid;

2-{[(2S)-4-{2-[(4-chloro-2-fluorobenzyl)oxy]pyrimidin-4-yl}-2-methylpiperazin-1-yl]methyl}-1-[(2S)-oxetan-2-ylmethyl]-1H-benzimidazole-6-carboxylic acid; and 2-[(4-{6-[(4-Cyano-2-fluorobenzyl)oxy]pyridin-2-yl}piperidin-1-yl)methyl]-1-[(2S)-oxetan-2-ylmethyl]-

1H-benzimidazole-6-carboxylic acid, and pharmaceutically acceptable salts thereof.

Exemplary ACC inhibitors include 4-(4-[(1-isopropyl-7-oxo-1,4,6,7-tetrahydro-1'H-spiro[indazole-5,4'-piperidin]-t-yl)carbonyl]-6-methoxypyridin-2-yl)benzoic acid, gemcabene, and firsocostat (GS-0976) and pharmaceutally acceptable salts thereof.

Exemplary FXR Agonists include tropifexor (2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid), cilofexor (GS-9674), obeticholic acid, LY2562175, Met409, TERN-101 and EDP-305 and pharmaceutically acceptable salts thereof.

Exemplary KHK inhibitors include [(1R,5S,6R)-3-{2-[(2S)-2-methylazetidin-1-yl]-6-(trifluoromethyl)pyrimidin-4-yl}-3-azabicyclo[3.1.0]hex-6-yl]acetic acid and pharmaceutically acceptable salts thereof.

Exemplary BCKDK inhibitors include those described in U.S. Ser. No. 62/868,057 filed Jun. 28, 2019 and U.S. Ser. No. 62/868,542 filed Jun. 28, 2019 including the following:
5-(5-chloro-4-fluoro 3-methylthiophen-2-yl)-1H-tetrazole;
5-(5-chloro-3-difluoromethylthiophen-2-yl)-1H-tetrazole;
5-(5-fluoro-3-methylthiophen-2-yl)-1H-tetrazole;
5-(5-chloro-3-methylthiophen-2-yl)-1H-tetrazole;
5-(3,5-dichlorothiophen-2-yl)-1H-tetrazole;
5-(4-bromo-3-methylthiophen-2-yl)-1H-tetrazole;
5-(4-bromo-3-ethylthiophen-2-yl)-1H-tetrazole;
5-(4-chloro-3-ethylthiophen-2-yl)-1H-tetrazole;
3-chloro-5-fluorothieno[3,2-b]thiophene-2-carboxylic acid;
3-bromo-5-fluorothieno[3,2-b]thiophene-2-carboxylic acid;
3-(difluoromethyl)-5-fluorothieno[3,2-b]thiophene-2-carboxylic acid;
5,6-difluorothieno[3,2-b]thiophene-2-carboxylic acid; and
3,5-difluorothieno[3,2-b]thiophene-2-carboxylic acid;
or a pharmaceutically acceptable salt thereof.

Given the anti-diabetic activity of the compounds of this invention they may be co-administered with other anti-diabetic agents. Suitable anti-diabetic agents include insulin, metformin, GLP-1 receptor agonists (described herein above), an acetyl-CoA carboxylase (ACC) inhibitor (described herein above), SGLT2 inhibitors (described herein above), monoacylglycerol O-acyltransferase inhibitors, phosphodiesterase (PDE)-10 inhibitors, AMPK activators (e.g. ETC-1002 (bempedoic acid)), sulfonylureas (e.g., acetohexamide, chlorpropamide, diabinese, glibenclamide, glipizide, glyburide, glimepiride, gliclazide, glipentide, gliquidone, glisolamide, tolazamide, and tolbutamide), meglitinides, α-amylase inhibitors (e.g., tendamistat, trestatin and AL-3688), an α-glucoside hydrolase inhibitor (e.g., acarbose), α-glucosidase inhibitors (e.g., adiposine, camiglibose, emiglitate, miglitol, voglibose, pradimicin-Q, and salbostatin), PPARγ agonists (e.g., balaglitazone, ciglitazone, darglitazone, englitazone, isaglitazone, pioglitazone and rosiglitazone), PPAR α/γ agonists (e.g., CLX-0940, GW-1536, GW-1929, GW-2433, KRP-297, L-796449, LR-90, MK-0767 and SB-219994), protein tyrosine phosphatase-1B (PTP-1B) inhibitors (e.g., trodusquemine, hyrtiosal extract, and compounds disclosed by Zhang, S., et al., *Drug Discovery Today*, 12(9/10), 373-381 (2007)), SIRT-1 activators (e.g., resveratrol, GSK2245840 or GSK184072), dipeptidyl peptidease IV (DPP-IV) inhibitors (e.g., those in WO2005116014, sitagliptin, vildagliptin, alogliptin, dutogliptin, linagliptin and saxagliptin), insulin secreatagogues, a fatty acid oxidation inhibitors, A2 antagonists, c-jun amino-terminal kinase (JNK) inhibitosr, glucokinase activators (GKa) such as those described in WO2010103437, WO2010103438, WO2010013161, WO2007122482, TTP-399, TTP-355, TTP-547, AZD1656, ARRY403, MK-0599, TAK-329, AZD5658 or GKM-001, insulin, insulin mimetics, glycogen phosphorylase inhibitors (e.g. GSK1362885), VPAC2 receptor agonists, glucagon receptor modulators such as those described in Demong, D. E. et al. Annual Reports in Medicinal Chemistry 2008, 43, 119-137, GPR119 modulators, particularly agonists, such as those described in WO2010140092, WO2010128425, WO2010128414, WO2010106457, Jones, R. M. et al. in Medicinal Chemistry 2009, 44, 149-170 (e.g. MBX-2982, GSK1292263, APD597 and PSN821), FGF21 derivatives or analogs such as those described in Kharitonenkov, A. et al., Current Opinion in Investigational Drugs 2009, 10(4)359-364, TGR5 (also termed GPBAR1) receptor modulators, particularly agonists, such as those described in Zhong, M., Current Topics in Medicinal Chemistry, 2010, 10(4), 386-396 and INT777, GPR40 agonists, such as those described in Medina, J. C., Annual Reports in Medicinal Chemistry, 2008, 43, 75-85, including but not limited to TAK-875, GPR120 modulators, particularly agonists, high affinity nicotinic acid receptor (HM74A) activators, and SGLT1 inhibitors, such as GSK1614235. A further representative listing of anti-diabetic agents that can be combined with the compounds of the present invention can be found, for example, at page 28, line 35 through page 30, line 19 of WO2011005611.

Other antidiabetic agents could include inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g. PKCα, PKCβ, PKCγ), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostain receptors (e.g. SSTR1, SSTR2, SSTR3 and SSTR5), inhibitors or modulators of PDHK2 or PDHK4, inhibitors of MAP4K4, modulators of IL1 family including IL1 beta, modulators of RXRalpha. In addition suitable anti-diabetic agents include mechanisms listed by Carpino, P. A., Goodwin, B. Expert Opin. Ther. Pat, 2010, 20(12), 1627-51.

The compounds of the present invention may be co-administered with anti-heart failure agents such as ACE inhibitors (e.g. captopril, enalapril, fosinopril, lisinopril, perindopril, quinapril, ramipril, trandolapril), Angiotensin II receptor blockers (e.g., candesartan, losartan, valsartan), Angiotensin-receptor neprilysin inhibitors (sacubitril/valsartan), If channel blocker Ivabradine, Beta-Adrenergic blocking agents (e.g., bisoprolol, metoprolol succinate, carvedilol), Aldosterone antagonists (e.g., spironolactone, eplerenone), hydralazine and isosorbide dinitrate, diuretics (e.g., furosemide, bumetanide, torsemide, chlorothiazide, amiloride, hydrochlorothiazide, Indapamide, Metolazone, Triamterene), or digoxin.

The compounds of the present invention may also be co-administered with cholesterol or lipid lowering agents including the following exemplary agents: HMG CoA reductase inhibitors (e.g., pravastatin, pitavastatin, lovastatin, atorvastatin, simvastatin, fluvastatin, NK-104 (a.k.a. itavastatin, or nisvastatin or nisbastatin) and ZD-4522 (a.k.a. rosuvastatin, or atavastatin or visastatin); squalene synthetase inhibitors; fibrates (e.g., gemfibrozil, pemafibrate, fenofibrate, clofibrate); bile acid sequestrants (such as questran, colestipol, colesevelam); ACAT inhibitors; MTP inhibitors; lipooxygenase inhibitors; cholesterol absorption inhibitors (e.g., ezetimibe); nicotinic acid agents (e.g., niacin, niacor, slo-niacin); omega-3 fatty acids (e.g., epanova, fish oil, eicosapentaenoic acid); cholesteryl ester transfer protein inhibitors (e.g., obicetrapib) and PCSK9 modulators (e.g., alirocumab, evolocumab, bococizumab, ALN-PCS (inclisiran)).

The compounds of the present invention may also be used in combination with antihypertensive agents and such antihypertensive activity is readily determined by those skilled in the art according to standard assays (e.g., blood pressure measurements). Examples of suitable anti-hypertensive agents include: alpha adrenergic blockers; beta adrenergic blockers; calcium channel blockers (e.g., diltiazem, verapamil, nifedipine and amlodipine); vasodilators (e.g., hydralazine), diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, torsemide, furosemide, musolimine, bumetanide, triamtrenene, amiloride, spironolactone); renin inhibitors; ACE inhibitors (e.g., captopril, zofenopril, fosinopril, enalapril, ceranopril, cilazopril, delapril, pentopril, quinapril, ramipril, lisinopril); AT-1 receptor antagonists (e.g., losartan, irbesartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual NEP-ACE inhibitors) (e.g., gemopatrilat and nitrates). An exemplary antianginal agent is ivabradine.

Examples of suitable calcium channel blockers (L-type or T-type) include diltiazem, verapamil, nifedipine and amlodipine and mybefradil.

Examples of suitable cardiac glycosides include digitalis and ouabain.

In one embodiment, a Formula (I) or (II) compound may be co-administered with one or more diuretics. Examples of suitable diuretics include (a) loop diuretics such as furosemide (such as LASIX™), torsemide (such as DEMADEX™), bemetanide (such as BUMEX™), and ethacrynic acid (such as EDECRIN™), (b) thiazide-type diuretics such as chlorothiazide (such as DIURIL™, ESIDRIX™ or HYDRODIURIL™) hydrochlorothiazide (such as MICROZIDE™ or ORETIC™), benzthiazide, hydroflumethiazide (such as SALURON™), bendroflumethiazide, methylchlorthiazide, polythiazide, trichlormethiazide, and indapamide (such as LOZOL™), (c) phthalimidine-type diuretics such as chlorthalidone (such as HYGROTON™), and metolazone (such as ZAROXOLYN™), (d) quinazoline-type diuretics such as quinethazone; and (e) potassium-sparing diuretics such as triamterene (such as DYRENIUM™), and amiloride (such as MIDAMOR™ or MODURETIC™).

In another embodiment, a compound of Formula (I) or (II) may be co-administered with a loop diuretic. In still another embodiment, the loop diuretic is selected from furosemide and torsemide. In still another embodiment, one or more compounds of Formula (I) or (II) may be co-administered with furosemide. In still another embodiment, one or more compounds of Formula (I) or (II) may be co-administered with torsemide which may optionally be a controlled or modified release form of torsemide.

In another embodiment, a compound of Formula (I) or (II) may be co-administered with a thiazide-type diuretic. In still another embodiment, the thiazide-type diuretic is selected from the group consisting of chlorothiazide and hydrochlorothiazide. In still another embodiment, one or more compounds of Formula (I) or (II) may be co-administered with chlorothiazide. In still another embodiment, one or more compounds of Formula (I) or (II) may be co-administered with hydrochlorothiazide.

In another embodiment, one or more compounds of Formula (I) or (II) may be co-administered with a phthalimidine-type diuretic. In still another embodiment, the phthalimidine-type diuretic is chlorthalidone.

Examples of suitable mineralocorticoid receptor antagonists include sprionolactone and eplerenone.

Examples of suitable phosphodiesterase inhibitors include: PDE III inhibitors (such as cilostazol); and PDE V inhibitors (such as sildenafil).

Those skilled in the art will recognize that the compounds of this invention may also be used in conjunction with other cardiovascular or cerebrovascular treatments including PCI, stenting, drug-eluting stents, stem cell therapy and medical devices such as implanted pacemakers, defibrillators, or cardiac resynchronization therapy.

Particularly when provided as a single dosage unit, the potential exists for a chemical interaction between the combined active ingredients. For this reason, when a Formula (I) or (II) compound and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that effects a sustained release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

In combination therapy treatment, both the compounds of this invention and the other drug therapies are administered to mammals (e.g., humans, male or female) by conventional methods. A Formula (I) or (II) compound and the salts thereof are all adapted to therapeutic use as agents that inhibit diacylglycerol acyltransferases 2 in mammals, particularly humans, and thus are useful for the treatment of the various conditions (e.g., those described herein) in which such action is implicated.

The disease/conditions that can be treated in accordance with the present invention include, but are not limited to, cardiovascular conditions, diabetes (e.g., type II) and diabetic complications, vascular conditions, NASH (non-alcoholic steatatohepatitis), NAFLD (non-alcoholic fatty liver disease) and renal diseases.

It is believed that DGAT2 inhibition exhibits beneficial effects on both glycemic control and plasma cholesterol profile such that this target is valuable in the treatment of metabolic disease (Choi, C. S. et. al. 2007. *J Biol Chem* 282: 22678-22688). Given the positive correlation between inhibition of DGAT2 with metabolic and associated disease/conditions, a Formula (I) or (II) compound, by virtue of the pharmacologic action, is useful for the prevention, arrestment and/or regression of metabolic and associated disease states (e.g., type II diabetes; NASH; NAFLD).

Hepatic triglycerides (TGs) are derived from 3 principal sources: de novo lipogenesis (DNL), re esterification from fatty acids (FAs) supplied by the adipose, and dietary intake (Cohen J. C. et al. 2011, *Science,* 332, 1519-1523). While the largest contribution to the hepatic TG pool appears to be derived from lipolytic products originating in adipocytes, the lipogenic pathway plays an important role in the development of NAFLD and progression to NASH. The contribution of DNL to disease progression in NAFLD is supported by analyzing the FA composition of TGs in subjects with and without NAFLD. Data demonstrate an increased level of saturated FAs in those with NAFLD, implicating the DNL pathway as an important contributor to hepatic steatosis as saturated FAs represent the primary product of DNL. These findings are consistent with the increased inclusion of DNL derived TGs in VLDL particles in NAFLD where 15% of TG produced originated from DNL compared to only 2 to 5% in normal subjects consuming a typical Western diet (Sanders, F. W. B. and, Griffin J. L., 2016, *Biol. Rev.,* 91, 452-468). Additionally, elevated rates of hepatic DNL have been reported to be a distinctive characteristic of NAFLD. Human subjects with elevated liver fat showed a more than 3-fold increase in the rate of hepatic DNL relative to subjects with normal liver fat, but no differences between the groups were detected in adipose free fatty acid (FFA) flux or in production of VLDL from FFAs. Consequently, when comparing the absolute sources of FAs incorporated into VLDL TG, elevated hepatic DNL was the only source significantly elevated in subjects with high liver fat (Lambert J. E. and Ramos-Roman, M. A., 2014, *Gastroenterology,* 146, 726-735).

Diacylglycerol acyltransferases (DGATs) catalyze the terminal step in TG synthesis; specifically, the esterification of a fatty acid (FA) with diacylglycerol (DAG) resulting in the formation of TG (Yen, C. L. et al. 2008, *J. Lipid Res.,* 49, 2283-2301). In mammals, two structurally unrelated DGAT enzymes (DGAT1 and DGAT2) have been characterized. DGAT1 is highly expressed in the intestine and plays a central role in fat absorption (Buhman, K. K., et al., 2002, *J. Biol. Chem.,* 277, 25474-25479). DGAT2 is highly expressed in liver and adipose (Cases, S., et al., 2001, *J. Biol. Chem.,* 276, 38870-38876). In preclinical models, blockade of hepatic DGAT2 using antisense oligonucleotides results in both down regulation of the expression of multiple genes encoding proteins involved in lipogenesis and parallel induction in oxidative pathways. The net result of these changes is a decrease in the levels of hepatic DAG and TG lipid which, in turn, reduces hepatocyte lipid burden and decreases hepatic very low density lipoprotein (VLDL) TG secretion (Choi, C. S. et. al. 2007. *J Biol Chem* 282: 22678-22688 and Yu, X. X. et al. 2005, *Hepatology,* 42, 362-371). Thus it is believed that pharmacological inhibition of DGAT2 will exhibit beneficial effects for the treatment of NAFLD/NASH and other metabolic diseases including glycemic control, and plasma cholesterol.

In particular, given the positive correlation between inhibition of DGAT2 with NASH/NAFLD and associated disease/conditions, a Formula (I) or (II) compound, by virtue of the pharmacologic action, is useful for the prevention, arrestment and/or regression of NASH/NAFLD and associated disease states Further, regulatory authority recognized conditional approval for Phase III studies in NASH is based on histological surrogate markers obtained by liver biopsy. These generally accepted surrogates are i) resolution of NASH without worsening of fibrosis (i.e. a numerical increase in fibrosis stage); ii) a one or more stage reduction in fibrosis without worsening of NASH. Details may be found in: Ratziu, A critical review of endpoints for non-cirrhotic NASH therapeutic trials, Journal of Hepatology, 2018, 68. 353-361, and references therein.

Additionally, regulatory authorities look to a change in the Nonalcoholic Fatty Liver Disease (NAFLD) Activity Score (NAS) from baseline. The NAFLD Activity Score (NAS) is a composite score equal to the sum of the steatosis grade (0-3), lobular inflammation grade (0-3), and hepatocellular ballooning grade (0-2), from centralized pathologist scoring of liver biopsies. The overall scale of the NAS is 0-8, with higher scores indicating more severe disease. The outcome measure, change from baseline in NAFLD Activity Score (NAS), has a possible range from −8 to +8, with negative values indicating a better outcome (improvement) and positive values indicating a worse outcome. Components of the NAS are scored as follows: Steatosis grade 0=<5% steatosis, 1=5-33% steatosis, 2=34-66% steatosis, 3=>66% steatosis. Lobular inflammation grade=amount of lobular inflammation (combines mononuclear, fat granulomas, and polymorphonuclear (pmn) foci): 0=0, 1=<2 under 20× magnification, 2=2-4 under 20× magnification, 3=>4 under 20× magnification. Hepatocellular ballooning 0=none, 1=mild, 2=more than mild.

Due to its pharmacologic action the Formula (I) or (II) compounds are useful for treating hyperlipidemia, Type I diabetes, Type II diabetes mellitus, idiopathic Type I diabetes (Type Ib), latent autoimmune diabetes in adults (LADA), early-onset Type 2 diabetes (EOD), youth-onset atypical diabetes (YOAD), maturity onset diabetes of the young (MODY), malnutrition-related diabetes, gestational diabetes, coronary heart disease, ischemic stroke, restenosis after angioplasty, peripheral vascular disease, intermittent claudication, myocardial infarction, dyslipidemia, post-prandial lipemia, conditions of impaired glucose tolerance (IGT), conditions of impaired fasting plasma glucose, metabolic acidosis, ketosis, arthritis, obesity, osteoporosis, hypertension, congestive heart failure, left ventricular hypertrophy, peripheral arterial disease, diabetic retinopathy, macular degeneration, cataract, diabetic nephropathy, glomerulosclerosis, chronic renal failure, diabetic neuropathy, metabolic syndrome, syndrome X, premenstrual syndrome, angina pectoris, thrombosis, atherosclerosis, transient ischemic attacks, stroke, vascular restenosis, hyperglycemia, hyperinsulinemia, hypertrygliceridemia, insulin resistance, impaired glucose metabolism, erectile dysfunction, skin and connective tissue disorders, foot ulcerations and ulcerative colitis, endothelial dysfunction and impaired vascular compliance, hyper apo B lipoproteinemia, Alzheimer's, schizophrenia, impaired cognition, inflammatory bowel disease, ulcerative colitis, Crohn's disease, and irritable bowel syndrome, non-alcoholic steatohepatitis (NASH), or non-alcoholic fatty liver disease (NAFLD).

Administration of the compounds of this invention can be via any method which delivers a compound of this invention systemically and/or locally. These methods include oral routes, parenteral, intraduodenal routes, buccal, intranasal etc. Generally, the compounds of this invention are administered orally, but parenteral administration (e.g., intravenous, intramuscular, subcutaneous or intramedullary) may be utilized, for example, where oral administration is inappropriate for the target or where the patient is unable to ingest the drug.

For administration to human patients, an oral daily dose of the compounds herein may be in the range 1 mg to 5000 mg depending, of course, on the mode of and frequency of administration, the disease state, and the age and condition of the patient, etc. An oral daily dose is in the range of 3 mg to 2000 mg may be used. A further oral daily dose is in the range of 5 mg to 1000 mg. For convenience, the compounds of the present invention can be administered in a unit dosage form. If desired, multiple doses per day of the unit dosage form can be used to increase the total daily dose. The unit dosage form, for example, may be a tablet or capsule containing about 0.1, 0.5, 1, 5, 10, 15, 20, 25, 30, 35, 40, 45, 50, 55, 60, 65, 70, 75, 80, 85, 90, 95, 100, 125, 150, 175, 200, 250, 300, 500, or 1000 mg of the compound of the present invention. The total daily dose may be administered in single or divided doses and may, at the physician's discretion, fall outside of the typical ranges given herein.

For administration to human patients, an infusion daily dose of the compounds herein may be in the range 1 mg to 2000 mg depending, of course, on the mode of and frequency of administration, the disease state, and the age and condition of the patient, etc. A further infusion daily dose is in the range of 5 mg to 1000 mg. The total daily dose may be administered in single or divided doses and may, at the physician's discretion, fall outside of the typical ranges given herein.

According to the methods of treatment of the invention, a compound of the present invention or a combination of a compound of the present invention and at least one additional pharmaceutical agent (referred to herein as a "combination") is administered to a subject in need of such treatment, preferably in the form of a pharmaceutical composition. In the combination aspect of the invention, the compound of the present invention and at least one other pharmaceutical agent (e.g., another anti-obesity agent,) may be administered either separately or in a pharmaceutical composition comprising both. It is generally preferred that such administration be oral.

When a combination of a compound of the present invention and at least one other pharmaceutical agent are administered together, such administration may be sequential in time or simultaneous. Simultaneous administration of drug combinations is generally preferred. For sequential administration, a compound of the present invention and the additional pharmaceutical agent may be administered in any order. It is generally preferred that such administration be oral. It is especially preferred that such administration be oral and simultaneous. When a compound of the present invention and the additional pharmaceutical agent are administered sequentially, the administration of each may be by the same or by different methods.

According to the methods of the invention, a compound of the present invention or a combination is preferably administered in the form of a pharmaceutical composition. Accordingly, a compound of the present invention or a combination can be administered to a patient separately or together in any conventional oral, rectal, transdermal, parenteral (e.g., intravenous, intramuscular or subcutaneous), intracisternal, intravaginal, intraperitoneal, topical (e.g., powder, ointment, cream, spray or lotion), buccal or nasal dosage form (e.g., spray, drops or inhalant).

The compounds of the invention or combinations can be administered alone but will generally be administered in an admixture with one or more suitable pharmaceutical excipients, adjuvants, diluents or carriers known in the art and selected with regard to the intended route of administration and standard pharmaceutical practice. The compound of the invention or combination may be formulated to provide immediate-, delayed-, modified-, sustained-, pulsed- or controlled-release dosage forms depending on the desired route of administration and the specificity of release profile, commensurate with therapeutic needs.

The pharmaceutical composition comprises a compound of the invention or a combination in an amount generally in the range of from about 1% to about 75%, 80%, 85%, 90% or even 95% (by weight) of the composition, usually in the range of about 1%, 2% or 3% to about 50%, 60% or 70%, more frequently in the range of about 1%, 2% or 3% to less than 50% such as about 25%, 30% or 35%.

Methods of preparing various pharmaceutical compositions with a specific amount of active compound are known to those skilled in this art. For examples, see Remington: The Practice of Pharmacy, Lippincott Williams and Wilkins, Baltimore Md. 20.sup.th ed. 2000.

Compositions suitable for parenteral injection generally include pharmaceutically acceptable sterile aqueous or non-aqueous solutions, dispersions, suspensions, or emulsions, and sterile powders for reconstitution into sterile injectable solutions or dispersions. Examples of suitable aqueous and nonaqueous carriers or diluents (including solvents and vehicles) include water, ethanol, polyols (propylene glycol, polyethylene glycol, glycerol, and the like), suitable mixtures thereof, triglycerides including vegetable oils such as olive oil, and injectable organic esters such as ethyl oleate. A preferred carrier is Miglyol® brand caprylic/capric acid ester with glycerine or propylene glycol (e.g., Miglyol® 812, Miglyol® 829, Miglyol® 840) available from Condea Vista Co., Cranford, N.J. Proper fluidity can be maintained, for example, by the use of a coating such as lecithin, by the maintenance of the required particle size in the case of dispersions, and by the use of surfactants.

These compositions for parenteral injection may also contain excipients such as preserving, wetting, emulsifying, and dispersing agents. Prevention of microorganism contamination of the compositions can be accomplished with various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and gelatin.

Solid dosage forms for oral administration include capsules, tablets, chews, lozenges, pills, powders, and multiparticulate preparations (granules). In such solid dosage forms, a compound of the present invention or a combination is admixed with at least one inert excipient, diluent or carrier. Suitable excipients, diluents or carriers include materials such as sodium citrate or dicalcium phosphate and/or (a) one or more fillers or extenders (e.g., microcrystalline cellulose (available as Avicel™ from FMC Corp.) starches, lactose, sucrose, mannitol, silicic acid, xylitol, sorbitol, dextrose, calcium hydrogen phosphate, dextrin, alpha-cyclodextrin, beta-cyclodextrin, polyethylene glycol, medium chain fatty acids, titanium oxide, magnesium oxide, aluminum oxide and the like); (b) one or more binders (e.g., carboxymethylcellulose, methylcellulose, hydroxypropylcellulose, hydroxypropylmethylcellulose, gelatin, gum arabic, ethyl cellulose, polyvinyl alcohol, pullulan, pregelatinized starch, agar, tragacanth, alginates, gelatin, polyvinylpyrrolidone, sucrose, acacia and the like); (c) one or more humectants (e.g., glycerol and the like); (d) one or more disintegrating agents (e.g., agar-agar, calcium carbonate, potato or tapioca starch, alginic acid, certain complex silicates, sodium carbonate, sodium lauryl sulphate, sodium starch glycolate (available as Explotab™ from Edward Mendell Co.), cross-linked polyvinyl pyrrolidone, croscarmellose sodium A-type (available as Ac-di-sol™), polyacrilin potassium (an ion exchange resin) and the like); (e) one or more solution retarders (e.g., paraffin and the like); (f) one or more absorption accelerators (e.g., quaternary ammonium compounds and the like); (g) one or more wetting agents (e.g., cetyl alcohol, glycerol monostearate and the like); (h) one or more adsorbents (e.g., kaolin, bentonite and the like); and/or lone or more lubricants (e.g., talc, calcium stearate, magnesium stearate, stearic acid, polyoxyl stearate, cetanol, talc, hydrogenated caster oil, sucrose esters of fatty acid, dimethylpolysiloxane, microcrystalline wax, yellow beeswax, white beeswax, solid polyethylene glycols, sodium lauryl sulfate and the like). In the case of capsules and tablets, the dosage forms may also comprise buffering agents.

Solid compositions of a similar type may also be used as fillers in soft or hard filled gelatin capsules using such excipients as lactose or milk sugar, as well as high molecular weight polyethylene glycols, and the like.

Solid dosage forms such as tablets, dragees, capsules, and granules may be prepared with coatings and shells, such as enteric coatings and others well known in the art. They may also contain opacifying agents, and can also be of such composition that they release the compound of the present invention and/or the additional pharmaceutical agent in a delayed manner. Examples of embedding compositions that can be used are polymeric substances and waxes. The drug may also be in micro-encapsulated form, if appropriate, with one or more of the above-mentioned excipients.

For tablets, the active agent will typically comprise less than 50% (by weight) of the formulation, for example less than about 10% such as 5% or 2.5% by weight. The predominant portion of the formulation comprises fillers, diluents, disintegrants, lubricants and optionally, flavors. The composition of these excipients is well known in so the art. Frequently, the fillers/diluents will comprise mixtures of two or more of the following components: microcrystalline cellulose, mannitol, lactose (all types), starch, and di-calcium phosphate. The filler/diluent mixtures typically comprise less than 98% of the formulation and preferably less than 95%, for example 93.5%. Preferred disintegrants include Ac-di-sol™, Explotab™, starch and sodium lauryl sulphate. When present a disintegrant will usually comprise less than 10% of the formulation or less than 5%, for example about 3%. A preferred lubricant is magnesium stearate. When present a lubricant will usually comprise less than 5% of the formulation or less than 3%, for example about 1%.

Tablets may be manufactured by standard tabletting processes, for example, direct compression or a wet, dry or melt granulation, melt congealing process and extrusion. The tablet cores may be mono or multi-layer(s) and can be coated with appropriate overcoats known in the art.

Liquid dosage forms for oral administration include pharmaceutically acceptable emulsions, solutions, suspensions, syrups, and elixirs. In addition to the compound of the present invention or the combination, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed oil, groundnut oil, corn germ oil, olive oil, castor oil, sesame seed oil and the like), Miglyole® (available from CONDEA Vista Co., Cranford, N.J.), glycerol, tetrahydrofurfuryl alcohol, polyethylene glycols and fatty acid esters of sorbitan, or mixtures of these substances, and the like.

Besides such inert diluents, the composition may also include excipients, such as wetting agents, emulsifying and suspending agents, sweetening, flavoring, and perfuming agents.

Oral liquid forms of the compounds of the invention or combinations include solutions, wherein the active compound is fully dissolved. Examples of solvents include all pharmaceutically precedented solvents suitable for oral administration, particularly those in which the compounds of the invention show good solubility, e.g., polyethylene glycol, polypropylene glycol, edible oils and glyceryl- and glyceride-based systems. Glyceryl- and glyceride-based systems may include, for example, the following branded products (and corresponding generic products): Captex™ 355 EP (glyceryl tricaprylate/caprate, from Abitec, Columbus Ohio), Crodamol™ GTC/C (medium chain triglyceride, from Croda, Cowick Hall, UK) or Labrafac™ CC (medium chain triglyides, from Gattefosse), Captex™ 500P (glyceryl triacetate i.e. triacetin, from Abitec), Capmul™ MCM (medium chain mono- and diglycerides, fromAbitec), Migyol™ 812 (caprylic/capric triglyceride, from Condea, Cranford N.J.), Migyol™ 829 (caprylic/capric/succinic triglyceride, from Condea), Migyol™ 840 (propylene glycol dicaprylate/dicaprate, from Condea), Labrafil™ M1944CS (oleoyl macrogol-6 glycerides, from Gattefosse), Peceol™ (glyceryl monooleate, from Gattefosse) and Maisine™ 35-1 (glyceryl monooleate, from Gattefosse). Of particular interest are the medium chain (about $C_8$ to $C_{10}$) triglyceride oils. These solvents frequently make up the predominant portion of the composition, i.e., greater than about 50%, usually greater than about 80%, for example about 95% or 99%. Adjuvants and additives may also be included with the solvents principally as taste-mask agents, palatability and flavoring agents, antioxidants, stabilizers, texture and viscosity modifiers and solubilizers.

Suspensions, in addition to the compound of the present invention or the combination, may further comprise carriers such as suspending agents, e.g., ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal or vaginal administration preferably comprise suppositories, which can be prepared by mixing a compound of the present invention or a combination with suitable non-irritating excipients or carriers, such as cocoa butter, polyethylene glycol or a suppository wax which are solid at ordinary room temperature, but liquid at body temperature, and therefore, melt in the rectum or vaginal cavity thereby releasing the active component(s).

Dosage forms for topical administration of the compounds of the present invention or combinations include ointments, creams, lotions, powders and sprays. The drugs are admixed with a pharmaceutically acceptable excipient, diluent or carrier, and any preservatives, buffers, or propellants that may be required.

Some of the present compounds may be poorly soluble in water, e.g., less than about 1 μg/mL. Therefore, liquid compositions in solubilizing, non-aqueous solvents such as the medium chain triglyceride oils discussed above are a preferred dosage form for these compounds.

Solid amorphous dispersions, including dispersions formed by a spray-drying process, are also a preferred dosage form for the poorly soluble compounds of the invention. By "solid amorphous dispersion" is meant a solid material in which at least a portion of the poorly soluble compound is in the amorphous form and dispersed in a water-soluble polymer. By "amorphous" is meant that the poorly soluble compound is not crystalline. By "crystalline" is meant that the compound exhibits long-range order in three dimensions of at least 100 repeat units in each dimension. Thus, the term amorphous is intended to include not only material which has essentially no order, but also material which may have some small degree of order, but the order is in less than three dimensions and/or is only over short distances. Amorphous material may be characterized by techniques known in the art such as powder x-ray diffraction (PXRD) crystallography, solid state NMR, or thermal techniques such as differential scanning calorimetry (DSC).

Preferably, at least a major portion (i.e., at least about 60 wt %) of the poorly soluble compound in the solid amorphous dispersion is amorphous. The compound can exist within the solid amorphous dispersion in relatively pure amorphous domains or regions, as a solid solution of the compound homogeneously distributed throughout the polymer or any combination of these states or those states that lie intermediate between them. Preferably, the solid amorphous dispersion is substantially homogeneous so that the amorphous compound is dispersed as homogeneously as possible throughout the polymer. As used herein, "substantially homogeneous" means that the fraction of the compound that is present in relatively pure amorphous domains or regions within the solid amorphous dispersion is relatively small, on the order of less than 20 wt %, and preferably less than 10 wt % of the total amount of drug.

Water-soluble polymers suitable for use in the solid amorphous dispersions should be inert, in the sense that they do not chemically react with the poorly soluble compound in an adverse manner, are pharmaceutically acceptable, and have at least some solubility in aqueous solution at physiologically relevant pHs (e.g. 1-8). The polymer can be neutral or ionizable, and should have an aqueous-solubility of at least 0.1 mg/mL over at least a portion of the pH range of 1-8.

Water-soluble polymers suitable for use with the present invention may be cellulosic or non-cellulosic. The polymers may be neutral or ionizable in aqueous solution. Of these, ionizable and cellulosic polymers are preferred, with ionizable cellulosic polymers being more preferred.

Exemplary water-soluble polymers include hydroxypropyl methyl cellulose acetate succinate (HPMCAS), hydroxypropyl methyl cellulose (HPMC), hydroxypropyl methyl cellulose phthalate (HPMCP), carboxy methyl ethyl cellulose (CMEC), cellulose acetate phthalate (CAP), cellulose acetate trimellitate (CAT), polyvinylpyrrolidone (PVP), hydroxypropyl cellulose (HPC), methyl cellulose (MC), block copolymers of ethylene oxide and propylene oxide (PEO/PPO, also known as poloxamers), and mixtures thereof. Especially preferred polymers include HPMCAS, HPMC, HPMCP, CMEC, CAP, CAT, PVP, poloxamers, and mixtures thereof. Most preferred is HPMCAS. See European Patent Application Publication No. 0 901 786 A2, the disclosure of which is incorporated herein by reference.

The solid amorphous dispersions may be prepared according to any process for forming solid amorphous dispersions that results in at least a major portion (at least 60%) of the poorly soluble compound being in the amorphous state. Such processes include mechanical, thermal and solvent processes. Exemplary mechanical processes include milling and extrusion; melt processes including high temperature fusion, solvent-modified fusion and melt-congeal processes; and solvent processes including non-solvent precipitation, spray coating and spray drying. See, for example, the following U.S. patents, the pertinent disclosures of which are incorporated herein by reference: U.S. Pat. Nos. 5,456,923 and 5,939,099, which describe forming dispersions by extrusion processes; U.S. Pat. Nos. 5,340,591 and 4,673,564, which describe forming dispersions by milling processes; and U.S. Pat. Nos. 5,707,646 and 4,894,235, which describe forming dispersions by melt congeal processes. In a preferred process, the solid amorphous dispersion is formed by spray drying, as disclosed in European Patent Application Publication No. 0 901 786 A2. In this process, the compound and polymer are dissolved in a solvent, such as acetone or methanol, and the solvent is then rapidly removed from the solution by spray drying to form the solid amorphous dispersion. The solid amorphous dispersions may be prepared to contain up to about 99 wt % of the compound, e.g., 1 wt %, 5 wt %, 10 wt %, 25 wt %, 50 wt %, 75 wt %, 95 wt %, or 98 wt % as desired.

The solid dispersion may be used as the dosage form itself or it may serve as a manufacturing-use-product (MUP) in the preparation of other dosage forms such as capsules, tablets, solutions or suspensions. An example of an aqueous suspension is an aqueous suspension of a 1:1 (w/w) compound/HPMCAS-HF spray-dried dispersion containing 2.5 mg/mL of compound in 2% polysorbate-80. Solid dispersions for use in a tablet or capsule will generally be mixed with other excipients or adjuvants typically found in such dosage forms. For example, an exemplary filler for capsules contains a 2:1 (w/w) compound/HPMCAS-MF spray-dried dispersion (60%), lactose (fast flow) (15%), microcrystalline cellulose (e.g., Avicel.sup.(R0-102) (15.8%), sodium starch (7%), sodium lauryl sulfate (2%) and magnesium stearate (1%).

The HPMCAS polymers are available in low, medium and high grades as Aqoa.sup.®-LF, Aqoat.sup.®-MF and Aqoat-.sup.®-HF respectively from Shin-Etsu Chemical Co., LTD, Tokyo, Japan. The higher MF and HF grades are generally preferred.

Conveniently, a compound of the present invention (or combination) can be carried in the drinking water so that a therapeutic dosage of the compound is ingested with the daily water supply. The compound can be directly metered into drinking water, preferably in the form of a liquid, water-soluble concentrate (such as an aqueous solution of a water-soluble salt).

These compounds may also be administered to animals other than humans, for example, for the indications detailed above. The precise dosage administered of each active ingredient will vary depending upon any number of factors, including but not limited to, the type of animal and type of disease state being treated, the age of the animal, and the route(s) of administration.

A dosage of the combination pharmaceutical agents to be used in conjuction with the Formula (I) or (II) compounds is used that is effective for the indication being treated. Such dosages can be determined by standard assays such as those referenced above and provided herein. The combination agents may be administered simultaneously or sequentially in any order.

These dosages are based on an average human subject having a weight of about 60 kg to 70 kg. The physician will readily be able to determine doses for subjects whose weight falls outside this range, such as infants and the elderly.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regiments for administration of the chemotherapeutic agent are well-known in the relevant art and would be understood to be encompassed by the skilled artisan once provided the teachings disclosed herein.

The present invention further comprises use of a compound of Formula (I) or (II) for use as a medicament (such as a unit dosage tablet or unit dosage capsule). In another embodiment, the present invention comprises the use of a compound of Formula (I) or (II) for the manufacture of a medicament (such as a unit dosage tablet or unit dosage capsule) to treat one or more of the conditions previously identified in the above sections discussing methods of treatment.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

These agents and compounds of the invention can be combined with pharmaceutically acceptable vehicles such as saline, Ringer's solution, dextrose solution, and the like. The particular dosage regimen, i.e., dose, timing and repetition, will depend on the particular individual and that individual's medical history.

Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or Igs; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Liposomes containing these agents and/or compounds of the invention are prepared by methods known in the art, such as described in U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

These agents and/or the compounds of the invention may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nanoparticles and nanocapsules) or in macroemulsions. Such techniques are disclosed in Remington, The Science and Practice of Pharmacy, 20th Ed., Mack Publishing (2000).

Sustained-release preparations may be used. Suitable examples of sustained-release preparations include semipermeable matrices of solid hydrophobic polymers containing the compound of the invention, which matrices are in the form of shaped articles, e.g., films, or microcapsules. Examples of sustained-release matrices include polyesters, hydrogels (for example, poly(2-hydroxyethyl-methacrylate), or 'poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as those used in LUPRON DEPOT™ (injectable microspheres composed of lactic acid-glycolic acid copolymer and leuprolide acetate), sucrose acetate isobutyrate, and poly-D-(−)-3-hydroxybutyric acid.

The formulations to be used for intravenous administration must be sterile. This is readily accomplished by, for example, filtration through sterile filtration membranes. Compounds of the invention are generally placed into a container having a sterile access port, for example, an intravenous solution bag or vial having a stopper pierceable by a hypodermic injection needle.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 µm, particularly 0.1 and 0.5 µm, and have a pH in the range of 5.5 to 8.0.

The emulsion compositions can be those prepared by mixing a compound of the invention with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The compounds herein may be formulated for oral, buccal, intranasal, parenteral (e.g., intravenous, intramuscular or subcutaneous) or rectal administration or in a form suitable for administration by inhalation. The compounds of the invention may also be formulated for sustained delivery.

Methods of preparing various pharmaceutical compositions with a certain amount of active ingredient are known, or will be apparent in light of this disclosure, to those skilled in this art. For examples of methods of preparing pharmaceutical compositions see *Remington's Pharmaceutical Sciences*, 20th Edition (Lippincott Williams & Wilkins, 2000).

Pharmaceutical compositions according to the invention may contain 0.1%-95% of the compound(s) of this invention, preferably 1%-70%. In any event, the composition to be administered will contain a quantity of a compound(s) according to the invention in an amount effective to treat the disease/condition of the subject being treated.

Since the present invention has an aspect that relates to the treatment of the disease/conditions described herein with a combination of active ingredients which may be administered separately, the invention also relates to combining separate pharmaceutical compositions in kit form. The kit comprises two separate pharmaceutical compositions: a compound of Formula (I) or (II) a prodrug thereof or a salt of such compound or prodrug and a second compound as described above. The kit comprises a means for containing the separate compositions such as a container, a divided bottle or a divided foil packet. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet.

Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, etc. . . . Second Week, Monday, Tuesday, . . . " etc. Other variations of memory aids will be readily apparent. A "daily dose" can be a single tablet or capsule or several pills or capsules to be taken on a given day. Also, a daily dose of Formula (I) or (II) compound can consist of one tablet or capsule while a daily dose of the second compound can consist of several tablets or capsules and vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

Also, as the present invention has an aspect that relates to the treatment of the disease/conditions described herein with a combination of active ingredients which may be administered jointly, the invention also relates to combining separate pharmaceutical compositions in a single dosage form, such as (but not limited to) a single tablet or capsule, a bilayer or multilayer tablet or capsule, or through the use of segregated components or compartments within a tablet or capsule.

The active ingredient may be delivered as a solution in an aqueous or non-aqueous vehicle, with or without additional solvents, co-solvents, excipients, or complexation agents selected from pharmaceutically acceptable diluents, excipients, vehicles, or carriers.

The active ingredient may be formulated as a solid dispersion or as a self emulsified drug delivery system (SEDDS) with pharmaceutically acceptable excipients.

The active ingredient may be formulated as an immediate release or suspended release tablet or capsule. Alternatively, the active ingredient may be delivered as the active ingredient alone within a capsule shell, without additional excipients.

EXAMPLES

Experimental Procedures

Unless specified otherwise, starting materials are generally available from commercial sources such as Aldrich Chemicals Co. (Milwaukee, Wis.), Lancaster Synthesis, Inc. (Windham, N.H.), Acros Organics (Fairlawn, N.J.), Maybridge Chemical Company, Ltd. (Cornwall, England) and Tyger Scientific (Princeton, N.J.). Certain common abbreviations and acronyms have been employed which may include: AcOH (acetic acid), DBU (1,8-diazabicyclo[5.4.0] undec-7-ene), CDI (1,1'-carbonyldiimidazole), DCM (dichloromethane), DEA (diethylamine), DIPEA (N,N-diisopropylethylamine), DMAP (4-dimethylaminopyridine), DMF (N,N-dimethylformamide), DMSO (dimethyl sulfoxide), EDCI (1-[3-(dimethylamino)propyl]-3-ethylcarbodiimide hydrochloride), $Et_2O$ (diethyl ether), EtOAc (ethyl acetate), EtOH (ethanol), HATU (O-(7-azabenzotriazol-1-yl)-N,N,N',N'-tetramethyluronium hexafluorophosphate), HBTU (O-benzotriazol-1-yl-N,N,N',N'-tetramethyluronium hexafluorophosphate), HOBT (1-hydroxybenzotriazole), iPrOH (2-propanol), KHMDS (potassium bis(trimethylsilyl) amide), MeOH (methanol), MTBE (tert-butyl methyl ether), $NaBH(OAc)_3$ (sodium triacetoxyborohydride), NaHMDS (sodium bis(trimethylsilyl)amide), NMP (N-methylpyrrolidone), SEM ([2-(trimethylsilyl)ethoxy]methyl), TEA (triethylamine), TFA (trifluoroacetic acid), THF (tetrahydrofuran), and T3P (propane phosphonic acid anhydride; 2,4,6-tripropyl-1,3,5,2,4,6-trioxatriphosphinane 2,4,6-trioxide).

Reactions were performed in air or, when oxygen- or moisture-sensitive reagents or intermediates were employed, under an inert atmosphere (nitrogen or argon). When appropriate, reaction apparatuses were dried under dynamic vacuum using a heat gun, and anhydrous solvents (Sure-Seal™ products from Aldrich Chemical Company, Milwaukee, Wis. or DriSolv™ products from EMD Chemicals, Gibbstown, N.J.) were employed. In some cases, commercial solvents were passed through columns packed with 4 Å molecular sieves, until the following QC standards for water were attained: a) <100 ppm for dichloromethane, toluene, N,N-dimethylformamide, and tetrahydrofuran; b) <180 ppm for methanol, ethanol, 1,4-dioxane, and diisopropylamine. For very sensitive reactions, solvents were further treated with metallic sodium, calcium hydride, or molecular sieves, and distilled just prior to use. Other commercial solvents and reagents were used without further purification. For syntheses referencing procedures in other Examples or Methods, reaction conditions (reaction time and temperature) may vary. Products were generally dried under vacuum before being carried on to further reactions or submitted for biological testing.

When indicated, reactions were heated by microwave irradiation using Biotage Initiator or Personal Chemistry Emrys Optimizer microwaves. Reaction progress was monitored using thin-layer chromatography (TLC), liquid chromatography-mass spectrometry (LCMS), and/or high-performance liquid chromatography (HPLC). TLC was performed on pre-coated silica gel plates with a fluorescence indicator (254 nm excitation wavelength) and visualized under UV light and/or with $I_2$, $KMnO_4$, $CoCl_2$, phosphomolybdic acid, and/or ceric ammonium molybdate stains. LCMS data were acquired on an Agilent 1100 Series instrument with a Leap Technologies autosampler, Gemini C18 columns, MeCN/water gradients, and either TFA, formic acid, or ammonium hydroxide modifiers. The column eluent was analyzed using a Waters ZQ mass spectrometer scanning in both positive and negative ion modes from 100 to 1200 Da. Other similar instruments were also used. HPLC data were acquired on an Agilent 1100 Series instrument using Gemini or XBridge C18 columns, MeCN/water gradients, and either TFA or ammonium hydroxide modifiers. The sample was analyzed on an HP 5973 mass selective detector scanning from 50 to 550 Da using electron ionization. Purifications were performed by medium performance liquid chromatography (MPLC) using Isco CombiFlash Companion, AnaLogix IntelliFlash 280, Biotage SP1, or Biotage Isolera One instruments and pre-packed Isco RediSep or Biotage Snap silica cartridges. Chiral purifications were performed by chiral supercritical fluid chromatography (SFC) using Berger or Thar instruments; ChiralPAK-AD, -AS, -IC, Chiralcel-OD, or -OJ columns; and $CO_2$ mixtures with MeOH, EtOH, iPrOH, or MeCN, alone or modified using TFA or $iPrNH_2$. UV detection was used to trigger fraction collection. For syntheses referencing procedures in other Examples or Methods, purifications may vary: in general, solvents and the solvent ratios used for eluents/gradients were chosen to provide appropriate Rfs or retention times.

Mass spectrometry data are reported from LCMS analyses. Mass spectrometry (MS) was performed via atmospheric pressure chemical ionization (APCI), electrospray Ionization (ESI), electron impact ionization (EI) or electron scatter (ES) ionization sources. Proton nuclear magnetic spectroscopy ($^1H$ NMR) chemical shifts are given in parts per million downfield from tetramethylsilane and were recorded on on 300, 400, 500, or 600 MHz Varian, Bruker, or Jeol spectrometers. Chemical shifts are expressed in parts per million (ppm, δ) referenced to the deuterated solvent residual peaks (chloroform, 7.26 ppm; $CD_2HOD$, 3.31 ppm; acetonitrile-$d_2$, 1.94 ppm; dimethyl sulfoxide-$d_5$, 2.50 ppm; DHO, 4.79 ppm). The peak shapes are described as follows: s, singlet; d, doublet; t, triplet; q, quartet; quin, quintet; m, multiplet; br s, broad singlet; app, apparent. Analytical SFC data were acquired on a Berger analytical instrument as described above. Optical rotation data were acquired on a PerkinElmer model 343 polarimeter using a 1 dm cell. Silica gel chromatography was performed primarily using medium-pressure Biotage or ISCO systems using columns pre-packaged by various commercial vendors including Biotage and ISCO. Microanalyses were performed by Quantitative Technologies Inc. and were within 0.4% of the calculated values.

Unless otherwise noted, chemical reactions were performed at room temperature (about 23 degrees Celsius).

Unless noted otherwise, all reactants were obtained commercially without further purifications or were prepared using methods known in the literature.

The terms "concentrated", "evaporated", and "concentrated in vacuo" refer to the removal of solvent at reduced pressure on a rotary evaporator with a bath temperature less than 60° C. The abbreviation "min" and "h" stand for "minutes" and "hours" respectively. The term "TLC" refers to thin-layer chromatography, "room temperature or ambient temperature" means a temperature between 18 to 25° C., "LCMS" refers to liquid chromatography-mass spectrometry, "UPLC" refers to ultra-performance liquid chromatography and "HPLC" refers to high-performance liquid chromatography, "SFC" refers to supercritical fluid chromatography.

Hydrogenation may be performed in a Parr Shaker under pressurized hydrogen gas, or in Thales-nano H-Cube flow hydrogenation apparatus at full hydrogen and a flow rate between 1-2 mL/min at specified temperature.
HPLC, UPLC, LCMS, and SFC retention times were measured using the methods noted in the procedures.

In some examples, chiral separations were carried out to separate enantiomers of certain compounds of the invention (in some examples, the separated enantiomers are designated as ENT-1 and ENT-2, according to their order of elution; similarly, separated diastereomers are designated as DIAST-1 and DIAST-2, according to their order of elution). In some examples, the optical rotation of an enantiomer was measured using a polarimeter. According to its observed rotation data (or its specific rotation data), an enantiomer with a clockwise rotation was designated as the (+)-enantiomer and an enantiomer with a counter-clockwise rotation was designated as the (−)-enantiomer. Racemic compounds are indicated either by the absence of drawn or described stereochemistry, or by the presence of (+/−) adjacent to the structure; in this latter case, the indicated stereochemistry represents just one of the two enantiomers that make up the racemic mixture.

The following illustrate the synthesis of various compounds of the present invention. Additional compounds within the scope of this invention may be prepared using the methods illustrated in these Examples, either alone or in combination with techniques generally known in the art. All starting materials in these Preparations and Examples are either commercially available or can be prepared by methods known in the art or as described herein.

The compounds and intermediates described below were named using the naming convention provided with ACD/ChemSketch 2017.2.1, File Version C40H41, Build 99535 (Advanced Chemistry Development, Inc., Toronto, Ontario, Canada). The naming convention provided with ACD/ChemSketch 2017.2.1 is well known by those skilled in the art and it is believed that the naming convention provided with ACD/ChemSketch 2017.2.1 generally comports with the IUPAC (International Union for Pure and Applied Chemistry) recommendations on Nomenclature of Organic Chemistry and the CAS Index rules.

Preparation P1

2-{5-[(3-Ethoxypyridin-2-yl)oxy]pyridin-3-yl}pyrimidine-5-carboxylic acid (P1)

P1

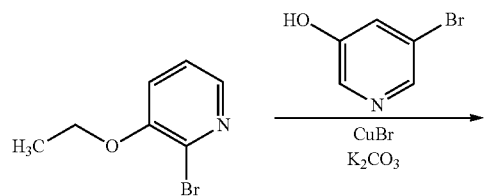

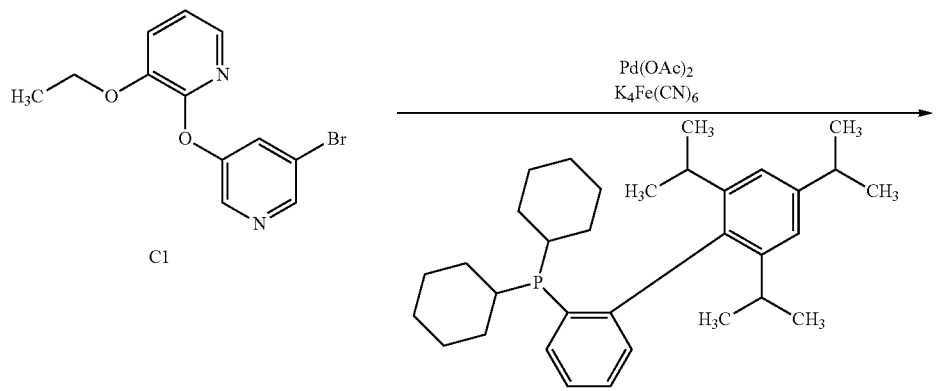

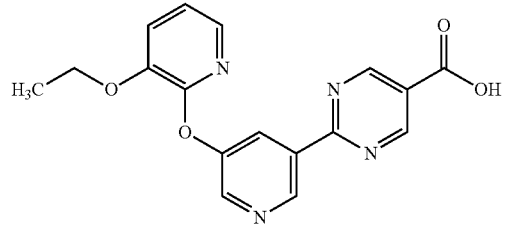

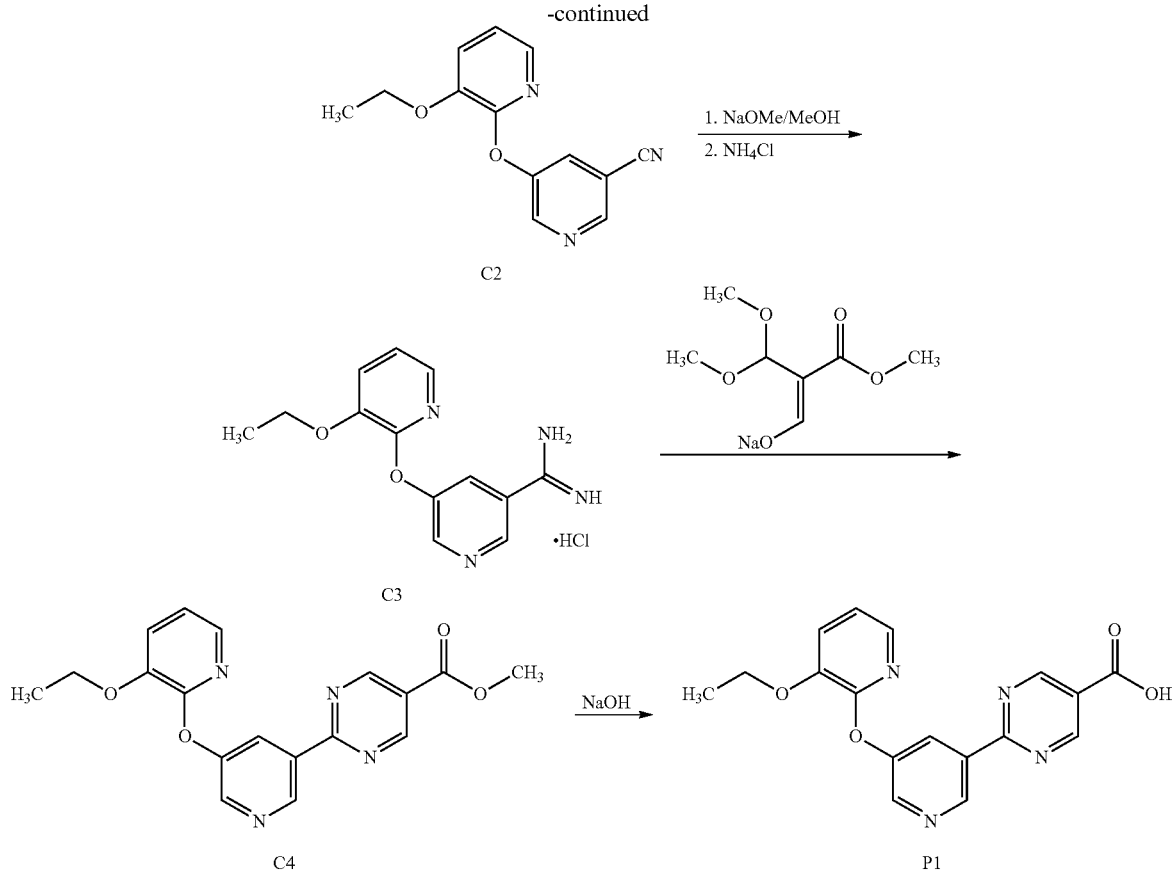

Step 1. Synthesis of 2-[(5-bromopyridin-3-yl)oxy]-3-ethoxypyridine (C1)

To a solution of 2-bromo-3-ethoxypyridine (841 g, 4.16 mol) in N,N-dimethylformamide (5.4 L) was added copper (I) bromide (538 g, 3.75 mol), followed by potassium carbonate (1.04 kg, 7.52 mol). The resulting mixture was stirred at 25° C., and 5-bromopyridin-3-ol (652 g, 3.75 mol) was added in one portion, whereupon the reaction mixture was heated at 120° C. for 16 hours. It was then cooled to 30° C., and slowly poured into a mixture of crushed ice (9.0 kg) and a 10% solution of ammonia in water (7.0 L). After the resulting suspension had been stirred for 1 hour, the precipitate was collected by filtration, and the filter cake was washed with water (3×5 L). It was then stirred for 1 hour in ethyl acetate (8 L) and filtered; the filtrate was washed with saturated aqueous sodium chloride solution (5 L), dried over sodium sulfate, filtered, and concentrated in vacuo. The residue was stirred in petroleum ether (2 L), and the solid was collected by filtration to provide C1. The filtrate was concentrated under reduced pressure, and the residue was triturated with petroleum ether (200 mL) to afford additional C1. The two batches were combined to provide C1 as a yellow solid. Yield: 835 g, 2.83 mol, 75%. $^1$H NMR (400 MHz, chloroform-d) δ 8.48 (d, J=1.9 Hz, 1H), 8.44 (d, J=2.4 Hz, 1H), 7.71 (dd, J=4.9, 1.5 Hz, 1H), 7.69 (dd, J=2.2, 2.1 Hz, 1H), 7.24 (dd, J=7.9, 1.5 Hz, 1H), 7.03 (dd, J=7.9, 4.9 Hz, 1H), 4.14 (q, J=7.0 Hz, 2H), 1.47 (t, J=7.0 Hz, 3H).

Step 2. Synthesis of 5-[(3-ethoxypyridin-2-yl)oxy]pyridine-3-carbonitrile (C2)

To a solution of C1 (324 g, 1.10 mol) in N,N-dimethylformamide (3.0 L) was added potassium ferrocyanide(II) trihydrate (697 g, 1.65 mol) in one portion, followed by water (300 mL). The resulting suspension was degassed under vacuum and then purged with nitrogen; this evacuation-purge cycle was carried out a total of four times. Palladium(II) acetate (4.94 g, 22.0 mmol) and 2-dicyclohexylphosphino-2',4',6'-triisopropylbiphenyl (XPhos; 18.7 g, 39.2 mmol) were then added, the evacuation-purge cycle was carried out five times, and the reaction mixture was heated at 105° C. for 18 hours. After the reaction mixture had been cooled to 50° C., it was filtered, and the filtrate was poured into ice water (3 L) and then stirred for approximately 1 hour. The resulting solid was collected by filtration, dissolved in ethyl acetate (1.5 L), washed with saturated aqueous sodium chloride solution (1 L), dried, filtered, and concentrated in vacuo to provide C2 (209 g) as a yellow solid. The aqueous filtrate from above was extracted with tert-butyl methyl ether (2×3 L), and the combined organic layers were washed with saturated aqueous sodium chloride solution (0.5 L), dried, filtered, and concentrated under reduced pressure to provide additional C2 (20 g). Combined yield: 229 g, 0.949 mol, 86%. $^1$H NMR (400 MHz, chloroform-d) δ 8.71 (d, J=2.7 Hz, 1H), 8.68 (d, J=1.8 Hz, 1H), 7.80 (dd, J=2.7, 1.7 Hz, 1H), 7.70 (dd, J=4.9, 1.5 Hz, 1H), 7.29-7.25 (m, 1H, assumed; partially obscured by solvent peak), 7.08 (dd, J=8.0, 4.9 Hz, 1H), 4.16 (q, J=7.0 Hz, 2H), 1.49 (t, J=7.0 Hz, 3H).

Step 3. Synthesis of 5-[(3-ethoxypyridin-2-yl)oxy]pyridine-3-carboximidamide, hydrochloride Salt (C3)

To a 0° C. to 5° C. suspension of C2 (180 g, 0.746 mol) in methanol (1.3 L) was added a solution of sodium methoxide in methanol (5 M; 30 mL, 150 mmol). Methanol (500 mL) was added to facilitate stirring, whereupon the reaction mixture was allowed to warm to room temperature (18° C.) and stirred for 20 hours. It was then cooled to −40° C. and treated with ammonium chloride (48.0 g, 897 mmol) in one portion, whereupon the mixture was warmed to room temperature (18° C.) and stirred for 40 hours. After concentration in vacuo to remove approximately half of the methanol, the resulting white precipitate (inorganic salt) was removed via filtration. The filtrate was diluted with ethyl acetate (400 mL) and concentrated under reduced pressure to a volume of approximately 400 mL. This ethyl acetate dilution-concentration procedure was repeated twice to effect exchange of methanol with ethyl acetate. Filtration of the resulting suspension afforded C3 as a white solid. Yield: 175 g, 0.594 mol, 80%. $^1$H NMR (400 MHz, DMSO-$d_6$) δ 8.82 (d, J=2 Hz, 1H), 8.77 (d, J=2.6 Hz, 1H), 8.05 (dd, J=2, 2 Hz, 1H), 7.66 (dd, J=4.9, 1.5 Hz, 1H), 7.57 (dd, J=7.9, 1.5 Hz, 1H), 7.18 (dd, J=7.9, 4.9 Hz, 1H), 4.17 (q, J=7.0 Hz, 2H), 1.37 (t, J=7.0 Hz, 3H).

Step 4. Synthesis of methyl 2-{5-[(3-ethoxypyridin-2-yl)oxy]pyridin-3-yl}pyrimidine-5-carboxylate (C4)

Sodium 2-(dimethoxymethyl)-3-methoxy-3-oxoprop-1-en-1-olate (201 g, 1.01 mol) was added in one portion to a solution of C3 (249 g, 0.845 mol) in methanol (1.75 L). The reaction mixture, a thick suspension, was stirred at 18° C. for 20 hours, whereupon the precipitate was collected by filtration to afford C4 as a white solid. Yield: 259 g, 0.735 mol, 87%. $^1$H NMR (400 MHz, DMSO-$d_6$) S 9.40 (d, J=1.8 Hz, 1H), 9.35 (s, 2H), 8.67 (d, J=2.7 Hz, 1H), 8.37 (dd, J=2.8, 1.8 Hz, 1H), 7.69 (dd, J=4.8, 1.5 Hz, 1H), 7.58 (dd, J=8.0, 1.5 Hz, 1H), 7.19 (dd, J=8.0, 4.8 Hz, 1H), 4.18 (q, J=7.0 Hz, 2H), 3.93 (s, 3H), 1.36 (t, J=7.0 Hz, 3H).

Step 5. Synthesis of 2-{5-[(3-ethoxypyridin-2-yl)oxy]pyridin-3-yl}pyrimidine-5-carboxylic Acid (P1)

This reaction was carried out in two parallel batches: C4 (321 g, 0.911 mol) was suspended in methanol (1.6 L), cooled in a bath of ice water, and treated in a drop-wise manner with sodium hydroxide solution (2 M; 684 mL, 1.37 mol). After completion of the addition, the reaction mixture was stirred at 14° C. for 16 hours, whereupon the two batches were combined. The resulting suspension was diluted with water (3.2 L), cooled with an ice water bath (approximately 5° C. to 10° C.), and adjusted to pH 3 to 4 by drop-wise addition of 1 M hydrochloric acid. The mixture was stirred at 14° C. for 2 hours, then filtered; the filter cake was washed sequentially with water (2×1 L) and ethyl acetate (1 L), affording P1 as a white solid. Combined yield: 557 g, 1.65 mol, 91%. LCMS m/z 338.9 [M+H]$^+$. $^1$H NMR (400 MHz, DMSO-$d_6$) δ 9.39 (d, J=1.8 Hz, 1H), 9.31 (s, 2H), 8.65 (d, J=2.7 Hz, 1H), 8.36 (dd, J=2.7, 1.8 Hz, 1H), 7.68 (dd, J=4.9, 1.5 Hz, 1H), 7.56 (dd, J=8.0, 1.5 Hz, 1H), 7.17 (dd, J=8.0, 4.8 Hz, 1H), 4.16 (q, J=7.0 Hz, 2H), 1.36 (t, J=7.0 Hz, 3H).

Preparation P1 material that was made using an analogous procedure as described above was further analyzed using powder X-ray diffraction analysis conducted on a Bruker AXS D8 Endeavor diffractometer equipped with a Cu radiation source (K-α average). The divergence slit was set at 15 mm continuous illumination. Diffracted radiation was detected by a PSD-Lynx Eye detector, with the detector PSD opening set at 3.00 degrees. The X-ray tube voltage and amperage were set to 40 kV and 40 mA respectively. Data was collected in the Theta-Theta goniometer at the Cu wavelength from 3.0 to 40.0 degrees 2-Theta using a step size of 0.01 degrees and a step time of 1.0 second. The antiscatter screen was set to a fixed distance of 1.5 mm. Samples were rotated at 15/min during collection. Samples were prepared by placing them in a silicon low background sample holder and rotated during collection.

Figure 6:
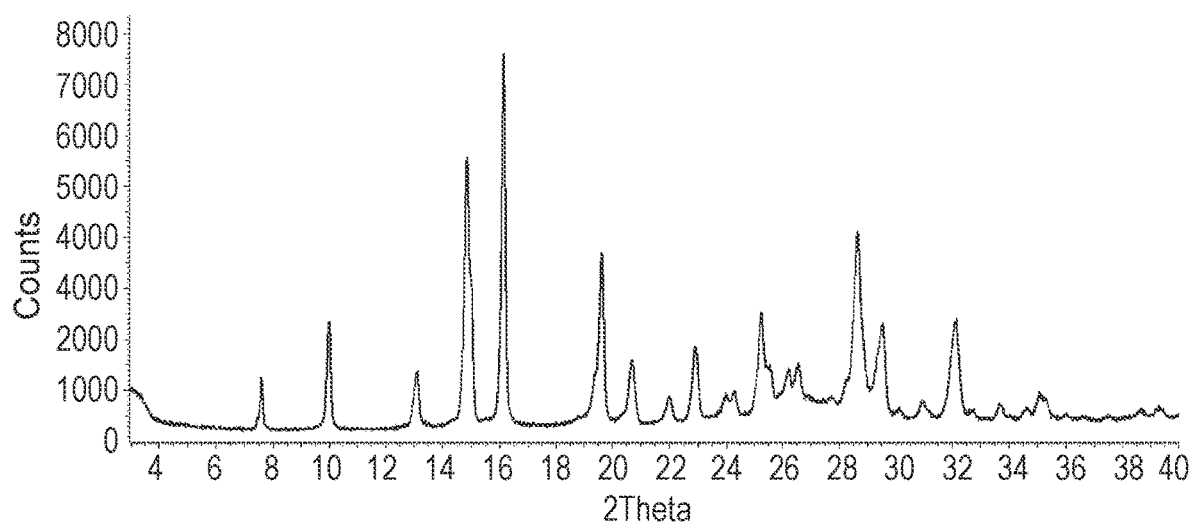
FIG. 6 is a characteristic x-ray powder diffraction pattern showing Preparation P1, Form 1 (Vertical Axis: Intensity (CPS); Horizontal Axis: Two theta (degrees)).
Figure 7:
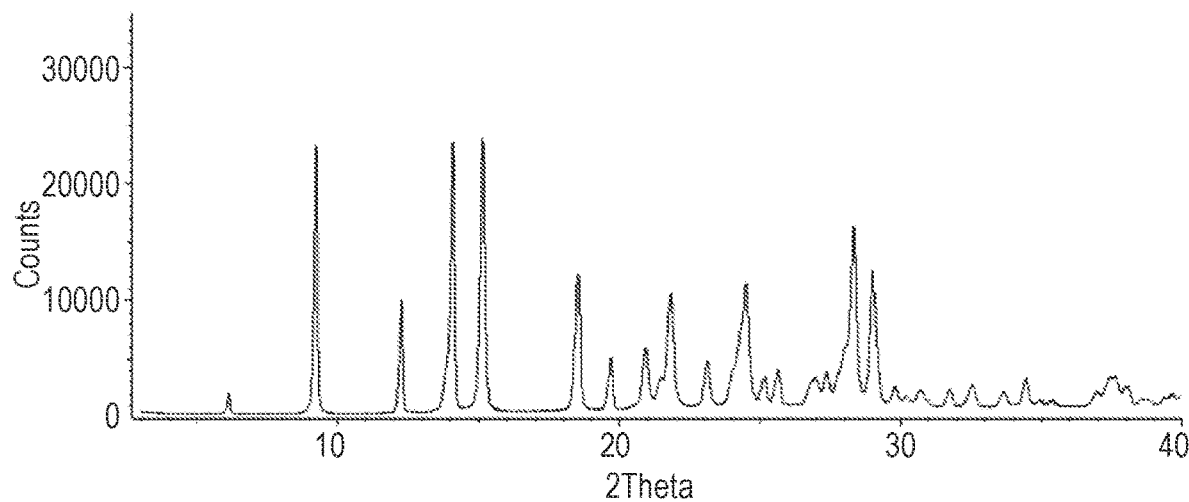
FIG. 7 is a characteristic x-ray powder diffraction pattern showing Preparation P1, Form 2 (Vertical Axis: Intensity (CPS); Horizontal Axis: Two theta (degrees)).
Figure 8:
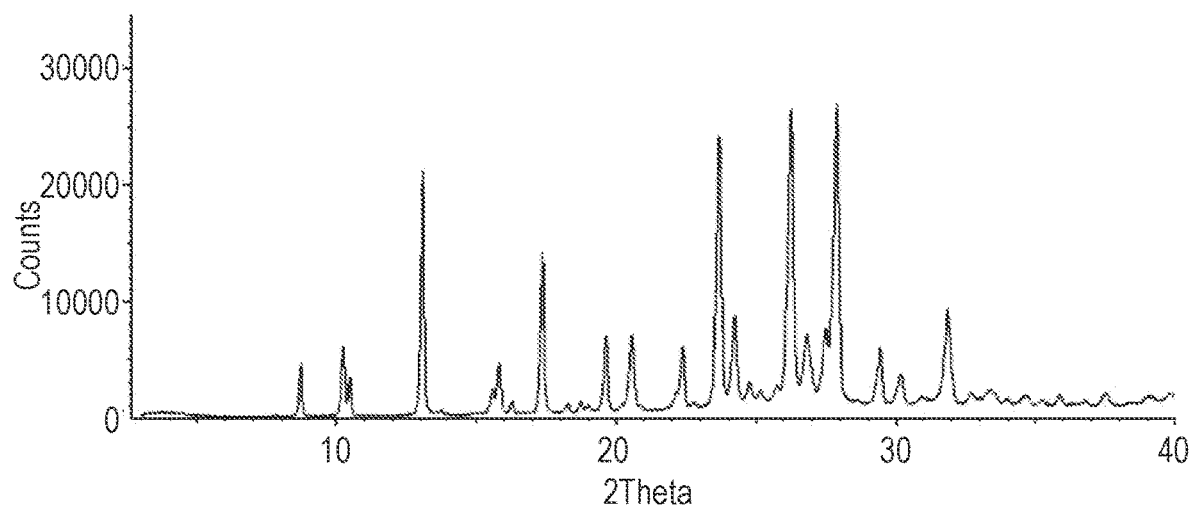
FIG. 8 is a characteristic x-ray powder diffraction pattern showing Preparation P1, Form 3 (Vertical Axis: Intensity (CPS); Horizontal Axis: Two theta (degrees)).

Data were collected using Bruker DIFFRAC Plus software and analysis was performed by EVA diffract plus software. The PXRD data file was not processed prior to peak searching. Using the peak search algorithm in the EVA software, peaks selected with a threshold value of 1 were used to make preliminary peak assignments. To ensure validity, adjustments were manually made; the output of automated assignments was visually checked, and peak positions were adjusted to the peak maximum. Peaks with relative intensity ≥3% were generally chosen. The peaks which were not resolved or were consistent with noise were not selected. A typical error associated with the peak position from PXRD stated in USP up to ±0.2° 2θ (USP-941). Some variation in relative peak heights is expected based on changes with crystal sizes and morphologies. Characteristic x-ray powder diffraction patterns is provided in FIG. 6. The PXRD data from this figure is further described below in Table AA. Using a similar procedure, two further batches of crystalline material of Preparation P1 were prepared and analysed as described above. The characteristic x-ray powder diffraction patterns for these batches are provided in FIGS. 7 and 8.

TABLE AA

| PXRD peaks for crystalline material of Preparation P1, Form 1 | |
|---|---|
| Angle 2Θ (°) | Relative intensity(%) |
| 7.6 | 14 |
| 10.0 | 29 |
| 13.1 | 15 |
| 14.9 | 72 |
| 16.2 | 100 |
| 19.6 | 46 |
| 20.7 | 17 |
| 22.0 | 7 |
| 22.9 | 19 |
| 24.0 | 4 |
| 24.3 | 4 |
| 25.3 | 27 |
| 25.6 | 13 |
| 26.2 | 12 |
| 26.6 | 13 |
| 28.7 | 49 |
| 29.6 | 25 |
| 32.1 | 26 |
| 35.1 | 4 |
| 35.3 | 4 |

TABLE AB

Key PXRD peaks to characterize crystalline
material of Preparation P1, Form 1
Preparation P1, Form 1
Angle 2Θ (°) ±0.2°

7.6, 10.0, 14.9, 16.2, 19.6

Alternate Synthesis of C2

5-[(3-Ethoxypyridin-2-yl)oxy]pyridine-3-carbonitrile (C2)

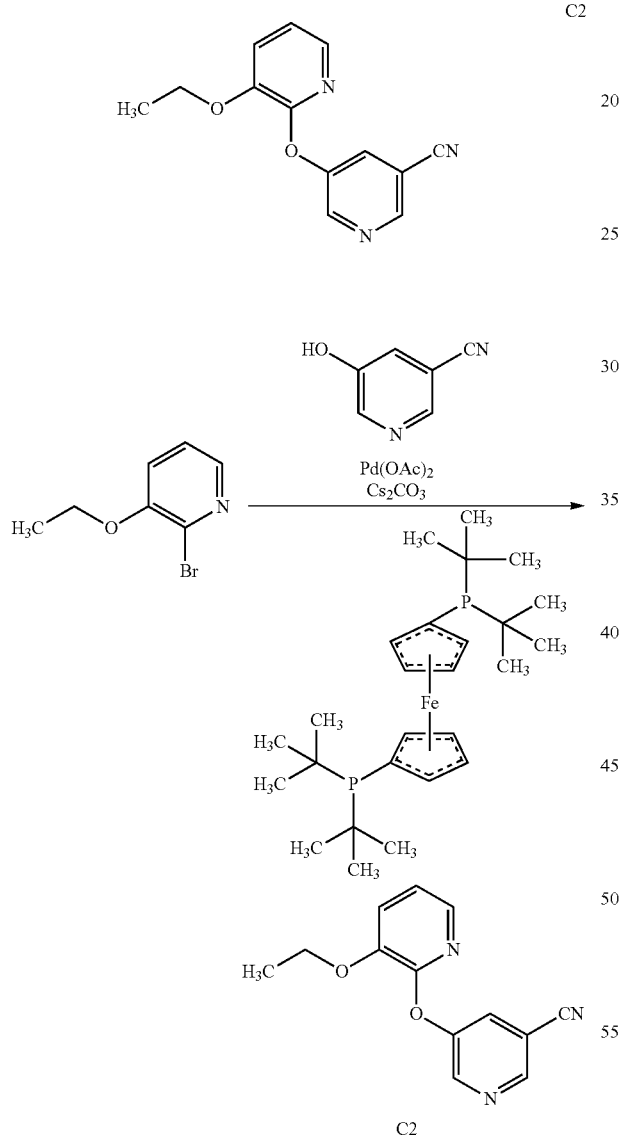

A solution of 2-bromo-3-ethoxypyridine (10.0 g, 49.5 mmol) in 1,4-dioxane (250 mL) was flushed with nitrogen for 2 minutes. 5-Hydroxypyridine-3-carbonitrile (6.54 g, 54.4 mmol), palladium(II) acetate (556 mg, 2.48 mmol), 1,1'-bis(di-tert-butylphosphino)ferrocene (1.41 g, 2.97 mmol), and cesium carbonate (32.3 g, 99.1 mmol) were then added, and the reaction mixture was stirred at 105° C. for 16 hours, whereupon it was combined with a similar reaction carried out using 2-bromo-3-ethoxypyridine (7.00 g, 34.6 mmol) and cooled to room temperature. After dilution with ethyl acetate (200 mL), the combined reaction mixtures were filtered through diatomaceous earth and concentrated to dryness in vacuo. The residue was diluted with ethyl acetate (200 mL), washed with saturated aqueous sodium chloride solution (2×200 mL), dried over sodium sulfate, filtered, and concentrated under reduced pressure. Silica gel chromatography (Gradient: 0% to 35% ethyl acetate in petroleum ether) afforded C2 as a yellow solid. Combined yield: 18.0 g, 74.6 mmol, 89%. LCMS m/z 242.1 [M+H]$^+$. $^1$H NMR (400 MHz, chloroform-d) δ 8.70 (d, J=2.7 Hz, 1H), 8.66 (d, J=1.8 Hz, 1H), 7.79 (dd, J=2.7, 1.8 Hz, 1H), 7.69 (dd, J=4.9, 1.5 Hz, 1H), 7.26 (dd, J=8.0, 1.5 Hz, 1H), 7.07 (dd, J=8.0, 4.9 Hz, 1H), 4.15 (q, J=7.0 Hz, 2H), 1.47 (t, J=7.0 Hz, 3H).

Preparation P2

2-{5-[(3-Ethoxy-5-fluoropyridin-2-yl)oxy]pyridin-3-yl}pyrimidine-5-carboxylic Acid (P2)

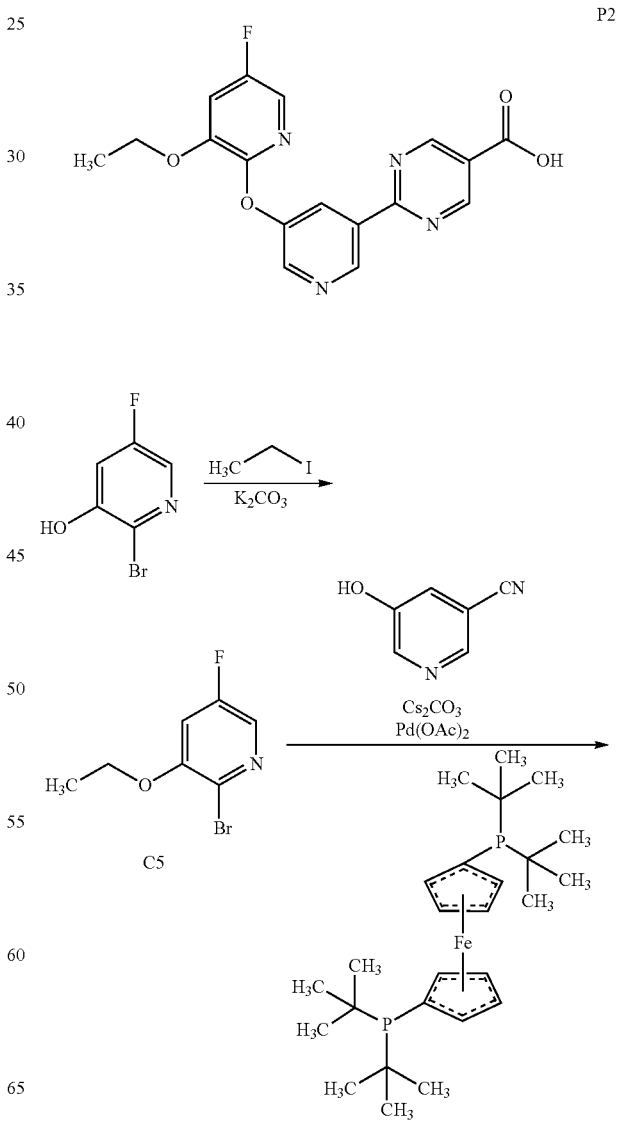

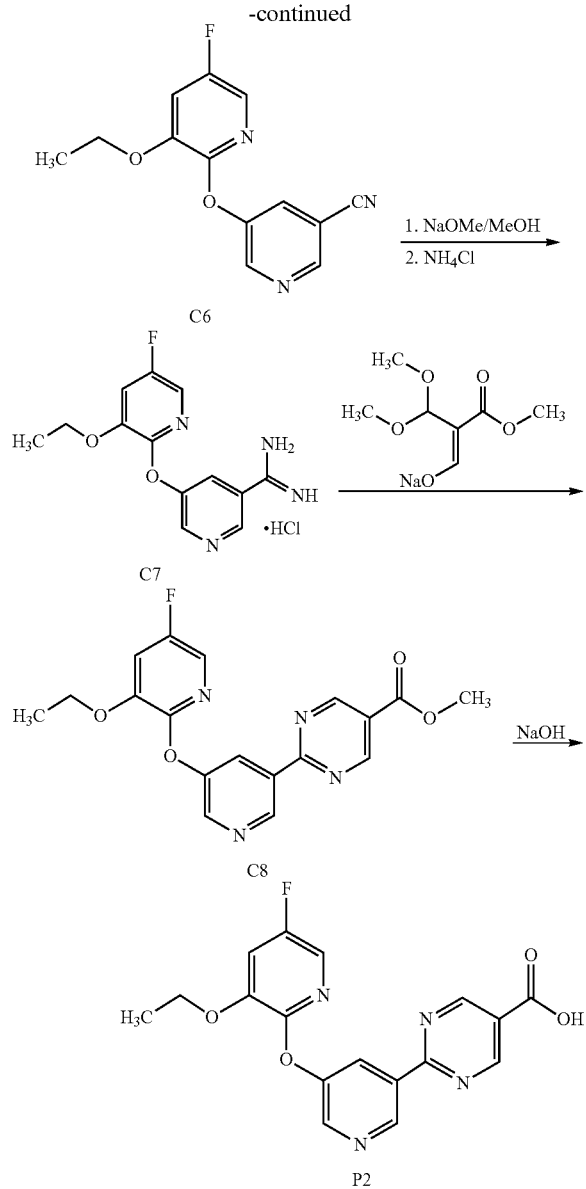

Step 1. Synthesis of 2-bromo-3-ethoxy-5-fluoropyridine (C5)

Potassium carbonate (697 g, 5.04 mol) was added to a solution of 2-bromo-5-fluoropyridin-3-ol (745 g, 3.88 mol) in N,N-dimethylformamide (4 L), whereupon the reaction vessel was evacuated and charged with nitrogen. This evacuation cycle was repeated twice, and the reaction mixture was then heated to 35° C. Iodoethane (372 mL, 4.65 mol) was added drop-wise over 30 minutes, and after the reaction mixture had been stirred at 35° C. for 16 hours, it was cooled to 25° C. and diluted with water (6 L). Stirring was continued for 15 minutes at 25° C.; the resulting solids were collected via filtration, and the filtrate was extracted with tert-butyl methyl ether (3×1.5 L). The combined organic layers were dried over sodium sulfate, filtered, and concentrated in vacuo. The residue was combined with the solid obtained from the first filtration, affording C5 as a brown solid. Yield: 756 g, 3.44 mol, 89%. $^1$H NMR (400 MHz, chloroform-d) δ 7.88 (d, J=2.5 Hz, 1H), 6.90 (dd, J=9.5, 2.5 Hz, 1H), 4.10 (q, J=7.0 Hz, 2H), 1.51 (t, J=7.0 Hz, 3H).

Step 2. Synthesis of 5-[(3-ethoxy-5-fluoropyridin-2-yl)oxy]pyridine-3-carbonitrile (C6)

This reaction was carried out in four parallel batches. 5-Hydroxypyridine-3-carbonitrile (112.6 g, 937.5 mmol) and cesium carbonate (389 g, 1.19 mol) were added in one portion to a solution of C5 (187.5 g, 852.1 mmol) in 1,4-dioxane (2.5 L). The reaction vessel was evacuated and charged with nitrogen. This evacuation cycle was repeated twice, whereupon palladium(II) acetate (9.57 g, 42.6 mmol) and 1,1'-bis(di-tert-butylphosphino)ferrocene (20.2 g, 42.6 mmol) were added into the reaction mixture. The evacuation-nitrogen cycles were repeated as above, and the reaction mixture was then stirred at 85° C. for 16 hours. Any reactions that were not complete after 16 hours were treated with additional palladium(II) acetate (9.57 g, 42.6 mmol) and 1,1'-bis(di-tert-butylphosphino)ferrocene (20.2 g, 42.6 mmol) and stirred at 85° C. for an additional 16 hours. At this point, the four reaction mixtures were combined and filtered; the filtrate was concentrated in vacuo, and the residue was dissolved in ethyl acetate (3 L), and then diluted with water (6 L). The resulting mixture was stirred at 25° C. for 15 minutes, whereupon the layers were separated, and the aqueous layer was extracted with ethyl acetate (3×1 L). After the combined organic layers had been washed with saturated aqueous sodium chloride solution (2×3 L), they were dried over sodium sulfate, filtered, and concentrated in vacuo. The residue was stirred in a mixture of tert-butyl methyl ether (1 L) and petroleum ether (2 L) at 25° C. for 20 minutes, and the resulting solid was collected via filtration to afford C6 (813 g) as a solid. The filtrate was concentrated in vacuo and subjected to chromatography on silica gel (Gradient: 0% to 30% ethyl acetate in petroleum ether) to provide additional C6 (52 g) as a brown solid. Combined yield: 865 g, 3.34 mol, 98%. LCMS m/z 259.8 [M+H]$^+$. $^1$H NMR (400 MHz, chloroform-d) δ 8.73-8.64 (m, 2H), 7.77 (br s, 1H), 7.56 (d, J=2.5 Hz, 1H), 7.06 (dd, J=9.0, 2.5 Hz, 1H), 4.14 (q, J=7.0 Hz, 2H), 1.50 (t, J=7.0 Hz, 3H).

Step 3. Synthesis of 5-[(3-ethoxy-5-fluoropyridin-2-yl)oxy]pyridine-3-carboximidamide, hydrochloride Salt (C7)

A solution of C6 (919 g, 3.54 mol) in ethyl acetate (3 L) was treated with activated carbon (approximately 200 g), and then stirred at 77° C. for 3 hours. After the resulting mixture had been filtered, the filtrate was concentrated in vacuo to provide C6 (894 g, 3.45 mol). The following reaction was then carried out in three parallel batches. Sodium methoxide (12.4 g, 230 mmol) was added to a 0° C. solution of C6 (298 g, 1.15 mol) in methanol (2 L). The reaction mixture was allowed to warm to 25° C. and was then stirred at 25° C. for 20 hours before being cooled to −40° C. and treated with ammonium chloride (67.6 g, 1.26 mol). At this point, the reaction mixture was allowed to warm to 25° C. and was stirred at 25° C. for 40 hours, whereupon the three batches were combined and concentrated in vacuo, affording C7 as a brown gum (1.15 kg). This material was used directly in the following step. LCMS m/z 276.8 [M+H]$^+$.

Step 4. Synthesis of methyl 2-{5-[(3-ethoxy-5-fluoropyridin-2-yl)oxy]pyridin-3-yl}pyrimidine-5-carboxylate (C8)

This reaction was carried out in three parallel batches. Sodium 2-(dimethoxymethyl)-3-methoxy-3-oxoprop-1-en- 1-olate (357 g, 1.80 mol) was added in one portion to a 25° C. solution of C7 (from the previous step; 383 g, mol) in methanol (2.5 L). After stirring at 25° C. for 16 hours, two of the three reactions were complete, as assessed by LCMS analysis. The third (incomplete) reaction was treated with additional sodium 2-(dimethoxymethyl)-3-methoxy-3-oxo-prop-1-en-1-olate (54.9 g, 277 mmol), and stirring was continued at 25° C. for 6 hours. At this point, the three batches were combined, diluted with water (8 L), and filtered. After the filter cake had been washed with water (2×2 L), it was stirred in a mixture of methanol (1 L) and tert-butyl methyl ether (1 L) for 3 hours at 25° C., whereupon the suspension was filtered to provide C8 as a brown solid. Yield: 1.0 kg, 2.7 mol, 78% over 2 steps. LCMS m/z 370.8 [M+H]$^+$. $^1$H NMR (400 MHz, chloroform-d) δ 9.54 (d, J=1.8 Hz, 1H), 9.32 (s, 2H), 8.63 (d, J=2.7 Hz, 1H), 8.55 (dd, J=2.7, 1.8 Hz, 1H), 7.57 (d, J=2.5 Hz, 1H), 7.05 (dd, J=9.2, 2.5 Hz, 1H), 4.16 (q, J=7.0 Hz, 2H), 4.00 (s, 3H), 1.51 (t, J=7.0 Hz, 3H).

Step 5. Synthesis of 2-{5-[(3-ethoxy-5-fluoropyridin-2-yl)oxy]pyridin-3-yl}pyrimidine-5-carboxylic Acid (P2)

A suspension of C8 (500 g, 1.35 mol) in methanol (2 L) was treated in a drop-wise manner with sodium hydroxide solution (2 M; 1.01 L, 2.02 mol). After completion of the addition, the reaction mixture was stirred at 25° C. for 16 hours, whereupon it was diluted with water (2 L). The pH was then adjusted to 3 to 4 by drop-wise addition of hydrochloric acid (1 M; approximately 1.5 L); the resulting mixture was stirred at 25° C. for 1 hour, and the solid was collected by filtration. The filter cake was washed with water (2×1 L) to provide P2 as an off-white solid. Yield: 405 g, 1.14 mol, 84%. LCMS m/z 356.8 [M+H]$^+$. $^1$H NMR (400 MHz, DMSO-d$_6$) δ 9.39 (d, J=1.7 Hz, 1H), 9.31 (s, 2H), 8.65 (d, J=2.7 Hz, 1H), 8.37-8.34 (m, 1H), 7.71 (d, component of AB quartet, J=2.6 Hz, 1H), 7.68 (dd, component of ABX system, J=9.8, 2.6 Hz, 1H), 4.19 (q, J=7.0 Hz, 2H), 1.36 (t, J=7.0 Hz, 3H).

Preparation P3 tert-Butyl (3S,5S)-3-amino-5-fluoropiperidine-1-carboxylate (P3)

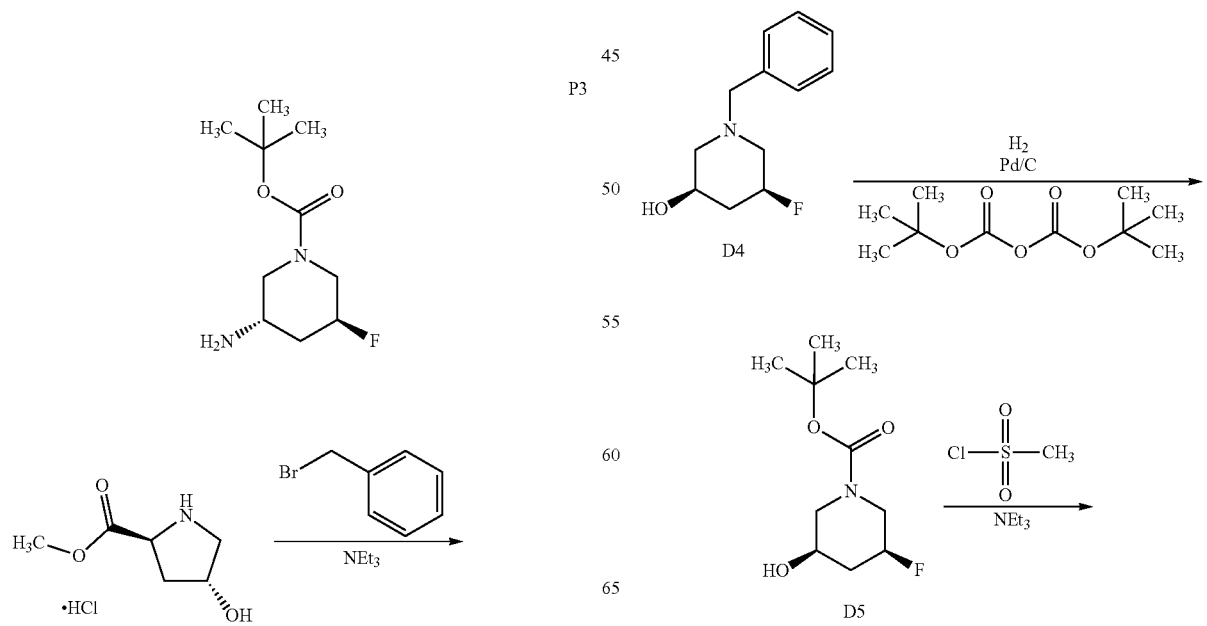

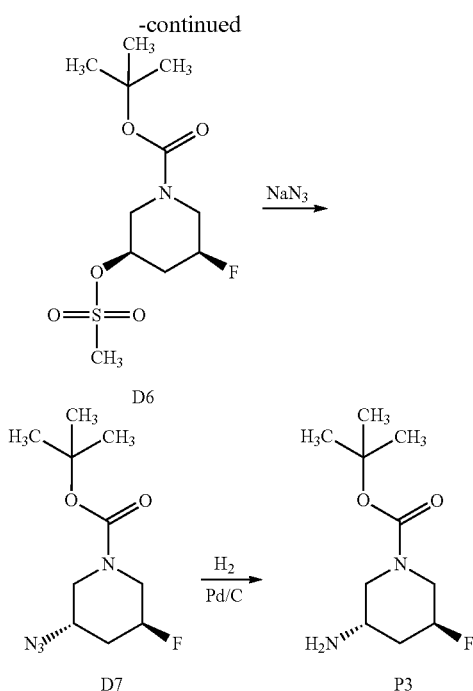

This entire sequence was carried out on large scale. In general, before reactions, as well as after addition of reagents, reactors were evacuated to ≤−0.07 MPa and then filled with nitrogen to normal pressure. This process was generally repeated 3 times, and then oxygen content was assessed to ensure that it was ≤1.0%. For the processes of quenching, extraction, and washing of organic layers, mixtures were generally stirred for 15 to 60 minutes and then allowed to settle for 15 to 60 minutes before separation of layers.

Step 1. Synthesis of methyl (2S,4R)-1-benzyl-4-hydroxypyrrolidine-2-carboxylate (D1)

Triethylamine (93.55 kg, 924.5 mol) was charged into a 15° C. to 25° C. mixture of dichloromethane (968 kg) and methyl (2S,4R)-4-hydroxypyrrolidine-2-carboxylate, hydrochloride salt (56.05 kg, 308.6 mol) at a reference rate of 80 to 120 kg/hour. After the mixture had been stirred for 10 to 20 minutes, benzyl bromide (79.00 kg, 461.9 mol) was added at a reference rate of 20 to 30 kg/hour. The reaction mixture was stirred at 15° C. to 25° C.; after 12 hours, it was sampled every 2 to 6 hours for analysis via HPLC, until the area percent of the starting material was less than 2% (HPLC conditions. Column: Waters XBridge BEH C18, 4.6×150 mm, 3.5 μm; Mobile phase A: water containing 0.1% heptafluorobutyric acid; Mobile phase B: acetonitrile; Gradient: 10% B for 3 minutes, then 10% to 40% B over 10 minutes, then 40% to 90% B over 5 minutes; Flow rate: 1.0 mL/minute). Typical retention time of methyl (2S,4R)-4-hydroxypyrrolidine-2-carboxylate: 3.8 minutes.

Water (280 kg) was then added to the reactor at a reference rate of 100 to 150 kg/hour and 15° C. to 25° C. The aqueous layer was extracted once with dichloromethane (372 kg, 281 L, 5 volumes); the combined organic layers were washed with a solution of sodium chloride (93.0 kg) in water (280 kg) and then concentrated at −0.08 MPa to a volume of 100 to 150 L while the temperature was maintained below 35° C. Tetrahydrofuran (497 kg) was charged into the resulting mixture in two portions. The mixture was again concentrated at −0.08 MPa to a volume of 100 to 150 L while the temperature was maintained below 35° C. Karl Fischer analysis and sampling for residual dichloromethane were carried out to ensure that water content was ≤0.30% and residual dichloromethane was ≤4%. The resulting solution was adjusted to 15° C. to 30° C., affording a yellow solution containing D1. Yield: 136.8 kg of solution, containing D1 (69.14 kg, 293.9 mol, 95%). HPLC purity: 90% (HPLC conditions. Column: Waters XBridge BEH C18, 4.6×150 mm, 3.5 μm; Mobile phase A: 10 mM ammonium acetate in water; Mobile phase B: acetonitrile; Gradient: 20% to 95% B over 10 minutes; Flow rate: 1.0 mL/minute). Retention time of D1: 4.72 minutes. $^1$H NMR (401 MHz, chloroform-d) δ 7.34-7.21 (m, 5H), 4.48-4.39 (m, 1H), 3.90 (d, J=12.9 Hz, 1H), 3.65 (d, J=12.9 Hz, 1H), 3.65 (s, 3H), 3.59 (dd, J=7.9, 7.8 Hz, 1H), 3.32 (dd, J=10.1, 5.7 Hz, 1H), 2.57 (br s, 1H), 2.45 (dd, J=10.2, 4.1 Hz, 1H), 2.24 (ddd, J=13.2, 7.7, 6.9 Hz, 1H), 2.07 (ddd, J=13.3, 8.0, 3.2 Hz, 1H).

Step 2. Synthesis of methyl (2S,4S)-1-benzyl-4-fluoropyrrolidine-2-carboxylate (D2)

A solution of D1 in tetrahydrofuran (128.4 kg, containing 64.90 kg, 275.8 mol of D1) was added to a reactor containing tetrahydrofuran (575 kg) at 15° C. to 25° C. Triethylamine (114.2 kg, 1129 mol) was then added at a reference addition rate of 35 to 45 kg/hour. Triethylamine trihydrofluoride (66.70 kg, 413.7 mol) was charged into the mixture, followed by nonafluorobutane-1-sulfonyl fluoride (128.0 kg, 423.7 mol) at a reference rate of 60 to 80 kg/hour, and the reaction was allowed to proceed at 15° C. to 25° C. After 4 hours, the reaction mixture was sampled every 2 to 6 hours for analysis via HPLC, until the area percent of D1 was less than 1% (HPLC conditions. Column: Waters XBridge BEH C18, 4.6×150 mm, 3.5 μm; Mobile phase A: 10 mM ammonium acetate in water; Mobile phase B: acetonitrile; Gradient: 20% to 95% B over 10 minutes; Flow rate: 1.0 mL/minute). Typical retention time of D1: 5.0 minutes.

The mixture was then cooled to 10° C. to 15° C., and water (325 kg) was added at a reference rate of 100 to 120 kg/hour, followed by tert-butyl methyl ether (240.5 kg) at 15° C. to 25° C. The organic phase was washed twice with a solution of sodium bicarbonate (18.2 kg, 217 mol) in water (198 kg), and then washed twice with a solution of sodium chloride (47.2 kg) in water (130 kg). It was then concentrated at ≤−0.08 MPa to a volume of 150 to 200 L while the temperature was maintained below 45° C. After the resulting mixture had been adjusted to 20° C. to 30° C., tert-butyl methyl ether (123 kg, 166 L, 2.5 volumes) and n-heptane (112 kg, 163 L, 2.5 volumes) were added. The resulting mixture was filtered through a silica gel column (112 kg of silica gel), until nearly all of the material had been filtered. The reactor was then rinsed with tert-butyl methyl ether (481 kg, 10 volumes) and n-heptane (444 kg, 10 volumes) at 20° C. to 30° C., and this rinsing liquor was also filtered through the silica gel column. The combined filtrates were eluted through a fresh column containing silica gel (40 kg), and the eluent was concentrated at ≤−0.08 MPa to a volume of 80 to 100 L while the temperature was maintained below 45° C. The resulting solution was adjusted to 20° C. to 30° C., affording a yellow solution containing D2. Yield: 104.3 kg of solution, containing D2 (52.64 kg, 221.8 mol, 80%). HPLC purity: 83% (HPLC conditions. Column: Waters XBridge BEH C18, 4.6×150 mm, 3.5 μm; Mobile phase A: 10 mM ammonium acetate in water; Mobile phase B:

acetonitrile; Gradient: 20% to 95% B over 10 minutes; Flow rate: 1.0 mL/minute). Retention time for D2: 7.34 minutes. $^1$H NMR (401 MHz, chloroform-d) δ 7.37-7.22 (m, 5H), 5.10 (br ddd, J=54.8, 5, 5 Hz, 1H), 4.03 (d, J=13.0 Hz, 1H), 3.70 (s, 3H), 3.59 (d, J=13.0 Hz, 1H), 3.34-3.21 (m, 2H), 2.65-2.42 (m, 2H), 2.29 (br ddd, J=29.8, 14.8, 6.3 Hz, 1H).

Step 3. Synthesis of [(2S,4S)-1-benzyl-4-fluoropyrrolidin-2-yl]methanol (D3)

Tetrahydrofuran (352 kg) was added to lithium aluminum hydride (8.20 kg, 216 mol) at 15° C. to 25° C., under nitrogen. After completion of the addition, the mixture was stirred for 10 to 15 minutes, and nitrogen was bubbled in from the lower port of the reactor for 3 to 5 minutes. The mixture was adjusted to 8° C. to 15° C., and then a solution of D2 in tetrahydrofuran (99.10 kg, containing 50.02 kg, 210.8 mol of D2) was added portion-wise at a reference rate of 35 to 45 kg/hour at 8° C. to 15° C. After one-third of the substrate had been added, the reaction mixture was stirred for 0.5 to 1 hour, and then sampled for analysis. Additional material was not added until ≤10% of the D2 charge remained. Upon completion of the entire D2 addition, the reaction was allowed to proceed at 8° C. to 15° C.; after 1 hour, it was sampled for HPLC analysis every 1 to 3 hours until ≤2% of D2 was observed (HPLC conditions. Column: Waters XBridge BEH C18, 4.6×150 mm, 3.5 μm; Mobile phase A: 10 mM ammonium acetate in water; Mobile phase B: acetonitrile; Gradient: 20% to 95% B over 10 minutes; Flow rate: 1.0 mL/minute). Typical retention time for D2: 7.5 minutes.

The reaction was then quenched via addition of a mixture of water (8.00 kg) and tetrahydrofuran (44.5 kg); this was added at 0° C. to 20° C. at a reference rate of 6 to 8 kg/hour. A solution of sodium hydroxide (1.40 kg, 35 mol) in water (30.0 kg) was then charged into the mixture at 10° C. to 25° C., at a reference rate of 10 to 20 kg/hour. After this addition, the mixture was stirred for 0.5 to 1 hour. Nitrogen was then bubbled into the mixture from the lower port of the reactor for 4 to 6 hours at 15° C. to 25° C. The mixture was filtered, and the collected solids were stirred with tetrahydrofuran (317 kg) at 15° C. to 25° C. for 1 to 2 hours; this mixture was then filtered. The combined filtrates were concentrated to 1 to 1.2 volumes, at ≤−0.08 MPa, while the temperature was maintained below 45° C. 2-Methyltetrahydrofuran (388 kg) was charged into the mixture in portions, while the temperature was maintained below 45° C. After each addition, the mixture was stirred for 5 to 10 minutes, and then concentrated as above to 1 to 1.2 volumes. Sampling was carried out to ensure that residual tetrahydrofuran was ≤2%, and water content (by Karl Fischer analysis) was ≤1%. The resulting mixture was adjusted to 15° C. to 25° C. and treated with 2-methyltetrahydrofuran (43.0 kg); stirring provided a yellow solution containing D3. Yield: 102.7 kg of solution, containing D3 (41.05 kg, 196.2 mmol, 93%). HPLC purity: 90% (HPLC conditions. Column: Waters XBridge BEH C18, 4.6×150 mm, 3.5 μm; Mobile phase A: 10 mM ammonium acetate in water; Mobile phase B: acetonitrile; Gradient: 20% to 95% B over 10 minutes; Flow rate: 1.0 mL/minute). Retention time for D3: 5.38 minutes. $^1$H NMR (401 MHz, chloroform-d), characteristic peaks: δ 7.37-7.23 (m, 5H), 5.05 (br ddd, J=54.5, 4.7, 4.5 Hz, 1H), 4.04 (d, J=13.3 Hz, 1H), 3.54-3.45 (m, 1H), 3.33 (d, J=13.3 Hz, 1H), 3.23 (br dd, J=18.5, 11.7 Hz, 1H), 2.83-2.75 (m, 1H), 2.63 (br d, J=9.2 Hz, 1H), 2.49-2.10 (m, 3H).

Step 4. Synthesis of (3R,5S)-1-benzyl-5-fluoropiperidin-3-ol (D4)

A solution of D3 in 2-methyltetrahydrofuran (102.6 kg, containing 41.03 kg, 196.1 mol of D3) was added to 2-methyltetrahydrofuran (160 kg) at 15° C. to 25° C. Trifluoroacetic anhydride (42.20 kg, 200.9 mol) was then added at a reference rate of 35 to 45 kg/hour, followed by triethylamine (61.1 kg, 604 mol) at a reference rate of 35 to 45 kg/hour. The reaction mixture was maintained at 15° C. to 25° C. for 1 hour, then heated to 77° C. to 82° C. After 12 hours, the reaction was sampled every 1 to 12 hours for HPLC analysis, until the area percent of D3 was ≤3% (HPLC conditions. Column: Waters XBridge BEH C18, 4.6×150 mm, 3.5 μm; Mobile phase A: 10 mM ammonium acetate in water; Mobile phase B: acetonitrile; Gradient: 20% to 95% B over 10 minutes; Flow rate: 1.0 mL/minute). Typical retention time for D3: 5.8 minutes.

At that time, the reaction mixture was cooled to 10° C. to 20° C. and treated with a solution of sodium hydroxide (3.30 kg, 82 mol) in water (41.1 kg) at a reference rate of 34 to 45 kg/hour, while the temperature was maintained between 10° C. to 30° C. After completion of the addition, the mixture was stirred for 1 hour, whereupon it was washed with a solution of sodium chloride (23.1 kg) in water (82.2 kg) at 15° C. to 30° C. The aqueous layer was extracted once with tert-butyl methyl ether (150 kg, 203 L, 5 volumes) at 15° C. to 30° C., and the combined organic layers were concentrated at ≤−0.08 MPa to 1 to 1.2 volumes, while the temperature was maintained below 45° C. The mixture was washed twice with water (162 kg) at 15° C. to 30° C., and the organic phase was sampled for triethylamine to ensure that the triethylamine level was ≤3%. It was then concentrated at ≤−0.08 MPa to a volume of 1 to 1.2 volumes, while the temperature was maintained below 45° C. Tetrahydrofuran (110 kg) was added, and the resulting mixture was again concentrated at ≤−0.08 MPa to a volume of 1 to 1.2 volumes, while the temperature was maintained below 45° C. The resulting material was cooled to 20° C. to 30° C., affording a dark brown solution containing D4. Yield: 153.5 kg of solution, containing D4 (36.50 kg, 174.4 mmol, 89%). HPLC purity: 85% (HPLC conditions. Column: Waters XBridge BEH C18, 4.6×150 mm, 3.5 μm; Mobile phase A: 10 mM ammonium acetate in water; Mobile phase B: acetonitrile; Gradient: 20% to 95% B over 10 minutes; Flow rate: 1.0 mL/minute). Retention time for D4: 5.88 minutes. $^1$H NMR (401 MHz, chloroform-d) δ 7.36-7.23 (m, 5H), 4.84-4.66 (m, 1H), 3.90-3.81 (m, 1H), 3.62-3.59 (m, 2H), 2.92-2.76 (m, 2H), 2.69 (dd, J=11.5, 5.0 Hz, 1H), 2.54-2.39 (m, 2H), 2.10-1.98 (m, 1H), 1.95-1.78 (m, 1H).

Step 5. Synthesis of tert-butyl (3S,5R)-3-fluoro-5-hydroxypiperidine-1-carboxylate (D5)

A mixture of D4 in tetrahydrofuran (containing 30.03 kg, 143.5 mol of D4), tetrahydrofuran (218 kg), and di-tert-butyl dicarbonate (47.10 kg, 215.8 mol), at 15° C. to 30° C., was purged with nitrogen via a subsurface pipe to 0.2 to 0.3 MPa, then vented to 0.02 to 0.05 MPa. This purge and vent procedure was repeated between 5 and 8 times. Palladium on charcoal (10%, 3.00 kg) was charged into the reactor at 15° C. to 30° C., and the solid addition funnel was then rinsed with water (0.26 kg). The reaction mixture was purged with nitrogen via subsurface pipe to 0.1 to 0.2 MPa, then vented to 0.02 to 0.05 MPa at 15° C. to 30° C.; this purge and vent procedure was repeated between 5 and 8 times. An identical purge-vent protocol was then carried out using hydrogen.

After the final hydrogen exchange, the pressure was increased to 0.1 to 0.2 MPa with hydrogen. The reaction mixture was then exchanged with nitrogen twice every 1 to 3 hours, and purged with hydrogen via subsurface pipe to 0.1 to 0.2 MPa, followed by venting to 0.02 to 0.05 MPa. After the exchange, the hydrogen pressure was increased to 0.1 to 0.2 MPa, and the reaction mixture was maintained at 20° C. to 30° C. After 8 hours, the reaction was sampled for HPLC analysis every 1 to 12 hours, until the level of D4 was ≤1.0% (HPLC conditions. Column: Waters XSelect Phenyl-Hexyl, 4.6×150 mm, 3.5 μm; Mobile phase A: water containing 0.1% trifluoroacetic acid; Mobile phase B: acetonitrile containing 0.1% trifluoroacetic acid; Gradient: 5% to 35% B over 15 minutes; Flow rate: 1.0 mL/minute).

The mixture was then purged with nitrogen via subsurface pipe to 0.2 to 0.3 MPa, and vented to 0.02 to 0.05 MPa at 15° C. to 30° C.; this cycle was repeated not less than 9 times. The reaction mixture was passed through a stainless steel nutsche filter at 20° C. to 30° C., and the filter cake was rinsed with tetrahydrofuran (26.6 kg, 29.9 L, 1 volume); the combined filtrates were passed through a filter loaded with silica gel (15.1 kg), and the silica filter cake was rinsed with tetrahydrofuran (52.7 kg, 59.3 L, 2 volumes). These combined filtrates were passed through an in-line filter at 15° C. to 30° C. and concentrated at ≤−0.08 MPa to a volume of 1.1 to 1.4 volumes, while the temperature was maintained below 45° C. The resulting mixture was treated with n-heptane (102 kg) at 15° C. to 45° C. and stirred for 10 minutes, whereupon the mixture was sampled to ensure that residual tetrahydrofuran was <8%. Tetrahydrofuran (6.90 kg) and n-heptane (101 kg) were added at 15° C. to 45° C., and the mixture was heated to 50° C. to 55° C., then cooled to 18° C. to 25° C. and stirred for 1 hour. Seed crystals of D5 (0.06 kg; see origin below) were charged into the mixture, which was then was stirred for 1 to 2 hours while the temperature was maintained at 18° C. to 25° C. Stirring was continued at 15° C. to 20° C. for 8 to 12 hours for crystallization. Nitrogen was bubbled in from the lower port of the reactor every 2 to 3 hours to effect concentration. The mixture was then filtered, using a stainless steel nutsche filter; the filter cake was rinsed with a mixture of n-heptane (20.4 kg) and tetrahydrofuran (0.81 kg) and then dried at 20° C. to 30° C. until sampling indicated residual tetrahydrofuran ≤720 ppm and residual n-heptane ≤5000 ppm. Product D5 was obtained as an off-white solid. Yield: 12.15 kg, 97.5% by assay; corrected weight: 11.84 kg, 54.00 mol. Additional material from mother liquor recovery: 5.17 kg, 23.6 mmol. Combined yield: 54%. HPLC purity: 94% (HPLC conditions. Column: Waters XSelect Phenyl-Hexyl, 4.6×150 mm, 3.5 μm; Mobile phase A: water containing 0.1% trifluoroacetic acid; Mobile phase B: acetonitrile containing 0.1% trifluoroacetic acid; Gradient: 5% to 35% B over 15 minutes; Flow rate: 1.0 mL/minute). Retention time for D5: 12.58 minutes. $^1$H NMR (401 MHz, chloroform-d) δ 4.69 (br d, $J_{HF}$=47.2 Hz, 1H), 3.86-3.76 (m, 1H), 3.62-3.35 (m, 3H), 2.64-2.44 (m, 1H), 2.18-1.92 (m, 2H), 1.46 (s, 9H).

Preparation of seed crystal of D5: A smaller-scale hydrogenation reaction of D4 was carried out as above; after removal of the palladium on carbon, the resulting solution of D5 in tetrahydrofuran was concentrated to approximately 1 to 1.2 volumes (based on the quantity of D4 used). The resulting mixture was treated with tetrahydrofuran (0.2 volumes) and n-heptane (15 volumes), heated to 50° C. to 55° C., and allowed to cool to 15° C. to 20° C. After the suspension had been stirred for 6 to 8 hours, it was filtered to afford D5 as a solid; this material was used as the seed crystals.

Step 6. Synthesis of tert-butyl (3S,5R)-3-fluoro-5-[(methylsulfonyl)oxy]piperidine-1-carboxylate (D6)

Dichloromethane (229 kg) was charged into a reactor at 15° C. to 25° C., followed by D5 (17.40 kg; corrected from assay results: 16.96 kg, 77.35 mol); nitrogen was then bubbled in through the lower port. Triethylamine (9.80 kg, 96.8 mol) was added at 15° C. to 25° C., whereupon the reaction mixture was cooled to 0° C. to 5° C. While the mixture was maintained at 0° C. to 10° C., methanesulfonyl chloride (10.18 kg, 88.88 mol) was added, and the reaction was allowed to proceed at 0° C. to 10° C. After 1 hour, it was sampled every 1 to 3 hours until the area percent of D5 was less than 1% (HPLC conditions. Column: Waters XBridge BEH C18, 4.6×150 mm, 3.5 μm; Mobile phase A: 10 mM ammonium acetate in water; Mobile phase B: acetonitrile; Gradient: 30% to 95% B over 10 minutes; Flow rate: 1.0 mL/minute). Typical retention time for D5: 4.31 minutes.

At that point, water (52.0 kg) was charged into the mixture at 0° C. to 5° C., at a reference rate of 20 to 38 kg/hour. The aqueous phase of the resulting mixture was extracted with dichloromethane (70.4 kg, 53.1 L, 3 volumes) at 0° C. to 10° C., and the combined organic layers were washed with a solution of sodium chloride (4.30 kg) in water (17.4 kg) at 0° C. to 15° C., and subsequently concentrated at ≤−0.09 MPa to 2 to 3 volumes while the temperature was maintained below 30° C. The residue was diluted with tert-butyl methyl ether (128 kg) in portions at 0° C. to 30° C., and then the mixture was concentrated at ≤−0.09 MPa to 2 to 3 volumes while the temperature was maintained below 30° C. tert-Butyl methyl ether (65.0 kg) was again charged into the mixture portion-wise at 0° C. to 30° C., and the mixture was again concentrated at ≤−0.09 MPa to 2 to 3 volumes while the temperature was maintained below 30° C. This protocol was repeated until analysis for dichloromethane provided a residual dichloromethane level of ≤2%. The mixture was then heated to 35° C. to 40° C., and n-heptane (116 kg) was added at a reference rate of 40 to 60 kg/hour, whereupon the mixture was slowly cooled to 0° C. to 10° C. at a reference rate of 10° C. to 15° C./hour. It was then stirred at 0° C. to 10° C. for 2 hours. Filtration provided a filter cake, which was rinsed with n-heptane (22.5 kg), and then dried at 35° C. to 40° C. under a flow of nitrogen. The resulting solid was mixed with tert-butyl methyl ether (59.4 kg) at 15° C. to 30° C., and then heated to 35° C. to 40° C. n-Heptane (119 kg) was added at 35° C. to 40° C., at a reference rate of 40 to 60 kg/hour, and the resulting mixture was slowly cooled to 0° C. to 10° C., at a reference rate of 10° C. to 15° C./hour. After the mixture had been stirred at 0° C. to 10° C. for 2 hours, it was filtered, and the filter cake was rinsed with n-heptane (23.6 kg). The collected solid was dried at 35° C. to 40° C. until residual tert-butyl methyl ether was ≤5000 ppm, residual n-heptane was ≤5000 ppm, and Karl Fischer analysis revealed water content of ≤0.1%. The resulting material was cooled to 15° C. to 30° C., affording D6 as a white solid. Yield: 19.35 kg, 98.3% by assay; corrected weight: 19.02 kg, 63.97 mol, 83%. HPLC purity: 99% (HPLC conditions. Column: Waters XBridge BEH C18, 4.6×150 mm, 3.5 μm; Mobile phase A: 10 mM ammonium acetate in water; Mobile phase B: acetonitrile; Gradient: 30% to 95% B over 10 minutes; Flow rate: 1.0 mL/minute). Retention time for D6: 4.98 minutes. $^1$H NMR (401 MHz, chloroform-d) δ 4.79-4.52 (m, 2H), 3.72-3.53 (m, 4H), 3.06 (s, 3H), 2.36-2.11 (m, 2H), 1.46 (s, 9H).

Step 7. Synthesis of tert-butyl (3S,5S)-3-azido-5-fluoropiperidine-1-carboxylate (D7)

N,N-Dimethylformamide (174 kg) and D6 (18.45 kg; corrected for assay 18.14 kg, 61.01 mol) were charged into a reactor and stirred at 15° C. to 30° C. until a solution was obtained, whereupon sodium azide (6.05 kg, 93.1 mol) was added at 15° C. to 30° C. The reaction mixture was heated to 78° C. to 88° C., at a reference rate of 20° C. to 35° C./hour, and then allowed to react at 78° C. to 88° C. After 6 to 12 hours, the reaction mixture was sampled every 2 to 8 hours for HPLC analysis, until the area percent of D6 was less than 0.5% (HPLC conditions. Column: Waters XBridge BEH C18, 4.6×150 mm, 3.5 μm; Mobile phase A: water containing 0.1% ammonium acetate; Mobile phase B: acetonitrile; Gradient: 20% to 95% B over 10 minutes; Flow rate: 1.0 mL/minute). Typical retention time for D6: 6.4 minutes.

After the mixture had been cooled to 10° C. to 20° C., tert-butyl methyl ether (68.7 kg) and water (185 kg) were added, at a reference rate of 35 to 85 kg/hour, and stirring was continued for 10 to 20 minutes. The mixture was filtered, and the aqueous layer of the filtrate was extracted with tert-butyl methyl ether (2×69 kg, 93 L, 5 volumes). The combined organic layers were washed with water (2×56 kg, 56 L, 3 volumes) to afford D7 as a light yellow solution in tert-butyl methyl ether. Yield: 185.4 kg; solution in tert-butyl methyl ether, assumed to contain 14.90 kg, 61.01 mol of D7, 100%. HPLC purity: 80% (HPLC conditions. Column: Waters XBridge BEH C18, 4.6×150 mm, 3.5 μm; Mobile phase A: water containing 0.1% ammonium acetate; Mobile phase B: acetonitrile; Gradient: 20% to 95% B over 10 minutes; Flow rate: 1.0 mL/minute). Retention time for D7: 8.37 minutes.

Step 8. Synthesis of tert-butyl (3S,5S)-3-amino-5-fluoropiperidine-1-carboxylate (P3)

Methanol (30.2 kg) and D7 (185.4 kg of the tert-butyl methyl ether solution from the previous step; assumed to contain 61.01 mmol D7) were charged into a reactor at 15° C. to 30° C. The mixture was purged with nitrogen via a subsurface pipe to 0.2 to 0.3 MPa, then vented to 0.02 to 0.05 MPa; this purge/vent operation was carried out 5 to 8 times, until the oxygen content was less than 1.0%. Palladium on charcoal (10%, 0.95 kg) was added at 15° C. to 30° C., whereupon the addition funnel was rinsed with water (0.15 kg). The resulting mixture was purged with nitrogen via a subsurface pipe to 0.2 to 0.3 MPa, then vented to 0.02 to 0.05 MPa at 15° C. to 30° C. This purge/vent procedure was repeated not less than 9 times. The same procedure was then carried out 5 to 8 times, except that hydrogen was used in place of nitrogen. The reaction mixture was then purged with hydrogen via a subsurface pipe to 0.1 to 0.2 MPa, and allowed to react at 20° C. to 30° C. The hydrogen was exchanged twice every 1 to 3 hours in the following manner: the mixture was purged with hydrogen via a subsurface pipe to 0.1 to 0.2 MPa, then vented to 0.02-0.05 MPa and finally purged with hydrogen to 0.1 to 0.2 MPa. After 6 to 12 hours at 20° C. to 30° C., the reaction mixture was sampled every 3 to 12 hours for HPLC analysis, until the area percent of D7 was ≤1.0% (HPLC conditions. Column: Waters XBridge BEH C18, 4.6×150 mm, 3.5 μm; Mobile phase A: water containing 0.1% ammonium acetate; Mobile phase B: acetonitrile; Gradient: 20% to 95% B over 10 minutes; Flow rate: 1.0 mL/minute). Typical retention time for D7: 8.6 minutes.

The reaction mixture was then purged with nitrogen to 0.2 to 0.3 MPa and vented to 0.02 to 0.05 MPa at 15° C. to 30° C. This purge/vent procedure was carried out not less than 9 times. Filtration at 20° C. to 30° C., followed by rinsing of the filter cake with tert-butyl methyl ether (30.0 kg, 40.5 L, 2 volumes relative to D6), provided a filtrate, which was concentrated at −0.08 MPa to a volume of 20 to 30 L while the temperature was maintained below 40° C. n-Heptane (25.0 kg) was added at 15° C. to 30° C., and the resulting mixture was concentrated in the same manner to a volume of 19 to 30 L. n-Heptane (25.0 kg) was again added, and concentration was carried out in the same manner to a volume of 35 to 40 L; this was heated to 40° C. to 50° C., stirred at that temperature for 1 to 2 hours, and filtered at 48° C. to 53° C. The collected solid was dried at 35° C. to 45° C. under a flow of nitrogen. After 6 to 12 hours, the material was sampled for analysis every 2 to 12 hours until residual tert-butyl methyl ether was ≤5000 ppm, residual n-heptane was ≤5000 ppm, and residual methanol was ≤3000 ppm. The solid was then cooled to 15° C. to 30° C., sieved until the appearance of the product was uniform, and dissolved in dichloromethane (187 kg) at 20° C. to 30° C. After this had been stirred for 1 to 2 hours, it was filtered, and the organic layer was concentrated at −0.08 MPa to a volume of 25 to 35 L while the temperature was maintained below 40° C. The resulting mixture was diluted with n-heptane (3 volumes) and concentrated to a volume of 18 to 22 L (approximately 3 volumes); this operation was repeated a total of three times, effecting exchange of n-heptane for dichloromethane. The resulting mixture was allowed to stir and crystallize at 20° C. to 30° C.; it was then filtered to isolate P3 as an off-white solid. Yield: 5.60 kg, 98% by assay; corrected weight: 5.48 kg, 25.1 mol, 41% over 2 steps. HPLC purity: 99% (HPLC conditions. Column: Waters XBridge BEH C18, 4.6×150 mm, 3.5 μm; Mobile phase A: water containing 0.1% ammonium acetate; Mobile phase B: acetonitrile; Gradient: 20% to 95% B over 10 minutes; Flow rate: 1.0 mL/minute). Retention time for P3: 4.93 minutes. $^1$H NMR (401 MHz, chloroform-d), characteristic peaks: δ 4.78 (br d, $J_{HF}$=46.7 Hz, 1H), 4.27-3.91 (m, 2H), 3.21-3.11 (m, 1H), 3.02-2.84 (m, 1H), 2.62-2.35 (m, 1H), 2.29-2.17 (m, 1H), 1.44 (s, 9H).

Preparation P4

2-(5-((3-(Ethoxy-$d_5$)pyridin-2-yl)oxy)pyridin-3-yl)pyrimidine-5-carboxylic Acid (P4)

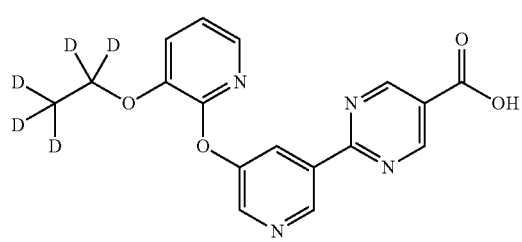

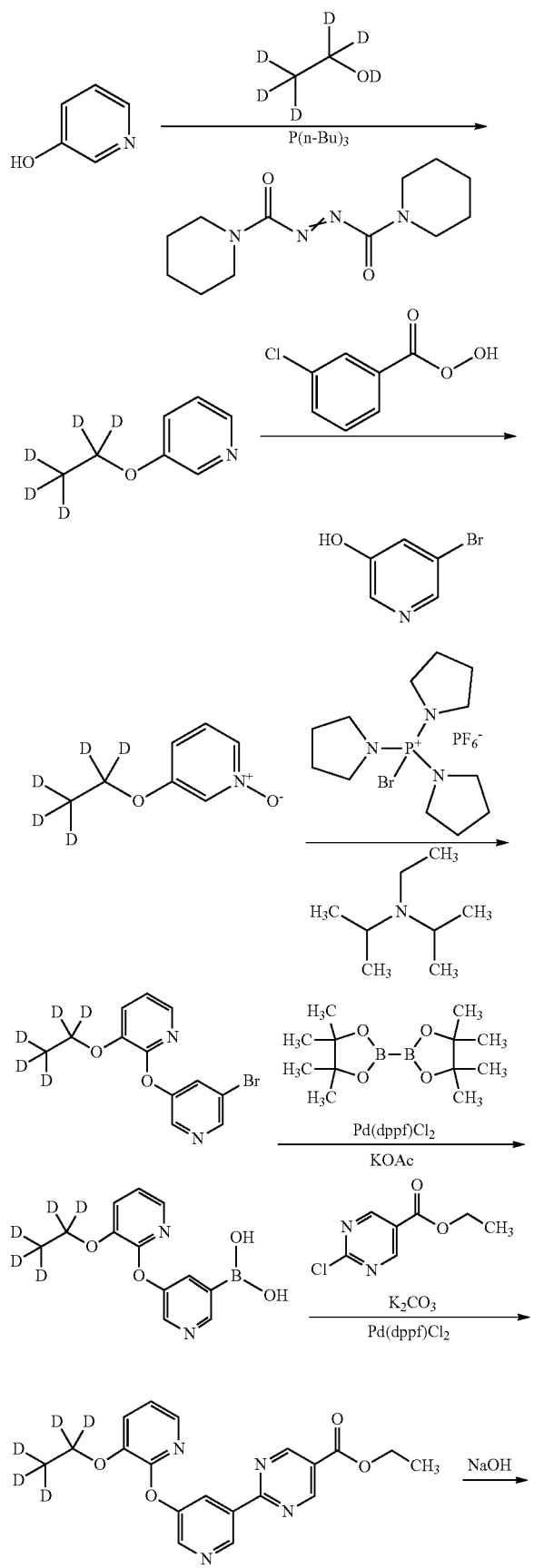

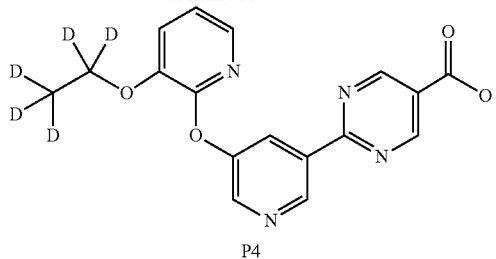

P4

Step 1. Synthesis of 3-(Ethoxy-d$_5$)pyridine

The reaction was carried out in two parallel batches; example batch preparation follows: Tri-n-butylphosphine (8.40 mL, 33.6 mmol, 2.0 equiv.) was added to a solution of 3-hydroxypyridine (1600 mg, 16.8 mmol, 1.0 equiv.) and ethanol-d$_6$ (1.18 mL, 20.2 mmol, 1.2 equiv.) in tetrahydrofuran (60 mL) at 25° C. 1,1'-(Azodicarbonyl)dipiperidine (8490 mg, 33.6 mmol, 2.0 equiv.) was then added and the yellow solution was stirred at 40° C. for 16 hours. The reaction mixture was filtered and to the filtrate was added water (50 mL) and the mixture was extracted with ethyl acetate (2×50 mL). The organic layer was washed with brine (50 mL), dried over sodium sulfate filtered and concentrated to afford the crude product. The crude product was purified by silica gel column chromatography (ISCO 80 g, 3% EtOAc in petroleum ether) to give the title compound as a yellow oil. The combined batches yielded 3.70 g (86%). $^1$H NMR (400 MHz, CDCl$_3$) δ 8.29 (d, J=2.5 Hz, 1H), 8.19 (d, J=4.0 Hz, 1H), 7.12-7.24 (m, 2H).

Step 2. Synthesis of 3-(Ethoxy-d$_5$)pyridine-1-oxide m-Chloroperoxybenzoic acid (7620 mg, 37.5 mmol, 1.3 equiv.) was added to a solution of 3-(ethoxy-d$_5$)pyridine (3700 mg, 28.9 mmol, 1.0 equiv.) in dichloromethane (150 mL) at 0° C. The reaction mixture was stirred at 15° C. for 3 days. Aqueous sodium thiosulfate (100 mL) was added. The reaction mixture was stirred at 15° C. for 0.5 hours. The mixture was extracted with dichloromethane (100 mL). The organic layer dried over sodium sulfate filtered and concentrated to afford the crude product. The crude product was purified by silica gel column chromatography (dichloromethane-10:1 dichloromethane:methanol) to give the title compound (2500.0 mg, 60.1%) as a red solid. $^1$H NMR (400 MHz, CDCl$_3$) δ ppm 7.93-8.00 (m, 1H), 7.86-7.92 (m, 1H), 7.15 (dd, J=8.6, 6.4 Hz, 1H), 6.87 (ddd, J=8.6, 2.2, 0.7 Hz, 1H).

Step 3. Synthesis of 2((5-Bromopyridin-3-yl)oxy)-3-(ethoxy-d$_5$)pyridine

Diisopropylethylamine (11.3 mL, 65.0 mmol, 3.75 equiv.) and bromotripyrrolidinophosphonium hexafluorophosphate (10.5 g, 22.5 mmol, (1.3 equiv.) were added to a stirred solution of 3-(ethoxy-d$_5$)pyridine-1-oxide (2500 mg, 17.3 mmol, 1.0 equiv.) and 3-bromo-5-hydroxypyridine (3020 mg, 17.3 mmol, 1.0 equiv.) in tetrahydrofuran (60 mL) at 0° C. The reaction mixture was stirred at 15° C. for 18 hours. The reaction mixture was concentrated to dryness and dissolved in dichloromethane (150 mL). The organic layer was washed with 1N sodium hydroxide (150 mL), water (100 mL), and brine (100 mL). The organic layer was dried over sodium sulfate, filtered and concentrated to give an oil.

The crude oil was purified by silica gel column chromatography (petroleum ether-80:20 petroleum ether:ethyl acetate) to give product (3600.0 mg, 69.2%) as a white solid. $^1$H NMR (400 MHz, CDCl$_3$) δ ppm 8.48 (d, J=1.8 Hz, 1H), 8.44 (d, J=2.3 Hz, 1H), 7.65-7.74 (m, 2H), 7.19-7.29 (m, 1H), 7.03 (dd, J=7.9, 4.9 Hz, 1H).

Step 4. Synthesis of (5-((3-(Ethoxy-d$_5$)pyridin-2-yl)oxy)pyridin-3-yl)boronic Acid Bis(pinacolato)diboron (3800 mg, 15.0 mmol, 1.2 equiv.), potassium acetate (3670 mg, 37.4 mmol, 3.0 equiv.) and [1,1'-bis(diphenylphosphino)ferrocene]dichloropalladium (II) (Pd(dppf)Cl$_2$; 456 mg, 0.62 mmol, 0.05 equiv.) were added to a solution of 2-((5-bromopyridin-3-yl)oxy)-3-(ethoxy-d$_5$)pyridine (3740 mg, 12.5 mmol, 1.0 equiv.) in dioxane (120 mL). The resulting mixture was degassed and purged with nitrogen 3 times and then stirred at 100° C. under N$_2$ for 2 hrs. The resulting mixture was concentrated and the residue was diluted with ethyl acetate (200 mL) and washed with brine (100 mL). The organic phase was dried over sodium sulfate, filtered and concentrated to dryness to give the crude product (7000.0 mg) as brown oil, which was used for the next step directly. MS (ES+) 265.8 (M+H).

Step 5. Synthesis of Ethyl 2-(5-((3-(ethoxy-d$_5$)pyridin-2-yl)oxy)pyridin-3-yl)pyrimidine-5-carboxylate The reaction was carried out in two parallel batches; example batch preparation follows: Ethyl 2-chloropyrimidine-5-carboxylate (1000 mg, 5.4 mmol, 1.5 equiv.), potassium carbonate (980 mg, 7.1 mmol, 2.0 equiv.) and [1,1'-bis(diphenylphosphino)ferrocene]dichloropalladium(II), dichloromethane complex (130 mg, 0.18 mmol, 0.05 equiv.) were added to a solution of (5-((3-(ethoxy-d$_5$)pyridin-2-yl)oxy)pyridin-3-yl)boronic acid (1880 mg, 3.6 mmol, 1.0 equiv.) in dioxane (25 mL) and water (2.5 mL). The resulting mixture was flushed with nitrogen and then stirred at 90° C. for 2 hours. The reaction was filtered and the filtrate was concentrated. The residue was diluted with ethyl acetate (200 mL) and washed with brine (2×100 mL). The organic layer was dried over sodium sulfate, filtered and concentrated to give the crude product. The crude material was purified by silica gel column chromatography (petroleum ether:ethyl acetate; 70:30) to give product as a yellow solid. The combined batches yielded 2.3 g (50%). $^1$H NMR (400 MHz, CDCl$_3$) δ ppm 9.57 (d, J=1.7 Hz, 1H), 9.34 (s, 2H), 8.68 (d, J=2.7 Hz, 1H), 8.61 (dd, J=2.6, 1.8 Hz, 1H), 7.73 (dd, J=4.8, 1.6 Hz, 1H), 7.28-7.28 (m, 1H), 7.04 (dd, J=8.1, 4.9 Hz, 1H), 7.00-7.08 (m, 1H), 4.48 (q, J=7.1 Hz, 2H), 1.46 (t, J=7.1 Hz, 4H). MS (ES+) 372.1 (M+H).

Step 6: 2-(5-((3-(Ethoxy-d$_5$)pyridin-2-yl)oxy)pyridin-3-yl)pyrimidine-5-carboxylic Acid (P4)

The reaction was carried out in two parallel batches; example batch preparation follows: Sodium hydroxide (1080 mg, 26.9 mmol, 5.0 equiv.) was added to a solution of ethyl 2-(5-((3-(ethoxy-d$_5$)pyridin-2-yl)oxy)pyridin-3-yl)pyrimidine-5-carboxylate (2000 mg, 5.4 mmol, 1.0 equiv.) in tetrahydrofuran (70 mL) and water (35 mL) at 15° C. The resulting solution was stirred at 15° C. for 1 hour. The mixture was concentrated to remove the tetrahydrofuran. The aqueous mixture was acidified to pH of 4 with 4M hydrochloric acid, diluted with water (50 mL) and stirred at 15° C. for 20 minutes. The solid was filtered, washed with water (3×10 mL), and dried to yield 2-(5-((3-(ethoxy-d$_5$)pyridin-2-yl)oxy)pyridin-3-yl)pyrimidine-5-carboxylic acid as a green solid. The combined batches yielded 1.28 g (60%). $^1$H NMR (400 MHz, DMSO-d$_6$) δ ppm 9.41 (d, J=1.7 Hz, 1H), 9.33 (s, 2H) 8.67 (d, J=2.7 Hz, 1H), 8.33-8.41 (m, 1H) 7.70 (dd, J=4.9, 1.5 Hz, 1H), 7.58 (dd, J=7.8, 1.5 Hz, 1H), 7.19 (dd, J=7.8, 4.9 Hz, 1H). HRMS (TOF) 344.1402 (M+H).

Example 1

2-{5-[(3-Ethoxy-5-fluoropyridin-2-yl)oxy]pyridin-3-yl}-N-[(3R,4S)-4-fluoropiperidin-3-yl]pyrimidine-5-carboxamide, bis(trifluoroacetate) Salt (1)

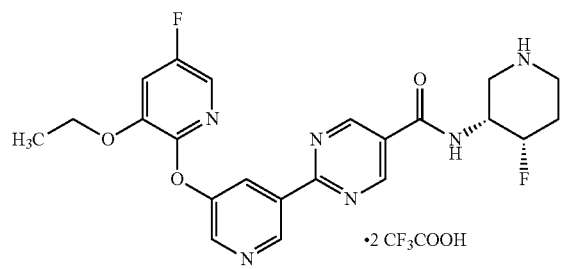

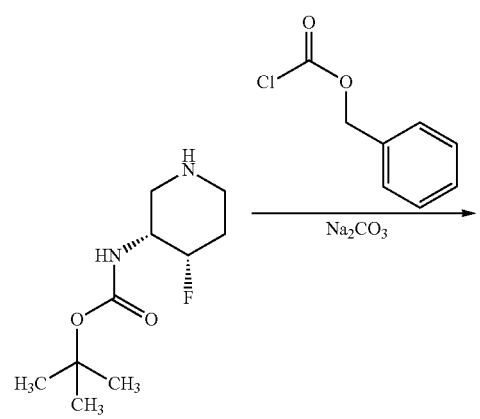

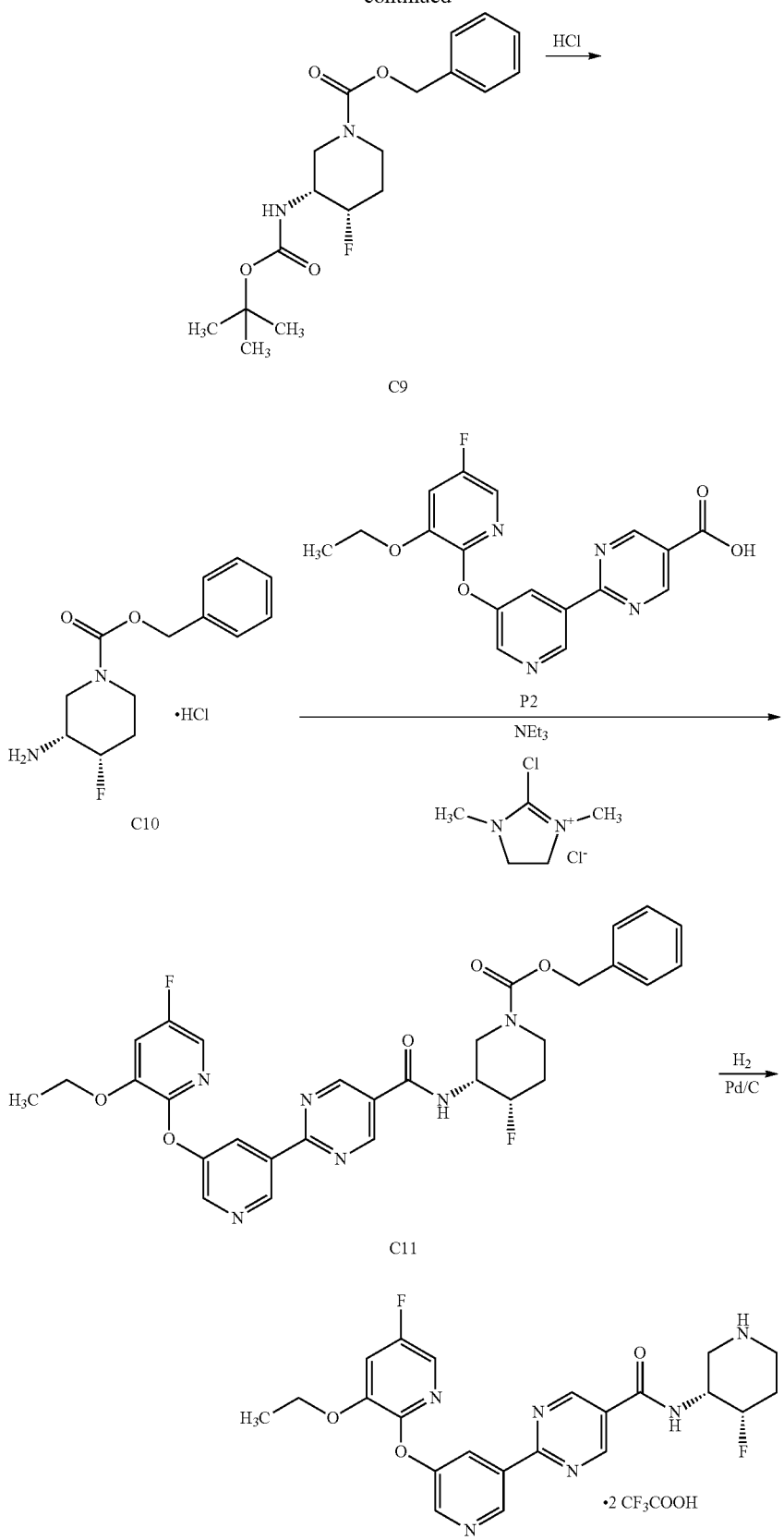

Step 1. Synthesis of benzyl (3R,4S)-3-[(tert-butoxycarbonyl)amino]-4-fluoropiperidine-1-carboxylate (C9)

Benzyl chloroformate (0.116 mL, 0.813 mmol) was added to a 0° C. mixture of tert-butyl [(3R,4S)-4-fluoropiperidin-3-yl]carbamate (150 mg, 0.69 mmol) and sodium carbonate (146 mg, 1.38 mmol) in tetrahydrofuran (8 mL), and the reaction mixture was stirred at 25° C. for three days. It was then treated with water (20 mL) and extracted with ethyl acetate (2×20 mL). The combined organic layers were washed with saturated aqueous sodium chloride solution (50 mL), dried over sodium sulfate, filtered, and concentrated in vacuo to afford C9 as a colorless oil (290 mg). This material contained impurities, by $^1$H NMR analysis, but was used in the next step without additional purification. $^1$H NMR (400 MHz, chloroform-d), characteristic peaks: δ 4.95-4.76 (m, 2H), 3.87-3.68 (m, 1H), 3.12-2.99 (m, 1H), 2.11-1.96 (m, 1H), 1.45 (s, 9H).

Step 2. Synthesis of benzyl (3R,4S)-3-amino-4-fluoropiperidine-1-carboxylate, hydrochloride Salt (C10)

A mixture of C9 (from the previous step; 290 mg, 0.69 mmol) and hydrogen chloride (4 M solution in 1,4-dioxane; 6.0 mL) was stirred at 15° C. for 1 hour, whereupon it was concentrated in vacuo, affording C10 as a white solid. Yield: 200 mg, 0.69 mmol, quantitative over 2 steps. $^1$H NMR (400 MHz, deuterium oxide) δ 7.48-7.33 (m, 5H), 5.14 (s, 2H), 5.11 (br d, $J_{HF}$=48 Hz, 1H), 4.11-3.94 (m, 1H), 3.88-3.28 (m, 4H), 2.14-2.01 (m, 1H), 2.01-1.81 (m, 1H).

Step 3. Synthesis of benzyl (3R,4S)-3-{[(2-{5-[(3-ethoxy-5-fluoropyridin-2-yl)oxy]pyridin-3-yl}pyrimidin-5-yl)carbonyl]amino}-4-fluoropiperidine-1-carboxylate (C11)

To a 25° C. solution of P2 (50.0 mg, 0.140 mmol) in N,N-dimethylacetamide (3.0 mL) were added C10 (48.6 mg, 0.168 mmol), triethylamine (58.7 μL, 0.421 mmol), and 2-chloro-1,3-dimethyl-4,5-dihydro-1H-imidazol-3-ium chloride (71.2 mg, 0.421 mmol). After the reaction mixture had been stirred at 50° C. for 1 hour, it was diluted with water (20 mL) and extracted with ethyl acetate (20 mL). The organic layer was washed with saturated aqueous sodium chloride solution (20 mL), dried over sodium sulfate, filtered, and concentrated in vacuo. Chromatography on silica gel (Eluent: 9:1 ethyl acetate/petroleum ether) provided C11 as a yellow solid. Yield: 80.0 mg, 0.135 mmol, 96%. LCMS m/z 591.2 [M+H]$^+$.

Step 4. Synthesis of 2-{5-[(3-ethoxy-5-fluoropyridin-2-yl)oxy]pyridin-3-yl}-N-[(3R,4S)-4-fluoropiperidin-3-yl]pyrimidine-5-carboxamide, bis(trifluoroacetate) Salt (1)

10% Palladium on carbon (60.0 mg) was added to a solution of C11 (60.0 mg, 0.102 mmol) in tetrahydrofuran (10 mL), whereupon the mixture was degassed under vacuum and then purged with hydrogen; this evacuation-purge cycle was carried out a total of three times. The reaction mixture was then stirred under a balloon of hydrogen for 2 hours at 25° C., at which time it was combined with a similar reaction carried out using C11 (20.0 mg, 33.9 μmol) and filtered. The filtrate was concentrated in vacuo and purified using reversed-phase HPLC (Column: Agela Durashell C18, 5 μm; Mobile phase A: 0.1% trifluoroacetic acid in water; Mobile phase B: acetonitrile; Gradient: 14% to 44% B) to afford 2-{5-[(3-ethoxy-5-fluoropyridin-2-yl)oxy]pyridin-3-yl}-N-[(3R,4S)-4-fluoropiperidin-3-yl]pyrimidine-5-carboxamide, bis(trifluoroacetate) salt as a yellow gum. Combined yield: 28.1 mg, 41.1 μmol, 30%. LCMS m/z 457.4 [M+H]$^+$. $^1$H NMR (400 MHz, chloroform-0, characteristic peaks: δ 9.52 (br s, 1H), 9.16 (br s, 2H), 8.80 (s, 1H), 8.78-8.57 (m, 2H), 7.54 (s, 1H), 7.06 (dd, J=9.2, 2.3 Hz, 1H), 4.99 (br d, $J_{HF}$=50 Hz, 1H), 4.91-4.70 (m, 1H), 4.12 (q, J=6.9 Hz, 2H), 2.41-2.09 (m, 2H), 1.48 (t, J=6.9 Hz, 3H).

Example 2

2-{5-[(3-Ethoxy-5-fluoropyridin-2-yl)oxy]pyridin-3-yl}-N-[(3S,5S)-5-fluoropiperidin-3-yl]pyrimidine-5-carboxamide (2)

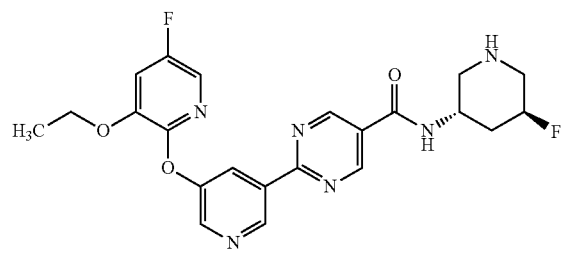

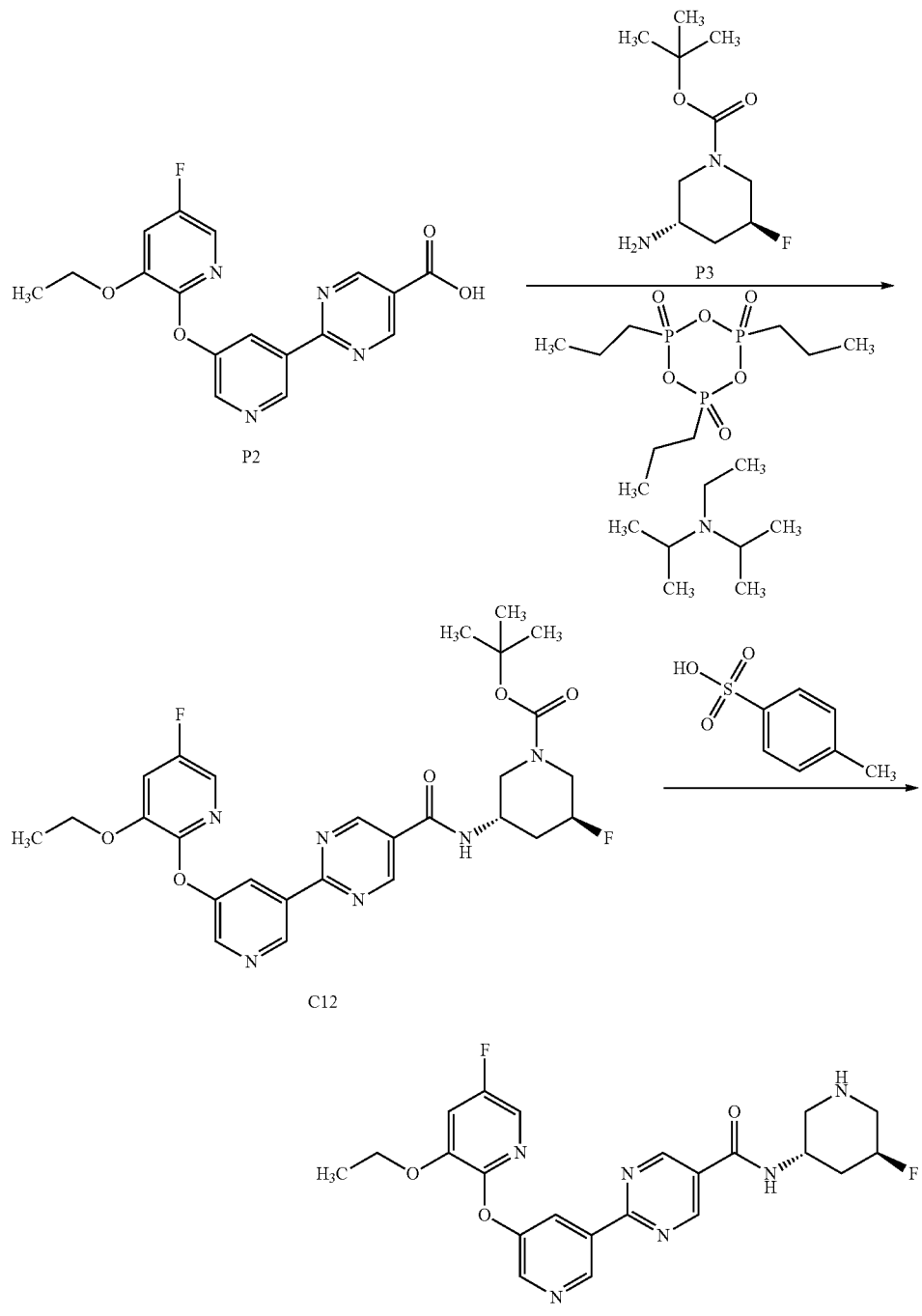

Step 1. Synthesis of tert-butyl (3S,5S)-3{[(2-{5-[(3-ethoxy-5-fluoropyridin-2-yl)oxy]pyridin-3-yl}pyrimidin-5-yl)carbonyl]amino}-5-fluoropiperidine-1-carboxylate (C12)

N,N-Diisopropylethylamine (2.79 mL, 16.0 mmol) and P3 (500 mg, 2.29 mmol) were added to a room temperature solution of P2 (816 mg, 2.29 mmol) in N,N-dimethylformamide (10 mL). After the resulting solution had been cooled to 0° C., 2,4,6-tripropyl-1,3,5,2,4,6-trioxatriphosphinane 2,4,6-trioxide (T3P; 50% solution in ethyl acetate; 1.6 mL, 2.7 mmol) was added, and the reaction mixture was allowed to stir at room temperature for 2 hours. LCMS analysis at this point indicated the presence of C12: LCMS m/z 557.4 [M+H]$^+$. The reaction mixture was partitioned between water and ethyl acetate, and the aqueous layer was extracted twice with ethyl acetate. The combined organic layers were washed twice with water, once with saturated aqueous sodium bicarbonate solution, and once with saturated aqueous sodium chloride solution, then dried over sodium sulfate, filtered, and concentrated in vacuo to provide C12 as a yellow solid. Yield: 1.00 g, 1.80 mmol, 79%.

Step 2. Synthesis of 2-{5-[(3-ethoxy-5-fluoropyridin-2-yl)oxy]pyridin-3-yl}-N-[(3S,5S)-5-fluoropiperidin-3-yl]pyrimidine-5-carboxamide (2)

p-Toluenesulfonic acid monohydrate (684 mg, 3.60 mmol) was added to a solution of C12 (1.00 g, 1.80 mmol) in ethyl acetate (10 mL), and the mixture was allowed to stir at room temperature until a solution was obtained. After the reaction mixture had been stirred at reflux for 2 hours, and then at room temperature for 2 hours, the solvent was decanted off of the resulting gum, and the gum was triturated four times with ethyl acetate, and twice with heptane. The obtained solid was partitioned between ethyl acetate and 1 M aqueous sodium hydroxide solution, and the aqueous layer was extracted four times with ethyl acetate; the combined organic layers were dried over magnesium sulfate, filtered, and concentrated in vacuo. The resulting material was dissolved in ethyl acetate (approximately 70 mL) at reflux, and treated with heptane (300 mL) until the mixture became slightly cloudy, whereupon the mixture was allowed to cool to room temperature and stir overnight. Filtration, followed by washing of the filter cake with 1:1 ethyl acetate/heptane, afforded 2-{5-[(3-ethoxy-5-fluoropyridin-2-yl)oxy]pyridin-3-yl}-N-[(3S,5S)-5-fluoropiperidin-3-yl]pyrimidine-5-carboxamide as a white solid. Yield: 580 mg, 1.27 mmol, 71%. LCMS m/z 457.2 [M+H]+. 1H NMR (400 MHz, DMSO-d6) δ 9.38 (d, J=1.7 Hz, 1H), 9.26 (s, 2H), 8.63 (d, J=2.7 Hz, 1H), 8.59 (br d, J=7.8 Hz, 1H), 8.35 (dd, J=2.7, 1.7 Hz, 1H), 7.71 (d, half of AB quartet, J=2.7 Hz, 1H), 7.68 (dd, component of ABX system, J=9.8, 2.7 Hz, 1H), 4.82 (br d, $J_{HF}$=48 Hz, 1H), 4.20 (q, J=7.0 Hz, 2H), 4.18-4.08 (m, 1H), 3.02-2.86 (m, 2H), 2.77-2.62 (m, 1H), 2.5-2.43 (m, 1H, assumed; partially obscured by solvent peak), 2.19-2.08 (m, 1H), 1.91-1.72 (m, 1H), 1.37 (t, J=7.0 Hz, 3H).

Example 3

2-{5-[(3-Ethoxypyridin-2-yl)oxy]pyridin-3-yl}-N-[(3R,4S)-4-fluoropiperidin-3-yl]pyrimidine-5-carboxamide, bis(trifluoroacetate) Salt (3)

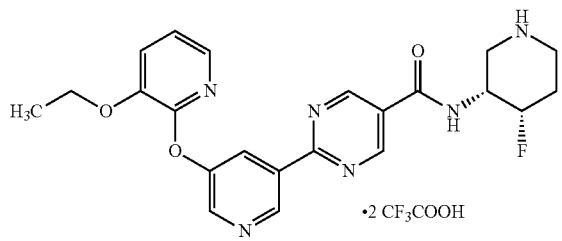

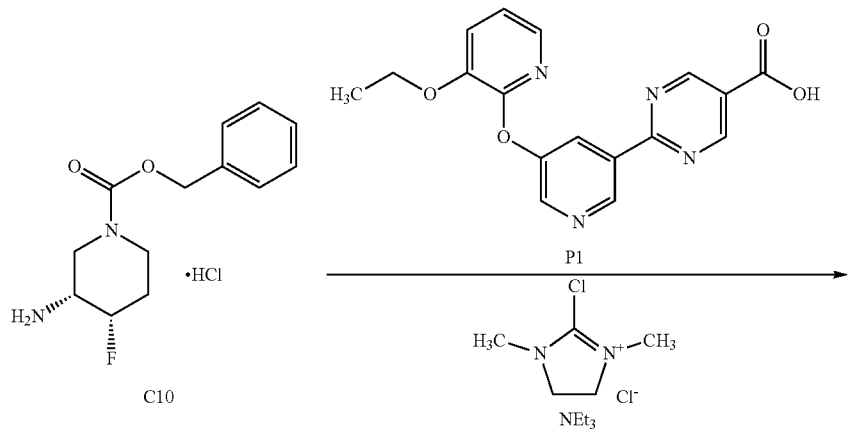

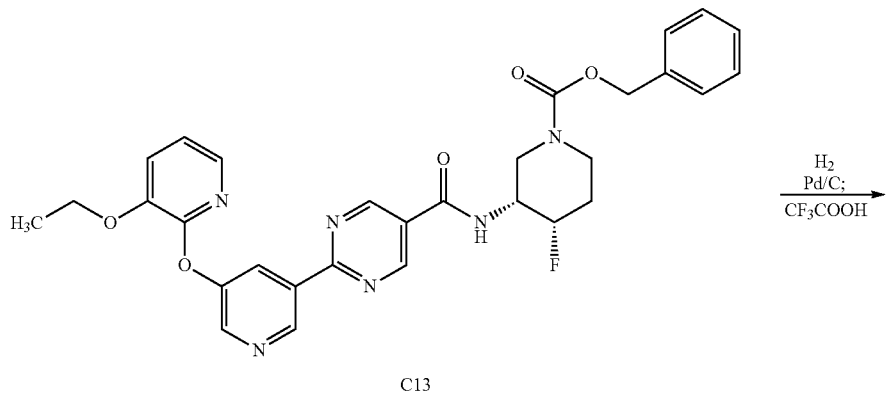

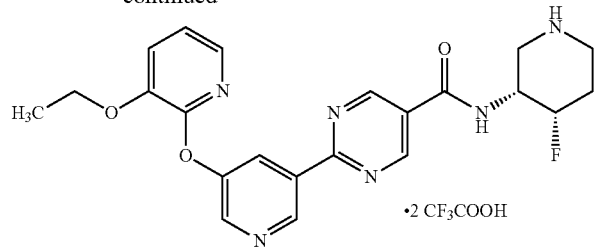

3

Step 1. Synthesis of benzyl (3R,4S)-3-{[(2-{5-[(3-ethoxypyridin-2-yl)oxy]pyridin-3-yl}pyrimidin-5-yl)carbonyl]amino}-4-fluoropiperidine-1-carboxylate (C13)

To a 25° C. solution of P1 (50.0 mg, 0.148 mmol) in N,N-dimethylacetamide (3.0 mL) were added C10 (51.2 mg, 0.177 mmol), 2-chloro-1,3-dimethyl-4,5-dihydro-1H-imidazol-3-ium chloride (75.0 mg, 0.444 mmol), and triethylamine (61.8 µL, 0.443 mmol). The reaction mixture was stirred at 50° C. for 1 hour, whereupon water (20 mL) was added, and the resulting mixture was extracted with ethyl acetate (20 mL). The organic layer was washed with saturated aqueous sodium chloride solution (20 mL), dried over sodium sulfate, filtered, concentrated in vacuo, and subjected to silica gel chromatography (Eluent: 4:1 ethyl acetate/petroleum ether), affording C13 as a yellow solid. Yield: 80.0 mg, 0.140 mmol, 95%. LCMS m/z 573.2 [M+H]$^+$.

Step 2. Synthesis of 2-{5-[(3-ethoxypyridin-2-yl)oxy]pyridin-3-yl}-N-[(3R,4S)-4-fluoropiperidin-3-yl]pyrimidine-5-carboxamide, bis(trifluoroacetate) Salt (3)

To a solution of C13 (60.0 mg, 0.105 mmol) in tetrahydrofuran (10 mL) was added 10% palladium on carbon (60.0 mg), whereupon the mixture was degassed under vacuum and then purged with hydrogen; this evacuation-purge cycle was carried out a total of three times. The reaction mixture was stirred under a balloon of hydrogen for 5 hours at 25° C. and then combined with a similar reaction carried out using C13 (20.0 mg, 34.9 µmol). After this mixture had been filtered, the filtrate was concentrated in vacuo and purified using reversed-phase HPLC (Column: YMC-Actus Triart C18, 5 µm; Mobile phase A: water containing 0.05% ammonium hydroxide; Mobile phase B: acetonitrile; Gradient: 24% to 64% B). The free base 2-{5-[(3-ethoxypyridin-2-yl)oxy]pyridin-3-yl}-N-[(3R,4S)-4-fluoropiperidin-3-yl]pyrimidine-5-carboxamide was obtained as a white solid. Combined yield of free base 2-{5-[(3-ethoxypyridin-2-yl)oxy]pyridin-3-yl}-N-[(3R,4S)-4-fluoropiperidin-3-yl]pyrimidine-5-carboxamide: 12 mg, 27 µmol, 19%. LCMS m/z 439.1 [M+H]$^+$. $^1$H NMR (400 MHz, chloroform-d) δ 9.52 (d, J=1.8 Hz, 1H), 9.17 (s, 2H), 8.65 (d, J=2.7 Hz, 1H), 8.58-8.54 (m, 1H), 7.70 (dd, J=4.9, 1.5 Hz, 1H), 7.27-7.23 (m, 1H, assumed; partially obscured by solvent peak), 7.02 (dd, J=7.9, 4.9 Hz, 1H), 6.68 (br d, J=8.8 Hz, 1H), 4.93 (br d, J$_{HF}$=49 Hz, 1H), 4.48-4.31 (m, 1H), 4.18 (q, J=7.0 Hz, 2H), 3.10 (dd, J=12.1, 4.5 Hz, 1H), 3.00-2.80 (m, 3H), 2.15-2.01 (m, 1H), 1.97-1.77 (m, 1H), 1.50 (t, J=7.0 Hz, 3H).

The free base 2-{5-[(3-ethoxypyridin-2-yl)oxy]pyridin-3-yl}-N-[(3R,4S)-4-fluoropiperidin-3-yl]pyrimidine-5-carboxamide (12 mg, 27 µmol) was dissolved in an aqueous solution of trifluoroacetic acid (0.1% trifluoroacetic acid in water; 12 mL) and then lyophilized for 16 hours to provide 2-{5-[(3-ethoxypyridin-2-yl)oxy]pyridin-3-yl}-N-[(3R,4S)-4-fluoropiperidin-3-yl]pyrimidine-5-carboxamide, bis(trifluoroacetate) salt as a yellow gum. Combined yield of 2-{5-[(3-ethoxypyridin-2-yl)oxy]pyridin-3-yl}-N-[(3R,4S)-4-fluoropiperidin-3-yl]pyrimidine-5-carboxamide, bis(trifluoroacetate) salt: 12.9 mg, 19.4 µmol, 14%. LCMS m/z 439.4 [M+H]$^+$. $^1$H NMR (400 MHz, chloroform-d) δ 10.56-10.28 (br s, 1H), 9.80-9.55 (br s, 1H), 9.71 (s, 1H), 9.24 (s, 2H), 9.09 (br s, 1H), 8.86 (br d, J=7.9 Hz, 1H), 8.77 (d, J=2.5 Hz, 1H), 7.72 (dd, J=4.9, 1.5 Hz, 1H), 7.32 (dd, J=8.1, 1.5 Hz, 1H), 7.14 (dd, J=8.0, 4.9 Hz, 1H), 4.97 (br d, J$_{HF}$=49 Hz, 1H), 4.96-4.78 (m, 1H), 4.18 (q, J=7.0 Hz, 2H), 3.83-3.72 (m, 1H), 3.5-3.2 (m, 3H), 2.42-2.11 (m, 2H), 1.50 (t, J=7.0 Hz, 3H).

Example 4

2-{5-[(3-Ethoxypyridin-2-yl)oxy]pyridin-3-yl}-N-[(3S,5S)-5-fluoropiperidin-3-yl]pyrimidine-5-carboxamide (4)

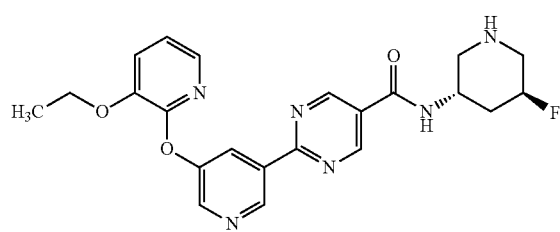

4

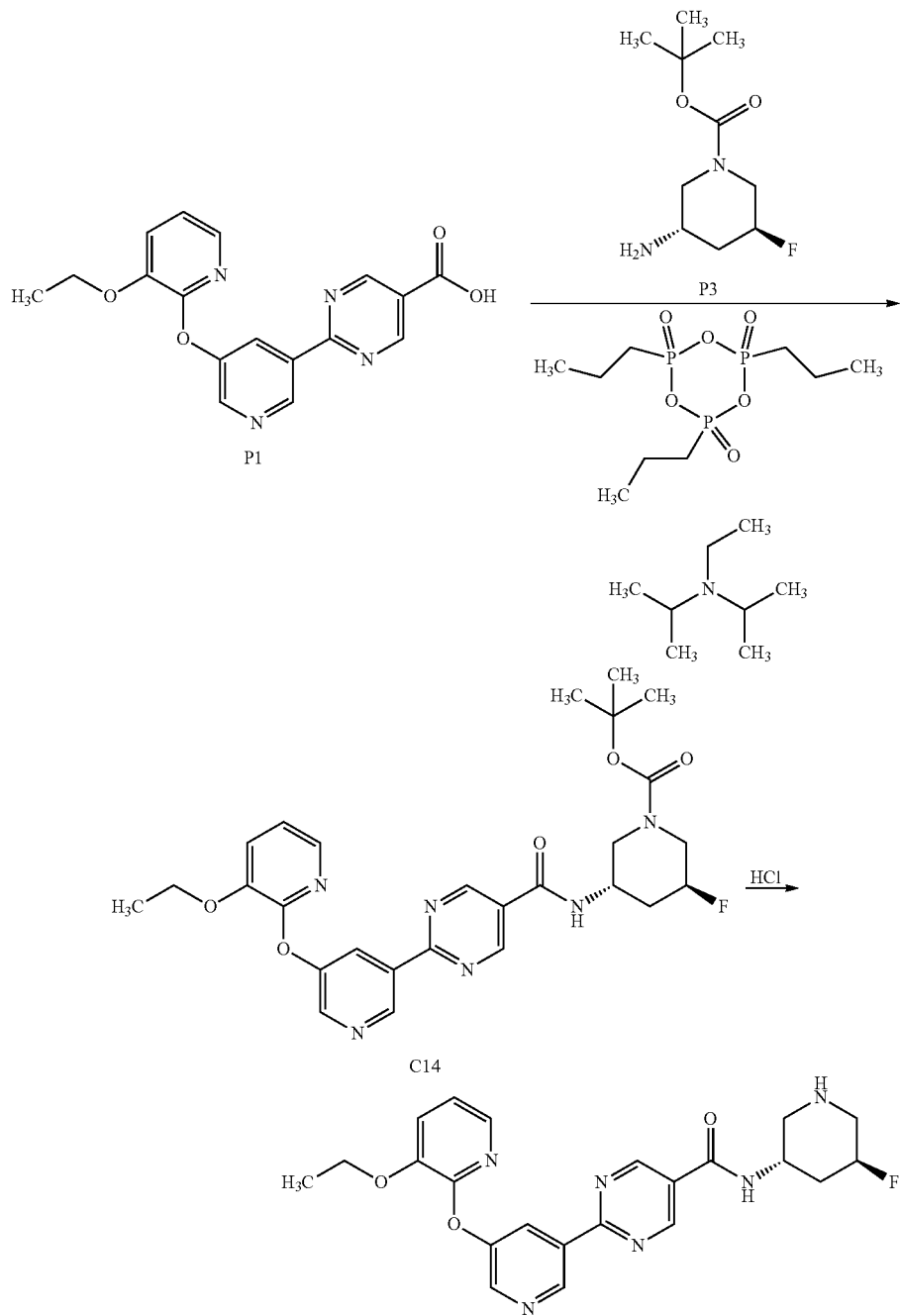

Step 1. Synthesis of tert-butyl (3S,5S)-3-{[(2-{5-[(3-ethoxypyridin-2-yl)oxy]pyridin-3-yl}pyrimidin-5-yl)carbonyl]amino}-5-fluoropiperidine-1-carboxylate (C14)

N,N-Diisopropylethylamine (53.1 mL, 305 mmol) and P3 (9.50 g, 43.5 mmol) were added to a solution of P1 (14.7 g, 43.4 mmol) in acetonitrile (210 mL). The mixture was cooled to 0° C., and then 2,4,6-tripropyl-1,3,5,2,4,6-trioxatriphosphinane 2,4,6-trioxide (T3P; 50% solution in ethyl acetate; 30.5 mL, 51.2 mmol) was added via syringe, over approximately 4 minutes. After the reaction mixture had been stirred at 0° C. for 45 minutes, the ice bath was removed and the reaction mixture was allowed to come to room temperature and stir for 17 hours. It was then concentrated in vacuo, the residue was partitioned between water and ethyl acetate, and the aqueous layer was extracted twice with ethyl acetate. The combined organic layers were washed sequentially with saturated aqueous sodium bicarbonate solution and saturated aqueous sodium chloride solution; a precipitate that appeared during the saturated aqueous sodium chloride wash was removed via filtration and discarded. The saturated aqueous sodium chloride layer was extracted once with ethyl acetate, and the combined organic layers were concentrated in vacuo. The residue was dissolved in a mixture of methylene chloride and methanol and pre-adsorbed onto silica gel. Silica gel chromatography (Gradient: 30% to 100% ethyl acetate in heptane) was carried out, and it was observed that the product was of limited solubility in the ethyl acetate/heptane eluent. This purification afforded C14 as an off-white solid. Yield: 19.1 g, 35.5 mmol, 82%. LCMS m/z 539.3 [M+H]$^+$. $^1$H NMR (400 MHz, chloroform-d) δ 9.48 (d, J=1.8 Hz, 1H), 9.12 (s, 2H), 8.63 (d, J=2.6 Hz, 1H), 8.55 (dd, J=2.7, 1.8 Hz, 1H), 7.70 (dd, J=4.9, 1.5 Hz, 1H), 7.26 (dd, J=7.8, 1.5 Hz, 1H), 7.03 (dd, J=7.9, 4.9 Hz, 1H), 6.97-6.37 (v br m, 1H), 4.78 (br d, $J_{HF}$=46.7 Hz, 1H), 4.46-4.33 (m, 1H), 4.18 (q, J=7.0 Hz, 2H), 4.08-3.05 (v br m, 4H), 2.41-2.11 (m, 1H), 2.02-1.79 (m, 1H), 1.49 (t, J=7.0 Hz, 3H), 1.49 (s, 9H).

Step 2. Synthesis of 2-{5-[(3-ethoxypyridin-2-yl)oxy]pyridin-3-yl}-N-[(3S,5S)-5-fluoropiperidin-3-yl]pyrimidine-5-carboxamide (4)

A solution of hydrogen chloride in 1,4-dioxane (4 M; 520 mL, 2.1 mol) was added over 10 minutes to a room temperature solution of C14 (159 g, 295 mmol) in tetrahydrofuran (850 mL); the reaction temperature increased to 35° C. to 40° C., and this temperature was maintained using a heating mantle. After the addition had been completed, the reaction mixture was stirred for 3 hours at 35° C. to 40° C. LCMS analysis indicated that 20% of the starting material remained, so a solution of hydrogen chloride in 1,4-dioxane (4 M; 150 mL, 600 mmol) was again added to the reaction mixture, and stirring was continued at 35° C. to 40° C. for 30 minutes. At this point, 5% of the starting material remained via LCMS analysis, and the reaction mixture was treated with a solution of hydrogen chloride in 1,4-dioxane (4 M; 60 mL, 240 mmol). After an additional 45 minutes at 35° C. to 40° C., the reaction mixture was concentrated in vacuo, and the resulting solid was dissolved in water (1 L). This solution was treated with aqueous sodium hydroxide solution (1 M; 900 mL, 900 mmol) and then diluted with water (400 mL) to facilitate stirring; after 15 minutes at room temperature, the precipitate was collected via filtration and washed with water (4×250 mL). This solid was brought to a total volume of 800 mL by addition of water, and then slurried with methanol (800 mL) at room temperature for 2 hours, using an overhead stirrer. The slurry was filtered, and the filter cake was washed with a mixture of methanol and water (1:1, 1 L). This solid was combined with the product from several similar reactions carried out using C14 (946 mmol); the combined batches were suspended in ethyl acetate (1.1 L) and stirred for 1 hour at room temperature using a mechanical stirrer. After the solid had been collected by filtration, it was washed with ethyl acetate to afford 2-{5-[(3-ethoxypyridin-2-yl)oxy]pyridin-3-yl}-N-[(3S,5S)-5-fluoropiperidin-3-yl]pyrimidine-5-carboxamide as an off-white solid. The structure of 4 was established based on single-crystal X-ray cryallography as described for tosylate salt form below. Yield: 330 g, 753 mmol, 61% over 2 steps. LCMS m/z 439.3 [M+H]$^+$. $^1$H NMR (400 MHz, DMSO-d$_6$) δ 9.38 (d, J=1.8 Hz, 1H), 9.26 (s, 2H), 8.64 (d, J=2.7 Hz, 1H), 8.60 (br d, J=7.9 Hz, 1H), 8.36 (dd, J=2.7, 1.8 Hz, 1H), 7.68 (dd, J=4.9, 1.5 Hz, 1H), 7.56 (dd, J=8.1, 1.5 Hz, 1H), 7.17 (dd, J=8.0, 4.8 Hz, 1H), 4.81 (br d, $J_{HF}$=48.3 Hz, 1H), 4.22-4.07 (m, 1H), 4.17 (q, J=7.0 Hz, 2H), 3.02-2.86 (m, 2H), 2.69 (br dd, J=35.1, 14.2 Hz, 1H), 2.5-2.38 (m, 2H, assumed; partially obscured by solvent peak), 2.19-2.07 (m, 1H), 1.91-1.72 (m, 1H), 1.37 (t, J=7.0 Hz, 3H).

Powder X-ray diffraction analysis was conducted on the solid of this example using a Bruker AXS D8 Endeavor diffractometer equipped with a Cu radiation source (K-α average). The divergence slit was set at 15 mm continuous illumination. Diffracted radiation was detected by a PSD-Lynx Eye detector, with the detector PSD opening set at 3.00 degrees. The X-ray tube voltage and amperage were set to 40 kV and 40 mA respectively. Data was collected in the Theta-Theta goniometer at the Cu wavelength from 3.0 to 40.0 degrees 2-Theta using a step size of 0.01 degrees and a step time of 1.0 second. The antiscatter screen was set to a fixed distance of 1.5 mm. Samples were rotated at 15/min during collection. Samples were prepared by placing them in a silicon low background sample holder and rotated during collection.

Data were collected using Bruker DIFFRAC Plus software and analysis was performed by EVA diffract plus software. The PXRD data file was not processed prior to peak searching. Using the peak search algorithm in the EVA software, peaks selected with a threshold value of 1 were used to make preliminary peak assignments. To ensure validity, adjustments were manually made; the output of automated assignments was visually checked, and peak positions were adjusted to the peak maximum. Peaks with relative intensity 3% were generally chosen. The peaks which were not resolved or were consistent with noise were not selected. A typical error associated with the peak position from PXRD stated in USP up to ±0.2° 2θ (USP-941). Some variation in relative peak heights is expected based on changes with crystal sizes and morphologies. Characteristic x-ray powder diffraction patterns is provided in FIG. 1. The PXRD data from this figure is further described below.

TABLE A

| PXRD peaks for crystalline material of Example 4, Form 1 | |
|---|---|
| Angle 2Θ (°) | Relative intensity(%) |
| 3.6 | 62 |
| 6.3 | 14 |
| 7.2 | 48 |
| 9.6 | 8 |
| 12.6 | 30 |
| 13.1 | 10 |
| 13.7 | 4 |
| 14.5 | 100 |
| 15.8 | 44 |
| 16.6 | 27 |
| 18.0 | 48 |
| 18.3 | 39 |
| 19.2 | 70 |
| 20.1 | 41 |
| 20.7 | 35 |
| 21.3 | 75 |
| 22.1 | 64 |
| 22.6 | 32 |
| 23.4 | 42 |
| 24.3 | 21 |
| 25.4 | 59 |
| 26.9 | 26 |
| 27.7 | 76 |
| 28.4 | 13 |
| 30.2 | 17 |
| 30.7 | 7 |
| 31.6 | 8 |
| 32.9 | 15 |
| 33.8 | 5 |

TABLE B

Key PXRD peaks to characterize crystalline material of Example 4, Form 1

| Example 4, Form 1 Angle 2Θ (°) ±0.2° |
|---|
| 7.2, 14.5, 15.8, 27.7 |

Example 4, Hydrochloride Salt

2-{5-[(3-Ethoxypyridin-2-yl)oxy]pyridin-3-yl}-N-[(3S,5S)-5-fluoropiperidin-3-yl]pyrimidine-5-carboxamide, hydrochloride Salt (4, hydrochloride Salt)

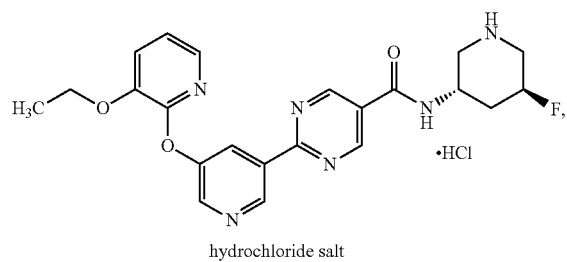

hydrochloride salt

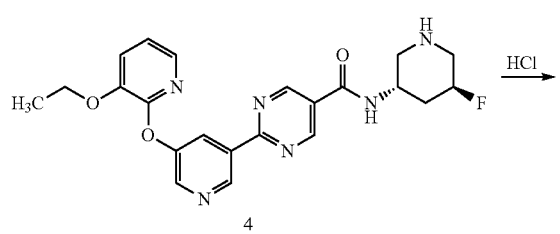

4

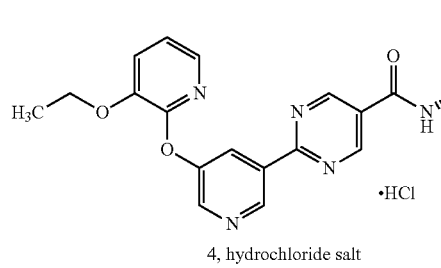

4, hydrochloride salt

A suspension of 2-{5-[(3-ethoxypyridin-2-yl)oxy]pyridin-3-yl}-N-[(3S,5S)-5-fluoropiperidin-3-yl]pyrimidine-5-carboxamide (4.0 g, 9.1 mmol) in ethyl acetate (40 mL) was warmed to approximately 50° C., whereupon a solution of hydrogen chloride in 1,4-dioxane (4 M; 2.5 mL, 10 mmol) was added, and the reaction mixture was stirred at room temperature for 4 days. It was then filtered, and the filter cake was washed twice with warm ethyl acetate, affording 2-{5-[(3-ethoxypyridin-2-yl)oxy]pyridin-3-yl}-N-[(3S,5S)-5-fluoropiperidin-3-yl]pyrimidine-5-carboxamide, hydrochloride salt as a white solid. Yield: 4.1 g, 8.6 mmol, 94%. $^1$H NMR (400 MHz, DMSO-d$_6$) δ 9.90 (br d, J=11 Hz, 1H), 9.39 (d, J=1.8 Hz, 1H), 9.35 (s, 2H), 9.26 (br d, J=7.7 Hz, 1H), 9.24-9.10 (m, 1H), 8.65 (d, J=2.7 Hz, 1H), 8.37 (dd, J=2.7, 1.8 Hz, 1H), 7.69 (dd, J=4.8, 1.5 Hz, 1H), 7.57 (dd, J=8.0, 1.5 Hz, 1H), 7.18 (dd, J=8.0, 4.9 Hz, 1H), 5.23 (br d, J$_{HF}$=45.3 Hz, 1H), 4.54-4.40 (m, 1H), 4.18 (q, J=7.0 Hz, 2H), 3.53-3.41 (m, 1H), 3.39-3.15 (m, 2H), 3.03-2.88 (m, 1H), 2.35-2.21 (m, 1H), 2.13-1.90 (m, 1H), 1.37 (t, J=7.0 Hz, 3H).

Figure 2:
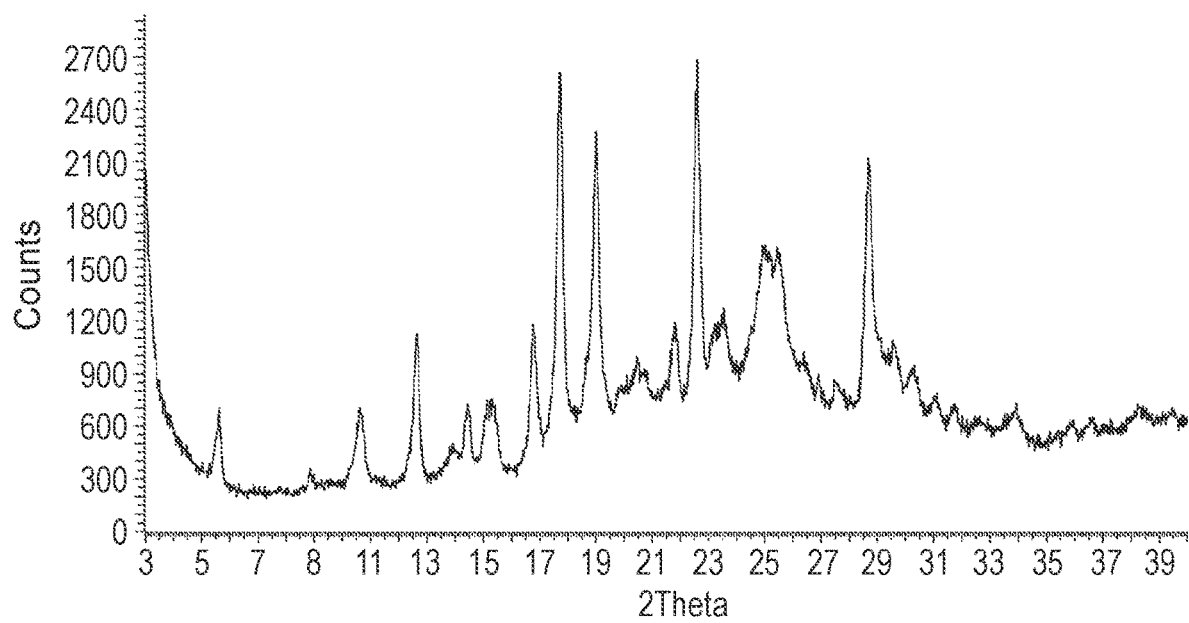
FIG. 2 is a characteristic x-ray powder diffraction pattern showing Example 4, hydrochloride salt Form 1 (Vertical Axis: Intensity (CPS); Horizontal Axis: Two theta (degrees)).

Powder X-ray diffraction analysis was conducted on the solid of this experiment using a Bruker AXS D4 Endeavor diffractometer equipped with a Cu radiation source. The divergence slit was set at 0.6 mm while the secondary optics used variable slits. Diffracted radiation was detected by a PSD-Lynx Eye detector. The X-ray tube voltage and amperage were set to 40 kV and 40 mA respectively. Data was collected in the Theta-2Theta goniometer at the Cu wavelength from 3.0 to 40.0 degrees 2-Theta using a step size of 0.020 degrees and a step time of 0.3 second. Samples were prepared by placing them in a silicon low background sample holder and rotated during collection. Data were collected using Bruker DIFFRAC Plus software and analysis was performed by EVA diffract plus software. Characteristic x-ray powder diffraction pattern is provided in FIG. 2.

Example 4, p-Toluenesulfonate Salt

2-{5-[(3-Ethoxypyridin-2-yl)oxy]pyridin-3-yl}-N-[(3S,5S)-5-fluoropiperidin-3-yl]pyrimidine-5-carboxamide, p-toluenesulfonate Salt (4, p-toluenesulfonate Salt)

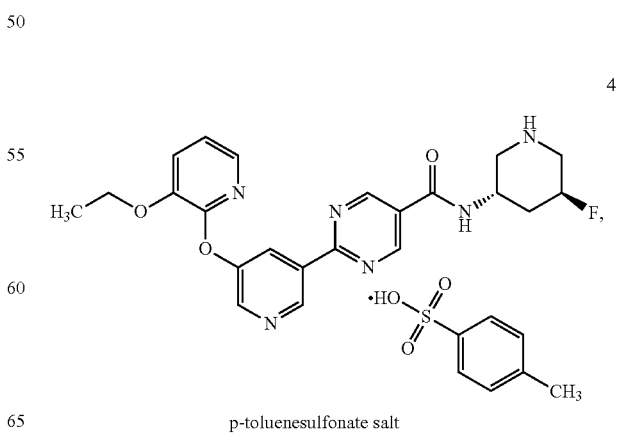

p-toluenesulfonate salt

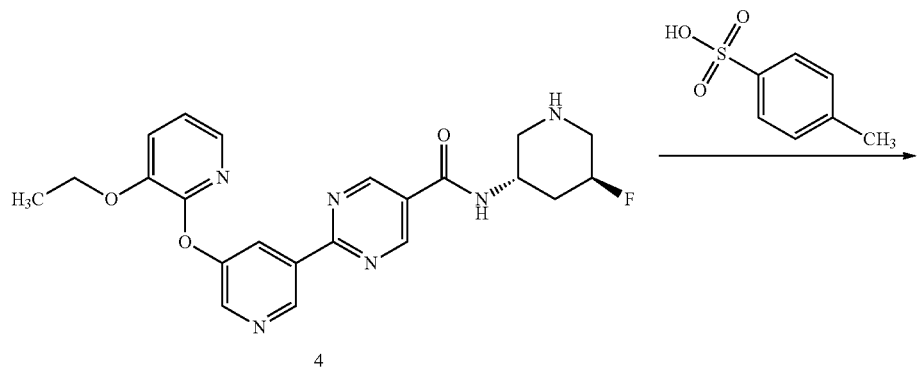

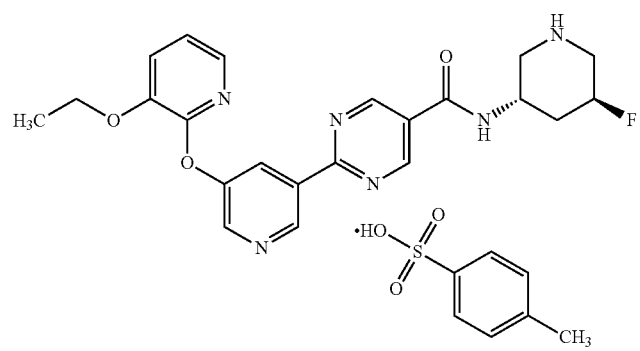

4, p-toluenesulfonate salt

A suspension of 2-{5-[(3-ethoxypyridin-2-yl)oxy]pyridin-3-yl}-N-[(3S,5S)-5-fluoropiperidin-3-yl]pyrimidine-5-carboxamide (4.0 g, 9.1 mmol) in ethyl acetate (40 mL) was warmed to approximately 50° C., whereupon p-toluenesulfonic acid monohydrate (1.9 g, 10 mmol) was added, and the reaction mixture was stirred at room temperature for 3 days. The resulting chunky solid was broken up with a spatula, and the suspended solids were vigorously stirred vigorously for 1 day at room temperature. Filtration provided a filter cake, which was washed twice with warm ethyl acetate to provide 2-{5-[(3-ethoxypyridin-2-yl)oxy]pyridin-3-yl}-N-[(3S,5S)-5-fluoropiperidin-3-yl]pyrimidine-5-carboxamide, p-toluenesulfonate salt as a white solid. Yield: 5.3 g, 8.7 mmol, 96%. LCMS m/z 439.2 [M+H]$^+$. $^1$H NMR (400 MHz, DMSO-d$_6$) δ 9.40 (d, J=1.8 Hz, 1H), 9.28 (s, 2H), 9.24-9.03 (br m, 2H), 8.98 (br d, J=7.6 Hz, 1H), 8.65 (d, J=2.7 Hz, 1H), 8.37 (dd, J=2.7, 1.8 Hz, 1H), 7.68 (dd, J=4.9, 1.5 Hz, 1H), 7.57 (dd, J=8.0, 1.5 Hz, 1H), 7.48 (d, J=8.0 Hz, 2H), 7.18 (dd, J=8.0, 4.8 Hz, 1H), 7.11 (d, J=7.9 Hz, 2H), 5.24 (br d, J$_{HF}$=45.1 Hz, 1H), 4.51-4.38 (m, 1H), 4.18 (q, J=7.0 Hz, 2H), 3.59-3.47 (m, 1H), 3.43-3.17 (m, 2H), 2.98-2.85 (m, 1H), 2.36-2.24 (m, 1H), 2.28 (s, 3H), 2.06-1.85 (m, 1H), 1.37 (t, J=7.0 Hz, 3H).

Crystallization of Example 4, p-Toluenesulfonate Salt

2-{5-[(3-Ethoxypyridin-2-yl)oxy]pyridin-3-yl}-N-[(3S,5S)-5-fluoropiperidin-3-yl]pyrimidine-5-carboxamide, p-toluenesulfonate Salt (4, p-toluenesulfonate Salt)

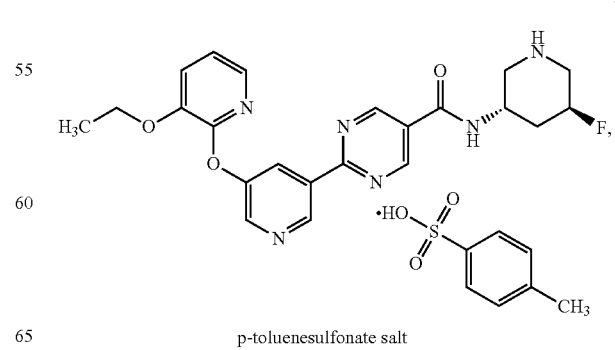

p-toluenesulfonate salt

Treatment of Example 4, p-toluenesulfonate salt (19.1 g, 31.3 mmol) with a mixture of water and ethanol (9:1, 300 mL) was followed by minimal warming with a heat gun, until a solution was obtained. This was allowed to cool to room temperature overnight, and then stirred for an additional 24 hours, whereupon the solvent ratio was adjusted to approximately 4:1 water/ethanol by addition of ethanol (35 mL). The resulting mixture was heated to 85° C. to afford a solution, which was cooled to room temperature over 3 hours and then stirred at room temperature overnight. Collection of the precipitate via filtration afforded a solid, which was dried in a vacuum oven that was equipped with a nitrogen bleed, and had been pre-heated to 40° C. 2-{5-[(3-Ethoxypyridin-2-yl)oxy]pyridin-3-yl}-N-[(3S,5S)-5-fluoropiperidin-3-yl]pyrimidine-5-carboxamide, p-toluenesulfonate salt was obtained as a white powder. Yield: 11.8 g, 19.3 mmol, 62%. LCMS m/z 439.2 [M+H]$^+$. $^1$H NMR (400 MHz, DMSO-d$_6$) δ 9.39 (d, J=1.8 Hz, 1H), 9.27 (s, 2H), 9.13 (br s, 2H), 8.99 (br d, J=7.6 Hz, 1H), 8.65 (d, J=2.7 Hz, 1H), 8.37 (dd, J=2.7, 1.8 Hz, 1H), 7.68 (dd, J=4.8, 1.5 Hz, 1H), 7.57 (dd, J=8.1, 1.5 Hz, 1H), 7.49 (br d, J=8.0 Hz, 2H), 7.18 (dd, J=8.0, 4.8 Hz, 1H), 7.11 (br d, J=8.0 Hz, 2H), 5.24 (br d, J$_{HF}$=45.1 Hz, 1H), 4.52-4.38 (m, 1H), 4.18 (q, J=7.0 Hz, 2H), 3.59-3.47 (m, 1H), 3.44-3.18 (m, 2H), 2.92 (dd, J=11.9, 11.8 Hz, 1H), 2.37-2.22 (m, 1H), 2.27 (s, 3H), 2.08-1.84 (m, 1H), 1.37 (t, J=7.0 Hz, 3H).

Most of this material (11.6 g) was combined with another sample of 2-{5-[(3-ethoxypyridin-2-yl)oxy]pyridin-3-yl}-N-[(3S,5S)-5-fluoropiperidin-3-yl]pyrimidine-5-carboxamide, p-toluenesulfonate salt (7.4 g); the individual samples had exhibited the same diffraction pattern by powder X-ray diffraction analysis. Mixture of the two samples provided a fluffy white solid (19.0 g).

Powder X-ray diffraction analysis was conducted on the solid of this example using a Bruker AXS D8 Endeavor diffractometer equipped with a Cu radiation source (K-α average). The divergence slit was set at 15 mm continuous illumination. Diffracted radiation was detected by a PSD-Lynx Eye detector, with the detector PSD opening set at 3.00 degrees. The X-ray tube voltage and amperage were set to 40 kV and 40 mA respectively. Data was collected in the Theta-Theta goniometer at the Cu wavelength from 3.0 to 40.0 degrees 2-Theta using a step size of 0.01 degrees and a step time of 1.0 second. The antiscatter screen was set to a fixed distance of 1.5 mm. Samples were rotated at 15/min during collection. Samples were prepared by placing them in a silicon low background sample holder and rotated during collection.

Figure 3:
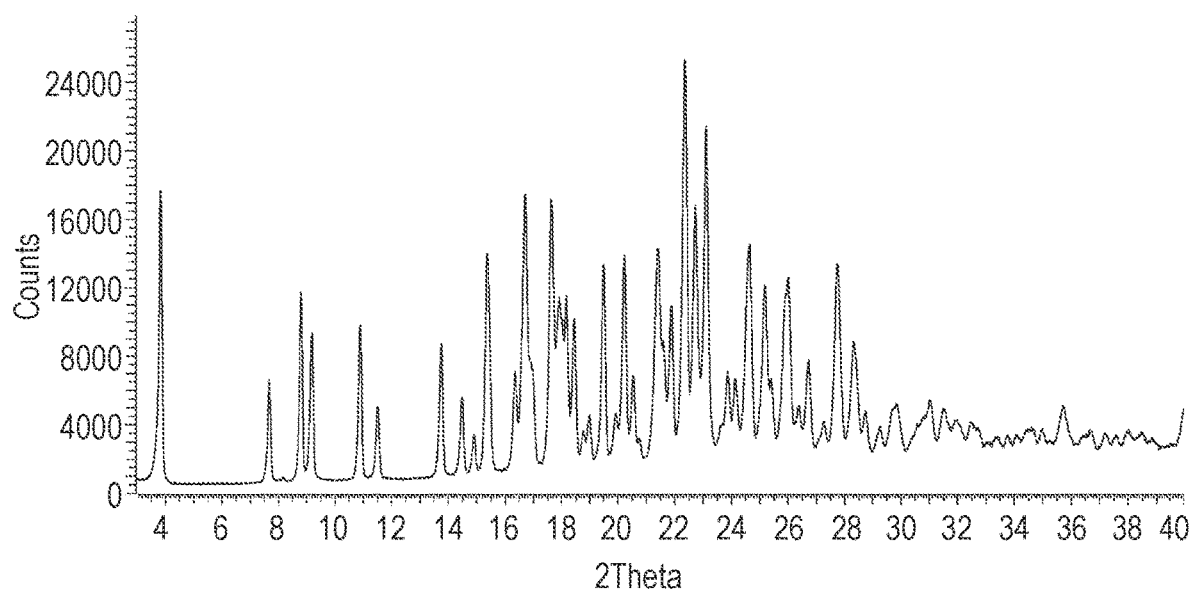
FIG. 3 is a characteristic x-ray powder diffraction pattern showing Example 4, p-toluenesulfonate salt, Anhydrous, Form 1 (Vertical Axis: Intensity (CPS); Horizontal Axis: Two theta (degrees)).

Data were collected using Bruker DIFFRAC Plus software and analysis was performed by EVA diffract plus software. The PXRD data file was not processed prior to peak searching. Using the peak search algorithm in the EVA software, peaks selected with a threshold value of 1 were used to make preliminary peak assignments. To ensure validity, adjustments were manually made; the output of automated assignments was visually checked, and peak positions were adjusted to the peak maximum. Peaks with relative intensity ≥3% were generally chosen. The peaks which were not resolved or were consistent with noise were not selected. A typical error associated with the peak position from PXRD stated in USP is up to ±0.2° 2θ (USP-941). Some variation in relative peak heights is expected based on changes with crystal sizes and morphologies. Characteristic x-ray powder diffraction patterns is provided in FIG. 3. The PXRD data from this figure is further described below.

TABLE C

PXRD peaks for crystalline material of Example 4, p-toluenesulfonate salt, Form 1

| Angle 2Θ (°) | Relative intensity(%) |
|---|---|
| 3.8 | 74 |
| 7.7 | 26 |
| 8.8 | 48 |
| 9.2 | 38 |
| 10.9 | 39 |
| 11.5 | 19 |
| 13.8 | 33 |
| 14.5 | 19 |
| 14.9 | 10 |
| 15.4 | 55 |
| 16.4 | 25 |
| 16.7 | 69 |
| 16.9 | 27 |
| 17.6 | 67 |
| 17.9 | 42 |
| 18.2 | 42 |
| 18.4 | 36 |
| 18.8 | 8 |
| 19.0 | 12 |
| 19.5 | 50 |
| 19.9 | 12 |
| 20.2 | 51 |
| 20.5 | 21 |
| 20.8 | 5 |
| 21.4 | 53 |
| 21.6 | 29 |
| 21.9 | 38 |
| 22.4 | 100 |
| 22.7 | 63 |
| 23.1 | 83 |
| 23.6 | 7 |
| 23.9 | 20 |
| 24.2 | 18 |
| 24.6 | 52 |
| 25.2 | 41 |
| 25.4 | 18 |
| 26.0 | 44 |
| 26.4 | 11 |
| 26.7 | 23 |
| 27.3 | 7 |
| 27.7 | 47 |
| 28.3 | 27 |
| 28.7 | 10 |
| 29.3 | 6 |
| 29.8 | 12 |
| 31.0 | 12 |
| 31.5 | 10 |
| 32.0 | 7 |
| 32.5 | 6 |
| 32.7 | 5 |
| 35.0 | 5 |
| 35.7 | 10 |
| 37.2 | 4 |
| 37.6 | 3 |
| 38.0 | 5 |
| 25.9 | 38 |
| 36.7 | 4 |

TABLE D

Key PXRD peaks to characterize crystalline material of Example 4, p-toluenesulfonate salt, Form 1
Example 4, p-toluenesulfonate salt, Form 1

| Angle 2Θ (°) ±0.2° |
|---|
| 3.8, 7.7, 8.8, 22.4, 24.6 |

Alternate Synthesis of Example 4, p-Toluenesulfonate Salt

2-{5-[(3-Ethoxypyridin-2-yl)oxy]pyridin-3-yl}-N-[(3S,5S)-5-fluoropiperidin-3-yl]pyrimidine-5-carboxamide, p-Toluenesulfonate Salt (4, p-toluenesulfonate Salt)

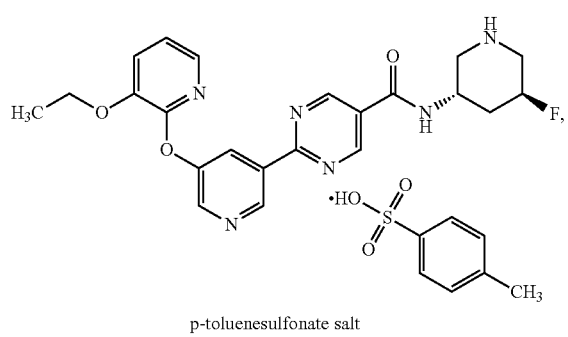

p-toluenesulfonate salt

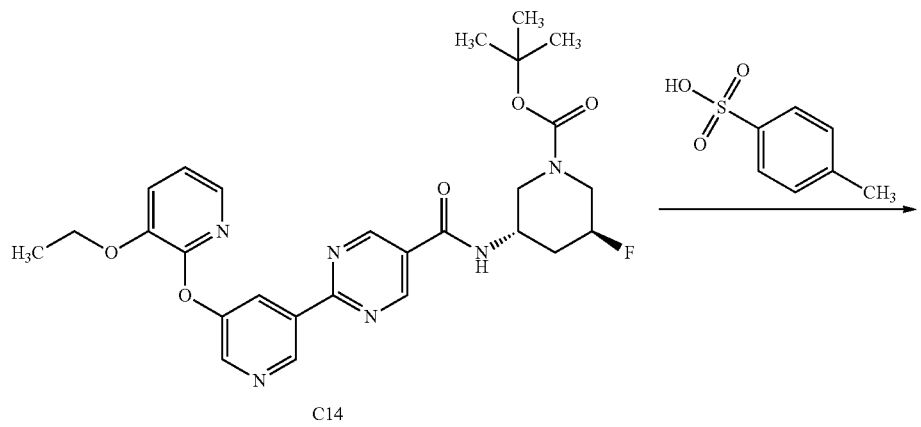

C14

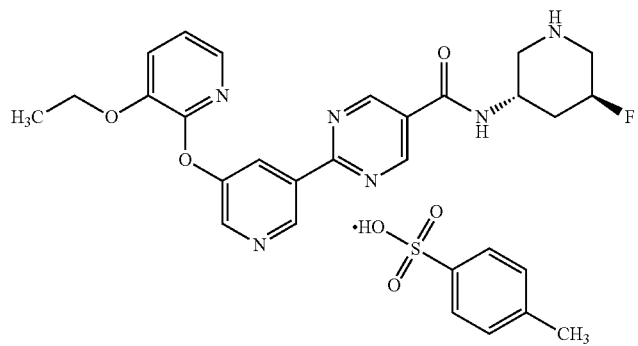

4, p-toluenesulfonate salt

A solution of C14 (9.47 g, 17.6 mmol), p-toluenesulfonic acid monohydrate (98%, 3.58 g, 18.4 mmol), and water (4.74 mL, 263 mmol) in acetonitrile (90.0 mL) was heated to 90° C. over 10 minutes (internal reaction temperature 76° C.). After 12 hours, the reaction mixture was cooled to 25° C. over 10 minutes, and held at 25° C. overnight. It was then cooled to 10° C., and filtered. The filter cake was rinsed twice with 1 volume of a 95:5 acetonitrile/water mixture that had been cooled to 10° C., affording 2-{5-[(3-ethoxypyridin-2-yl)oxy]pyridin-3-yl}-N-[(3S,5S)-5-fluoropiperidin-3-yl]pyrimidine-5-carboxamide, p-toluenesulfonate salt as a yellow solid. Yield: 8.30 g, 13.6 mmol, 77%. $^1$H NMR (400 MHz, DMSO-$d_6$) δ 9.40 (d, J=1.8 Hz, 1H), 9.27 (s, 2H), 9.17-9.07 (br s, 2H), 8.97 (br d, J=7.6 Hz, 1H), 8.65 (d, J=2.7 Hz, 1H), 8.37 (dd, J=2.7, 1.7 Hz, 1H), 7.68 (dd, J=4.9, 1.5 Hz, 1H), 7.57 (dd, J=8.0, 1.5 Hz, 1H), 7.47 (br d, J=8.0 Hz, 2H), 7.18 (dd, J=7.9, 4.9 Hz, 1H), 7.11 (br d, J=7.9 Hz, 2H), 5.24 (br d, $J_{HF}$=45.1 Hz, 1H), 4.52-4.38 (m, 1H), 4.18 (q, J=7.0 Hz, 2H), 3.59-3.47 (m, 1H), 3.44-3.19 (m, 2H), 2.90 (dd, J=11.8, 11.8 Hz, 1H), 2.36-2.25 (m, 1H), 2.28 (s, 3H), 2.06-1.84 (m, 1H), 1.37 (t, J=7.0 Hz, 3H).

Single-Crystal X-Ray Structural Determination of Example 4, p-Toluenesulfonate Salt Crystallization of Example 4, p-toluenesulfonate salt (10 mg) from ethanol (3 mL), with slow diffusion of toluene and water (1:1), afforded a crystal suitable for X-ray structural determination.

Single-Crystal X-Ray Analysis

Data collection was performed on a Bruker D8 Venture diffractometer at −100° C. Data collection consisted of omega and phi scans.

The structure was solved by intrinsic phasing using SHELX software suite in the Triclinic space group P1 as two molecules per Asymmetric Unit. The structure was subsequently refined by the full-matrix least squares method. All non-hydrogen atoms were found and refined using anisotropic displacement parameters.

The hydrogen atoms located on nitrogen and oxygen were found from the Fourier difference map and refined with distances restrained. The remaining hydrogen atoms were placed in calculated positions and were allowed to ride on their carrier atoms. The final refinement included isotropic displacement parameters for all hydrogen atoms.

Confirmed Tosylate Salt of Crystallization.

Refinement challenging due to low occupancy of ethanol sitting in channels and also due to the marginal quality of crystalline prismatic particles which were observed as stacked plates (see PLM picture). Based on confirmed Ethanol incorporation by NMR experiments, refined the molecular model with two ethanol entities each by occupancy of 0.33.

Analysis of the absolute structure using likelihood methods (Hooft 2008) was performed using PLATON (Spek 2010). Assuming the sample submitted is enantiopure, the results indicate that the absolute structure has been correctly assigned. The method calculates that the probability that the structure is correctly assigned is 100%. The Hooft parameter is reported as 0.075 with an Esd of (4) and the Parson's parameter is reported as 0.087 with an Esd of (5).

Targeted Absolute configuration at C18_C21/C40_C43 confirmed as (-S)_(-S)/(-S)_(-S) for both identical molecules per Asymmetric Unit.

Pertinent crystal, data collection and refinement information is summarized in Table D1. Atomic coordinates, bond lengths, bond angles, and displacement parameters are listed in Tables D2-D4.

SOFTWARE AND REFERENCES

SHELXTL, Version 5.1, Bruker AXS, 1997.

PLATON, A. L. Spek, *J. Appl. Cryst.* 2003, 36, 7-13.

MERCURY, C. F. Macrae, P. R. Edington, P. McCabe, E. Pidcock, G. P. Shields, R. Taylor, M. Towler, and J. van de Streek, *J. Appl. Cryst.* 2006, 39, 453-457.

OLEX2, O. V. Dolomanov, L. J. Bourhis, R. J. Gildea, J. A. K. Howard, and H. Puschmann, *J. Appl. Cryst.* 2009, 42, 339-341.

R. W. W. Hooft, L. H. Straver, and A. L. Spek, *J. Appl. Cryst.* 2008, 41, 96-103.

H. D. Flack, *Acta Cryst.* 1983, A39, 867-881.

TABLE D1

Crystal data and structure refinement for Example 4, p-toluenesulfonate salt.

| | |
|---|---|
| Empirical formula | C29.67 H33 F N6 O6.33 S |
| Formula weight | 626.00 |
| Temperature | 296(2) K |
| Wavelength | 1.54178 Å |
| Crystal system | Triclinic |
| Space group | P1 |
| Unit cell dimensions | a = 6.9545(4) Å α = 83.178(2)°. |
| | b = 10.1175(6) Å β = 83.176(2)°. |
| | c = 24.8467(15) Å γ = 70.487(2)°. |
| Volume | 1630.33(17) Å$^3$ |
| Z | 2 |
| Density(calculated) | 1.275 Mg/m$^3$ |
| Absorption coefficient | 1.364 mm$^{-1}$ |
| F(000) | 657.3 |
| Crystal size | 0.340 × 0.260 × 0.180 mm$^3$ |
| Theta range for data collection | 6.778 to 72.343°. |
| Index ranges | $-8 <= h <= 8, -10 <= k <= 12, -30 <= l <= 30$ |
| Reflections collected | 29135 |
| Independent reflections | 10147 [R(int) = 0.0194] |
| Completeness to theta = 67.679° | 94.3% |
| Absorption correction | Empirical |
| Refinement method | Full-matrix least-squares on F$^2$ |
| Data/restraints/parameters | 10147/13/855 |
| Goodness-of-fit on F$^2$ | 1.060 |
| Final R indices [I > 2sigma(I)] | R1 =0.0417, wR2 = 0.1220 |
| R indices(all data) | R1 =0.0424, wR2 = 0.1232 |
| Absolute structure parameter | 0.073(4) |
| Extinction coefficient | n/a |
| Largest diff. peak and hole | 0.362 and −0.298 e.Å$^{-3}$ |

TABLE D2

Atomic coordinates (×10$^4$) and equivalent isotropic displacement parameters (Å$^2$ × 10$^3$) for Example 4, p-toluenesulfonate salt. U(eq) is defined as one-third of the trace of the orthogonalized U$^{ij}$ tensor.

| | x | y | z | U(eq) |
|---|---|---|---|---|
| S(1) | −504(1) | 9393(1) | 6147(1) | 56(1) |
| S(2) | 9899(1) | 723(1) | 3887(1) | 55(1) |
| F(1) | 6010(4) | 5903(2) | 4063(1) | 76(1) |
| F(2) | 1076(4) | 4209(2) | 5953(1) | 76(1) |
| N(1) | −73(4) | 8526(3) | 9140(1) | 57(1) |
| N(2) | 5643(4) | 5070(3) | 9141(1) | 50(1) |
| N(3) | 6364(5) | 4830(3) | 7460(1) | 51(1) |
| N(4) | 5074(4) | 7330(3) | 7319(1) | 48(1) |
| N(5) | 6710(4) | 6840(3) | 5637(1) | 47(1) |
| N(6) | 8253(4) | 7736(3) | 4185(1) | 49(1) |
| N(7) | 10069(4) | 1597(3) | 880(2) | 56(1) |
| N(8) | 4367(4) | 5049(3) | 882(1) | 49(1) |
| N(9) | 3437(5) | 5273(3) | 2563(1) | 51(1) |
| N(10) | 4605(4) | 2768(3) | 2693(1) | 49(1) |
| N(11) | 4065(4) | 3245(3) | 4389(1) | 47(1) |

TABLE D2-continued

Atomic coordinates (×10$^4$) and equivalent isotropic displacement parameters (Å$^2$ × 10$^3$) for Example 4, p-toluenesulfonate salt. U(eq) is defined as one-third of the trace of the orthogonalized U$^{ij}$ tensor.

|  | x | y | z | U(eq) |
|---|---|---|---|---|
| N(12) | 5166(5) | 2326(3) | 5844(1) | 50(1) |
| O(1) | 1301(3) | 11465(2) | 9415(1) | 52(1) |
| O(2) | 3013(3) | 8817(2) | 9228(1) | 49(1) |
| O(3) | 6096(4) | 4779(2) | 5794(1) | 60(1) |
| O(4) | 8707(3) | −1350(2) | 609(1) | 53(1) |
| O(5) | 6972(3) | 1302(2) | 796(1) | 50(1) |
| O(6) | 1531(4) | 5290(2) | 4222(1) | 60(1) |
| O(7) | 1453(7) | 9131(5) | 5849(2) | 111(2) |
| O(8) | −2111(6) | 9139(3) | 5888(1) | 78(1) |
| O(9) | −1262(5) | 10812(3) | 6314(1) | 72(1) |
| O(10) | 7844(5) | 1001(3) | 4148(1) | 82(1) |
| O(11) | 11371(8) | 981(5) | 4181(2) | 111(2) |
| O(12) | 10637(4) | −704(3) | 3720(1) | 71(1) |
| C(1) | 17(4) | 10769(3) | 9335(1) | 42(1) |
| C(2) | 385(5) | 12923(3) | 9510(2) | 60(1) |
| C(3) | 2066(7) | 13492(5) | 9570(3) | 79(1) |
| C(4) | −2095(5) | 11305(4) | 9354(2) | 54(1) |
| C(5) | −3181(5) | 10433(4) | 9267(2) | 66(1) |
| C(6) | −2143(6) | 9064(4) | 9163(2) | 66(1) |
| C(7) | 910(4) | 9349(3) | 9230(1) | 41(1) |
| C(8) | 3933(4) | 7539(3) | 8998(1) | 43(1) |
| C(9) | 4660(5) | 6310(3) | 9334(1) | 46(1) |
| C(10) | 5913(5) | 5041(3) | 8601(2) | 46(1) |
| C(11) | 5266(4) | 6213(3) | 8231(1) | 42(1) |
| C(12) | 4248(5) | 7504(3) | 8445(1) | 45(1) |
| C(13) | 5598(5) | 6114(3) | 7638(1) | 44(1) |
| C(14) | 6592(6) | 4772(3) | 6928(2) | 52(1) |
| C(15) | 6094(5) | 5955(3) | 6560(1) | 46(1) |
| C(16) | 5334(5) | 7234(3) | 6789(2) | 49(1) |
| C(17) | 6305(5) | 5808(3) | 5964(1) | 47(1) |
| C(18) | 6865(5) | 6816(3) | 5048(1) | 44(1) |
| C(19) | 8066(5) | 7774(3) | 4790(1) | 49(1) |
| C(20) | 6234(6) | 8182(4) | 3948(2) | 62(1) |
| C(21) | 4982(6) | 7279(4) | 4213(2) | 61(1) |
| C(22) | 4761(5) | 7240(4) | 4826(2) | 54(1) |
| C(23) | 9990(4) | −646(3) | 683(1) | 42(1) |
| C(24) | 9627(6) | −2816(3) | 515(2) | 58(1) |
| C(25) | 7950(7) | −3368(5) | 458(3) | 82(1) |
| C(26) | 12095(5) | −1180(4) | 671(2) | 53(1) |
| C(27) | 13184(5) | −289(4) | 753(2) | 66(1) |
| C(28) | 12139(6) | 1052(5) | 860(2) | 71(1) |
| C(29) | 9074(4) | 774(3) | 795(1) | 42(1) |
| C(30) | 6040(4) | 2583(3) | 1023(1) | 43(1) |
| C(31) | 5379(5) | 3789(3) | 690(1) | 46(1) |
| C(32) | 4037(5) | 5082(3) | 1420(1) | 45(1) |
| C(33) | 4644(4) | 3893(3) | 1787(1) | 42(1) |
| C(34) | 5672(5) | 2610(3) | 1578(1) | 45(1) |
| C(35) | 4214(4) | 3979(3) | 2386(1) | 43(1) |
| C(36) | 3062(5) | 5326(3) | 3095(2) | 51(1) |
| C(37) | 3433(5) | 4131(3) | 3460(1) | 45(1) |
| C(38) | 4218(5) | 2848(3) | 3230(2) | 50(1) |
| C(39) | 2939(5) | 4261(3) | 4052(1) | 46(1) |
| C(40) | 3668(5) | 3271(3) | 4976(1) | 43(1) |
| C(41) | 5543(5) | 2290(3) | 5240(1) | 48(1) |
| C(42) | 3344(7) | 1911(4) | 6069(2) | 63(1) |
| C(43) | 1487(6) | 2828(4) | 5803(2) | 62(1) |
| C(44) | 1772(5) | 2867(4) | 5191(2) | 56(1) |
| C(45) | −135(5) | 8251(4) | 6752(2) | 49(1) |
| C(46) | −589(7) | 8761(5) | 7248(2) | 70(1) |
| C(47) | −273(8) | 7839(6) | 7713(2) | 76(1) |
| C(48) | 474(7) | 6399(6) | 7686(2) | 75(1) |
| C(49) | 775(9) | 5426(8) | 8202(3) | 111(2) |
| C(50) | 911(7) | 5909(5) | 7175(2) | 75(1) |
| C(51) | 632(6) | 6808(4) | 6712(2) | 59(1) |
| C(52) | 9677(5) | 1870(4) | 3286(2) | 50(1) |
| C(53) | 8944(6) | 3304(4) | 3324(2) | 60(1) |
| C(54) | 8775(6) | 4199(4) | 2853(2) | 70(1) |
| C(55) | 9315(6) | 3696(6) | 2349(2) | 76(1) |
| C(56) | 9112(9) | 4698(8) | 1836(3) | 112(1) |
| C(57) | 10049(8) | 2253(7) | 2315(2) | 81(1) |
| C(58) | 10221(7) | 1346(5) | 2782(2) | 67(1) |
| O(13) | 6240(40) | 9576(13) | 2638(6) | 181(10) |
| C(60) | 7290(60) | 8670(18) | 2244(7) | 240(30) |
| C(59) | 8830(30) | 7950(20) | 2701(10) | 138(9) |
| O(14) | 1850(40) | 1387(18) | 7804(9) | 193(12) |
| C(62) | 3900(40) | 1300(20) | 7773(11) | 126(8) |
| C(61) | 4670(30) | 2131(18) | 7343(8) | 103(6) |

TABLE D3

Bond lengths [Å] and angles [°] for Example 4, p-toluenesulfonate salt

| | |
|---|---|
| S(1)—O(7) | 1.427(4) |
| S(1)—O(9) | 1.447(3) |
| S(1)—O(8) | 1.460(3) |
| S(1)—C(45) | 1.772(4) |
| S(2)—O(11) | 1.432(4) |
| S(2)—O(10) | 1.448(3) |
| S(2)—O(12) | 1.456(3) |
| S(2)—C(52) | 1.768(4) |
| F(1)—C(21) | 1.408(4) |
| F(2)—C(43) | 1.416(4) |
| N(1)—C(7) | 1.293(4) |
| N(1)—C(6) | 1.355(5) |
| N(2)—C(9) | 1.328(4) |
| N(2)—C(10) | 1.334(5) |
| N(3)—C(14) | 1.319(5) |
| N(3)—C(13) | 1.337(4) |
| N(4)—C(16) | 1.319(5) |
| N(4)—C(13) | 1.346(4) |
| N(5)—C(17) | 1.331(4) |
| N(5)—C(18) | 1.457(4) |
| N(5)—H(5X) | 0.96(2) |
| N(6)—C(19) | 1.496(4) |
| N(6)—C(20) | 1.494(5) |
| N(6)—H(6X) | 0.96(2) |
| N(6)—H(6Y) | 0.98(2) |
| N(7)—C(29) | 1.296(4) |
| N(7)—C(28) | 1.356(5) |
| N(8)—C(32) | 1.333(5) |
| N(8)—C(31) | 1.346(4) |
| N(9)—C(36) | 1.321(5) |
| N(9)—C(35) | 1.345(4) |
| N(10)—C(35) | 1.328(4) |
| N(10)—C(38) | 1.335(5) |
| N(11)—C(39) | 1.336(4) |
| N(11)—C(40) | 1.452(4) |
| N(11)—H(11X) | 0.96(2) |
| N(12)—C(42) | 1.492(5) |
| N(12)—C(41) | 1.496(4) |
| N(12)—H(12X) | 0.98(2) |
| N(12)—H(12Y) | 0.98(2) |
| O(1)—C(1) | 1.352(4) |
| O(1)—C(2) | 1.434(4) |
| O(2)—C(7) | 1.379(4) |
| O(2)—C(8) | 1.393(4) |
| O(3)—C(17) | 1.226(4) |
| O(4)—C(23) | 1.354(4) |
| O(4)—C(24) | 1.441(4) |
| O(5)—C(29) | 1.378(4) |
| O(5)—C(30) | 1.394(3) |
| O(6)—C(39) | 1.242(4) |
| C(1)—C(4) | 1.382(4) |
| C(1)—C(7) | 1.405(4) |
| C(2)—C(3) | 1.494(6) |
| C(2)—H(2A) | 0.9700 |
| C(2)—H(2B) | 0.9700 |
| C(3)—H(3A) | 0.9600 |
| C(3)—H(3B) | 0.9600 |
| C(3)—H(3C) | 0.9600 |
| C(4)—C(5) | 1.388(5) |
| C(4)—H(4) | 0.9300 |
| C(5)—C(6) | 1.371(6) |
| C(5)—H(5) | 0.9300 |

TABLE D3-continued

Bond lengths [Å] and angles [°]
for Example 4, p-toluenesulfonate salt

| | |
|---|---|
| C(6)—H(6) | 0.9300 |
| C(8)—C(12) | 1.369(5) |
| C(8)—C(9) | 1.391(5) |
| C(9)—H(9) | 0.9300 |
| C(10)—C(11) | 1.391(5) |
| C(10)—H(10) | 0.9300 |
| C(11)—C(12) | 1.396(4) |
| C(11)—C(13) | 1.474(5) |
| C(12)—H(12) | 0.9300 |
| C(14)—C(15) | 1.387(5) |
| C(14)—H(14) | 0.9300 |
| C(15)—C(16) | 1.386(5) |
| C(15)—C(17) | 1.491(5) |
| C(16)—H(16) | 0.9300 |
| C(18)—C(19) | 1.521(4) |
| C(18)—C(22) | 1.531(5) |
| C(18)—H(18) | 0.9800 |
| C(19)—H(19A) | 0.9700 |
| C(19)—H(19B) | 0.9700 |
| C(20)—C(21) | 1.509(6) |
| C(20)—H(20A) | 0.9700 |
| C(20)—H(20B) | 0.9700 |
| C(21)—C(22) | 1.510(6) |
| C(21)—H(21) | 0.9800 |
| C(22)—H(22A) | 0.9700 |
| C(22)—H(22B) | 0.9700 |
| C(23)—C(26) | 1.379(4) |
| C(23)—C(29) | 1.409(4) |
| C(24)—C(25) | 1.479(6) |
| C(24)—H(24A) | 0.9700 |
| C(24)—H(24B) | 0.9700 |
| C(25)—H(25A) | 0.9600 |
| C(25)—H(25B) | 0.9600 |
| C(25)—H(25C) | 0.9600 |
| C(26)—C(27) | 1.402(5) |
| C(26)—H(26) | 0.9300 |
| C(27)—C(28) | 1.349(6) |
| C(27)—H(27) | 0.9300 |
| C(28)—H(28) | 0.9300 |
| C(30)—C(31) | 1.363(5) |
| C(30)—C(34) | 1.375(5) |
| C(31)—H(31) | 0.9300 |
| C(32)—C(33) | 1.396(5) |
| C(32)—H(32) | 0.9300 |
| C(33)—C(34) | 1.384(4) |
| C(33)—C(35) | 1.488(5) |
| C(34)—H(34) | 0.9300 |
| C(36)—C(37) | 1.392(5) |
| C(36)—H(36) | 0.9300 |
| C(37)—C(38) | 1.393(4) |
| C(37)—C(39) | 1.481(5) |
| C(38)—H(38) | 0.9300 |
| C(40)—C(41) | 1.517(4) |
| C(40)—C(44) | 1.528(4) |
| C(40)—H(40) | 0.9800 |
| C(41)—H(41A) | 0.9700 |
| C(41)—H(41B) | 0.9700 |
| C(42)—C(43) | 1.491(6) |
| C(42)—H(42A) | 0.9700 |
| C(42)—H(42B) | 0.9700 |
| C(43)—C(44) | 1.508(6) |
| C(43)—H(43) | 0.9800 |
| C(44)—H(44A) | 0.9700 |
| C(44)—H(44B) | 0.9700 |
| C(45)—C(46) | 1.356(6) |
| C(45)—C(51) | 1.387(5) |
| C(46)—C(47) | 1.386(7) |
| C(46)—H(46) | 0.9300 |
| C(47)—C(48) | 1.381(8) |
| C(47)—H(47) | 0.9300 |
| C(48)—C(50) | 1.380(8) |
| C(48)—C(49) | 1.512(6) |
| C(49)—H(49A) | 0.9600 |
| C(49)—H(49B) | 0.9600 |
| C(49)—H(49C) | 0.9600 |
| C(50)—C(51) | 1.369(6) |
| C(50)—H(50) | 0.9300 |
| C(51)—H(51) | 0.9300 |
| C(52)—C(53) | 1.380(5) |
| C(52)—C(58) | 1.380(6) |
| C(53)—C(54) | 1.385(6) |
| C(53)—H(53) | 0.9300 |
| C(54)—C(55) | 1.371(8) |
| C(54)—H(54) | 0.9300 |
| C(55)—C(57) | 1.386(8) |
| C(55)—C(56) | 1.521(6) |
| C(56)—H(56A) | 0.9600 |
| C(56)—H(56B) | 0.9600 |
| C(56)—H(56C) | 0.9600 |
| C(57)—C(58) | 1.380(7) |
| C(57)—H(57) | 0.9300 |
| C(58)—H(58) | 0.9300 |
| O(13)—C(60) | 1.39(2) |
| O(13)—H(13) | 0.8359 |
| C(60)—C(59) | 1.59(2) |
| C(60)—H(60A) | 0.9700 |
| C(60)—H(60B) | 0.9700 |
| C(59)—H(59A) | 0.9651 |
| C(59)—H(59B) | 0.9648 |
| C(59)—H(59C) | 0.9651 |
| O(14)—C(62) | 1.39(2) |
| O(14)—H(14A) | 0.9219 |
| C(62)—C(61) | 1.44(2) |
| C(62)—H(62A) | 0.9700 |
| C(62)—H(62B) | 0.9700 |
| C(61)—H(61A) | 0.9600 |
| C(61)—H(61B) | 0.9600 |
| C(61)—H(61C) | 0.9600 |
| O(7)—S(1)—O(9) | 110.8(3) |
| O(7)—S(1)—O(8) | 117.4(3) |
| O(9)—S(1)—O(8) | 108.60(18) |
| O(7)—S(1)—C(45) | 106.8(2) |
| O(9)—S(1)—C(45) | 106.46(18) |
| O(8)—S(1)—C(45) | 106.22(17) |
| O(11)—S(2)—O(10) | 117.1(3) |
| O(11)—S(2)—O(12) | 111.1(3) |
| O(10)—S(2)—O(12) | 108.98(19) |
| O(11)—S(2)—C(52) | 106.2(2) |
| O(10)—S(2)—C(52) | 106.09(17) |
| O(12)—S(2)—C(52) | 106.79(18) |
| C(7)—N(1)—C(6) | 117.5(3) |
| C(9)—N(2)—C(10) | 117.1(3) |
| C(14)—N(3)—C(13) | 116.4(3) |
| C(16)—N(4)—C(13) | 116.8(3) |
| C(17)—N(5)—C(18) | 120.8(3) |
| C(17)—N(5)—H(5X) | 113(2) |
| C(18)—N(5)—H(5X) | 126(2) |
| C(19)—N(6)—C(20) | 113.4(3) |
| C(19)—N(6)—H(6X) | 106(2) |
| C(20)—N(6)—H(6X) | 115(3) |
| C(19)—N(6)—H(6Y) | 107(2) |
| C(20)—N(6)—H(6Y) | 112(2) |
| H(6X)—N(6)—H(6Y) | 103(4) |
| C(29)—N(7)—C(28) | 117.6(3) |
| C(32)—N(8)—C(31) | 117.0(3) |
| C(36)—N(9)—C(35) | 116.1(3) |
| C(35)—N(10)—C(38) | 116.7(3) |
| C(39)—N(11)—C(40) | 121.4(3) |
| C(39)—N(11)—H(11X) | 119(2) |
| C(40)—N(11)—H(11X) | 119(2) |
| C(42)—N(12)—C(41) | 112.7(3) |
| C(42)—N(12)—H(12X) | 111(3) |
| C(41)—N(12)—H(12X) | 111(2) |
| C(42)—N(12)—H(12Y) | 111(3) |
| C(41)—N(12)—H(12Y) | 109(2) |
| H(12X)—N(12)—H(12Y) | 103(4) |
| C(1)—O(1)—C(2) | 116.7(2) |
| C(7)—O(2)—C(8) | 115.5(2) |
| C(23)—O(4)—C(24) | 116.9(2) |
| C(29)—O(5)—C(30) | 115.7(2) |
| O(1)—C(1)—C(4) | 126.7(3) |
| O(1)—C(1)—C(7) | 116.9(3) |
| C(4)—C(1)—C(7) | 116.4(3) |
| O(1)—C(2)—C(3) | 107.9(3) |

TABLE D3-continued

Bond lengths [Å] and angles [°]
for Example 4, p-toluenesulfonate salt

| | |
|---|---|
| O(1)—C(2)—H(2A) | 110.1 |
| C(3)—C(2)—H(2A) | 110.1 |
| O(1)—C(2)—H(2B) | 110.1 |
| C(3)—C(2)—H(2B) | 110.1 |
| H(2A)—C(2)—H(2B) | 108.4 |
| C(2)—C(3)—H(3A) | 109.5 |
| C(2)—C(3)—H(3B) | 109.5 |
| H(3A)—C(3)—H(3B) | 109.5 |
| C(2)—C(3)—H(3C) | 109.5 |
| H(3A)—C(3)—H(3C) | 109.5 |
| H(3B)—C(3)—H(3C) | 109.5 |
| C(1)—C(4)—C(5) | 119.0(3) |
| C(1)—C(4)—H(4) | 120.5 |
| C(5)—C(4)—H(4) | 120.5 |
| C(6)—C(5)—C(4) | 119.5(3) |
| C(6)—C(5)—H(5) | 120.2 |
| C(4)—C(5)—H(5) | 120.2 |
| N(1)—C(6)—C(5) | 122.1(3) |
| N(1)—C(6)—H(6) | 119.0 |
| C(5)—C(6)—H(6) | 118.9 |
| N(1)—C(7)—O(2) | 118.8(3) |
| N(1)—C(7)—C(1) | 125.5(3) |
| O(2)—C(7)—C(1) | 115.8(2) |
| C(12)—C(8)—C(9) | 120.0(3) |
| C(12)—C(8)—O(2) | 120.3(3) |
| C(9)—C(8)—O(2) | 119.6(3) |
| N(2)—C(9)—C(8) | 122.6(3) |
| N(2)—C(9)—H(9) | 118.7 |
| C(8)—C(9)—H(9) | 118.7 |
| N(2)—C(10)—C(11) | 124.8(3) |
| N(2)—C(10)—H(10) | 117.6 |
| C(11)—C(10)—H(10) | 117.6 |
| C(10)—C(11)—C(12) | 117.0(3) |
| C(10)—C(11)—C(13) | 122.3(3) |
| C(12)—C(11)—C(13) | 120.7(3) |
| C(8)—C(12)—C(11) | 118.6(3) |
| C(8)—C(12)—H(12) | 120.7 |
| C(11)—C(12)—H(12) | 120.7 |
| N(3)—C(13)—N(4) | 125.2(3) |
| N(3)—C(13)—C(11) | 117.7(3) |
| N(4)—C(13)—C(11) | 117.1(3) |
| N(3)—C(14)—C(15) | 123.4(3) |
| N(3)—C(14)—H(14) | 118.3 |
| C(15)—C(14)—H(14) | 118.3 |
| C(16)—C(15)—C(14) | 115.5(3) |
| C(16)—C(15)—C(17) | 124.0(3) |
| C(14)—C(15)—C(17) | 120.5(3) |
| N(4)—C(16)—C(15) | 122.7(3) |
| N(4)—C(16)—H(16) | 118.7 |
| C(15)—C(16)—H(16) | 118.6 |
| O(3)—C(17)—N(5) | 122.7(3) |
| O(3)—C(17)—C(15) | 120.4(3) |
| N(5)—C(17)—C(15) | 116.8(3) |
| N(5)—C(18)—C(19) | 108.8(2) |
| N(5)—C(18)—C(22) | 112.1(3) |
| C(19)—C(18)—C(22) | 111.3(3) |
| N(5)—C(18)—H(18) | 108.2 |
| C(19)—C(18)—H(18) | 108.2 |
| C(22)—C(18)—H(18) | 108.2 |
| N(6)—C(19)—C(18) | 108.9(3) |
| N(6)—C(19)—H(19A) | 109.9 |
| C(18)—C(19)—H(19A) | 109.9 |
| N(6)—C(19)—H(19B) | 109.9 |
| C(18)—C(19)—H(19B) | 109.9 |
| H(19A)—C(19)—H(19B) | 108.3 |
| N(6)—C(20)—C(21) | 109.9(3) |
| N(6)—C(20)—H(20A) | 109.7 |
| C(21)—C(20)—H(20A) | 109.7 |
| N(6)—C(20)—H(20B) | 109.7 |
| C(21)—C(20)—H(20B) | 109.7 |
| H(20A)—C(20)—H(20B) | 108.2 |
| F(1)—C(21)—C(22) | 108.5(3) |
| F(1)—C(21)—C(20) | 106.9(3) |
| C(22)—C(21)—C(20) | 113.1(3) |
| F(1)—C(21)—H(21) | 109.5 |
| C(22)—C(21)—H(21) | 109.4 |
| C(20)—C(21)—H(21) | 109.4 |
| C(21)—C(22)—C(18) | 110.5(3) |
| C(21)—C(22)—H(22A) | 109.6 |
| C(18)—C(22)—H(22A) | 109.6 |
| C(21)—C(22)—H(22B) | 109.6 |
| C(18)—C(22)—H(22B) | 109.6 |
| H(22A)—C(22)—H(22B) | 108.1 |
| O(4)—C(23)—C(26) | 126.7(3) |
| O(4)—C(23)—C(29) | 116.6(2) |
| C(26)—C(23)—C(29) | 116.7(3) |
| O(4)—C(24)—C(25) | 107.4(3) |
| O(4)—C(24)—H(24A) | 110.2 |
| C(25)—C(24)—H(24A) | 110.3 |
| O(4)—C(24)—H(24B) | 110.2 |
| C(25)—C(24)—H(24B) | 110.2 |
| H(24A)—C(24)—H(24B) | 108.5 |
| C(24)—C(25)—H(25A) | 109.5 |
| C(24)—C(25)—H(25B) | 109.5 |
| H(25A)—C(25)—H(25B) | 109.5 |
| C(24)—C(25)—H(25C) | 109.5 |
| H(25A)—C(25)—H(25C) | 109.5 |
| H(25B)—C(25)—H(25C) | 109.5 |
| C(23)—C(26)—C(27) | 118.9(3) |
| C(23)—C(26)—H(26) | 120.5 |
| C(27)—C(26)—H(26) | 120.5 |
| C(28)—C(27)—C(26) | 119.1(3) |
| C(28)—C(27)—H(27) | 120.4 |
| C(26)—C(27)—H(27) | 120.5 |
| C(27)—C(28)—N(7) | 123.0(3) |
| C(27)—C(28)—H(28) | 118.5 |
| N(7)—C(28)—H(28) | 118.5 |
| N(7)—C(29)—O(5) | 119.2(3) |
| N(7)—C(29)—C(23) | 124.7(3) |
| O(5)—C(29)—C(23) | 116.1(3) |
| C(31)—C(30)—C(34) | 120.5(3) |
| C(31)—C(30)—O(5) | 119.6(3) |
| C(34)—C(30)—O(5) | 119.8(3) |
| N(8)—C(31)—C(30) | 122.7(3) |
| N(8)—C(31)—H(31) | 118.7 |
| C(30)—C(31)—H(31) | 118.7 |
| N(8)—C(32)—C(33) | 123.8(3) |
| N(8)—C(32)—H(32) | 118.1 |
| C(33)—C(32)—H(32) | 118.1 |
| C(34)—C(33)—C(32) | 117.9(3) |
| C(34)—C(33)—C(35) | 120.3(3) |
| C(32)—C(33)—C(35) | 121.8(3) |
| C(30)—C(34)—C(33) | 118.2(3) |
| C(30)—C(34)—H(34) | 120.9 |
| C(33)—C(34)—H(34) | 120.9 |
| N(10)—C(35)—N(9) | 126.1(3) |
| N(10)—C(35)—C(33) | 116.9(3) |
| N(9)—C(35)—C(33) | 117.0(3) |
| N(9)—C(36)—C(37) | 123.1(3) |
| N(9)—C(36)—H(36) | 118.4 |
| C(37)—C(36)—H(36) | 118.4 |
| C(36)—C(37)—C(38) | 115.8(3) |
| C(36)—C(37)—C(39) | 120.5(3) |
| C(38)—C(37)—C(39) | 123.7(3) |
| N(10)—C(38)—C(37) | 122.1(3) |
| N(10)—C(38)—H(38) | 118.9 |
| C(37)—C(38)—H(38) | 118.9 |
| O(6)—C(39)—N(11) | 122.1(3) |
| O(6)—C(39)—C(37) | 120.3(3) |
| N(11)—C(39)—C(37) | 117.5(3) |
| N(11)—C(40)—C(41) | 108.7(2) |
| N(11)—C(40)—C(44) | 112.3(3) |
| C(41)—C(40)—C(44) | 110.7(3) |
| N(11)—C(40)—H(40) | 108.4 |
| C(41)—C(40)—H(40) | 108.3 |
| C(44)—C(40)—H(40) | 108.3 |
| N(12)—C(41)—C(40) | 109.2(3) |
| N(12)—C(41)—H(41A) | 109.8 |
| C(40)—C(41)—H(41A) | 109.8 |
| N(12)—C(41)—H(41B) | 109.8 |
| C(40)—C(41)—H(41B) | 109.8 |
| H(41A)—C(41)—H(41B) | 108.3 |
| C(43)—C(42)—N(12) | 110.3(3) |
| C(43)—C(42)—H(42A) | 109.6 |

TABLE D3-continued

Bond lengths [Å] and angles [°]
for Example 4, p-toluenesulfonate salt

| | |
|---|---|
| N(12)—C(42)—H(42A) | 109.6 |
| C(43)—C(42)—H(42B) | 109.6 |
| N(12)—C(42)—H(42B) | 109.6 |
| H(42A)—C(42)—H(42B) | 108.1 |
| F(2)—C(43)—C(42) | 107.2(3) |
| F(2)—C(43)—C(44) | 108.3(3) |
| C(42)—C(43)—C(44) | 113.0(3) |
| F(2)—C(43)—H(43) | 109.4 |
| C(42)—C(43)—H(43) | 109.4 |
| C(44)—C(43)—H(43) | 109.4 |
| C(43)—C(44)—C(40) | 110.5(3) |
| C(43)—C(44)—H(44A) | 109.6 |
| C(40)—C(44)—H(44A) | 109.6 |
| C(43)—C(44)—H(44B) | 109.6 |
| C(40)—C(44)—H(44B) | 109.5 |
| H(44A)—C(44)—H(44B) | 108.1 |
| C(46)—C(45)—C(51) | 119.8(4) |
| C(46)—C(45)—S(1) | 121.2(3) |
| C(51)—C(45)—S(1) | 119.0(3) |
| C(45)—C(46)—C(47) | 119.8(4) |
| C(45)—C(46)—H(46) | 120.1 |
| C(47)—C(46)—H(46) | 120.1 |
| C(48)—C(47)—C(46) | 121.6(5) |
| C(48)—C(47)—H(47) | 119.2 |
| C(46)—C(47)—H(47) | 119.2 |
| C(47)—C(48)—C(50) | 117.4(4) |
| C(47)—C(48)—C(49) | 120.0(6) |
| C(50)—C(48)—C(49) | 122.6(6) |
| C(48)—C(49)—H(49A) | 109.5 |
| C(48)—C(49)—H(49B) | 109.5 |
| H(49A)—C(49)—H(49B) | 109.5 |
| C(48)—C(49)—H(49C) | 109.5 |
| H(49A)—C(49)—H(49C) | 109.5 |
| H(49B)—C(49)—H(49C) | 109.5 |
| C(51)—C(50)—C(48) | 121.7(4) |
| C(51)—C(50)—H(50) | 119.2 |
| C(48)—C(50)—H(50) | 119.2 |
| C(50)—C(51)—C(45) | 119.8(4) |
| C(50)—C(51)—H(51) | 120.1 |
| C(45)—C(51)—H(51) | 120.1 |
| C(53)—C(52)—C(58) | 120.0(4) |
| C(53)—C(52)—S(2) | 119.2(3) |
| C(58)—C(52)—S(2) | 120.8(3) |
| C(52)—C(53)—C(54) | 119.1(4) |
| C(52)—C(53)—H(53) | 120.5 |
| C(54)—C(53)—H(53) | 120.5 |
| C(55)—C(54)—C(53) | 121.7(4) |
| C(55)—C(54)—H(54) | 119.1 |
| C(53)—C(54)—H(54) | 119.2 |
| C(54)—C(55)—C(57) | 118.7(4) |
| C(54)—C(55)—C(56) | 120.8(6) |
| C(57)—C(55)—C(56) | 120.5(6) |
| C(55)—C(56)—H(56A) | 109.5 |
| C(55)—C(56)—H(56B) | 109.5 |
| H(56A)—C(56)—H(56B) | 109.5 |
| C(55)—C(56)—H(56C) | 109.5 |
| H(56A)—C(56)—H(56C) | 109.5 |
| H(56B)—C(56)—H(56C) | 109.5 |
| C(58)—C(57)—C(55) | 120.3(5) |
| C(58)—C(57)—H(57) | 119.9 |
| C(55)—C(57)—H(57) | 119.8 |
| C(57)—C(58)—C(52) | 120.3(4) |
| C(57)—C(58)—H(58) | 119.9 |
| C(52)—C(58)—H(58) | 119.9 |
| C(60)—O(13)—H(13) | 111.2 |
| O(13)—C(60)—C(59) | 84.0(16) |
| O(13)—C(60)—H(60A) | 114.8 |
| C(59)—C(60)—H(60A) | 115.0 |
| O(13)—C(60)—H(60B) | 114.1 |
| C(59)—C(60)—H(60B) | 114.6 |
| H(60A)—C(60)—H(60B) | 111.8 |
| C(60)—C(59)—H(59A) | 110.1 |
| C(60)—C(59)—H(59B) | 109.6 |
| H(59A)—C(59)—H(59B) | 109.1 |
| C(60)—C(59)—H(59C) | 110.1 |
| H(59A)—C(59)—H(59C) | 109.0 |
| H(59B)—C(59)—H(59C) | 109.0 |
| C(62)—O(14)—H(14A) | 119.8 |
| O(14)—C(62)—C(61) | 118.8(17) |
| O(14)—C(62)—H(62A) | 108.6 |
| C(61)—C(62)—H(62A) | 107.9 |
| O(14)—C(62)—H(62B) | 106.7 |
| C(61)—C(62)—H(62B) | 107.3 |
| H(62A)—C(62)—H(62B) | 107.1 |
| C(62)—C(61)—H(61A) | 109.4 |
| C(62)—C(61)—H(61B) | 109.1 |
| H(61A)—C(61)—H(61B) | 109.5 |
| C(62)—C(61)—H(61C) | 109.9 |
| H(61A)—C(61)—H(61C) | 109.5 |
| H(61B)—C(61)—H(61C) | 109.5 |

TABLE D4

Anisotropic displacement parameters(Å$^2$ × 10$^3$) for Example 4, p-toluenesulfonate salt. The anisotropic displacement factor exponent takes the form: $-2\pi^2[h^2 a^{*2}U^{11} + \ldots + 2 h k a^* b^* U^{12}]$.

| | $U^{11}$ | $U^{22}$ | $U^{33}$ | $U^{23}$ | $U^{13}$ | $U^{12}$ |
|---|---|---|---|---|---|---|
| S(1) | 59(1) | 51(1) | 57(1) | 4(1) | −8(1) | −18(1) |
| S(2) | 58(1) | 51(1) | 54(1) | 3(1) | −9(1) | −16(1) |
| F(1) | 84(2) | 64(1) | 85(2) | −24(1) | −16(1) | −24(1) |
| F(2) | 74(2) | 66(1) | 82(2) | −25(1) | 12(1) | −14(1) |
| N(1) | 41(1) | 57(2) | 76(2) | −20(1) | −1(1) | −16(1) |
| N(2) | 48(1) | 44(1) | 52(2) | −3(1) | −2(1) | −9(1) |
| N(3) | 57(2) | 42(1) | 50(2) | −4(1) | −1(1) | −10(1) |
| N(4) | 49(1) | 43(1) | 50(2) | −3(1) | −1(1) | −12(1) |
| N(5) | 56(2) | 42(1) | 45(1) | −4(1) | −3(1) | −20(1) |
| N(6) | 54(2) | 41(1) | 48(1) | −2(1) | −1(1) | −11(1) |
| N(7) | 41(1) | 51(2) | 80(2) | −16(1) | −4(1) | −15(1) |
| N(8) | 46(1) | 42(1) | 52(2) | 0(1) | −3(1) | −8(1) |
| N(9) | 59(2) | 41(1) | 50(2) | −2(1) | −7(1) | −12(1) |
| N(10) | 54(2) | 40(1) | 52(2) | −4(1) | −7(1) | −12(1) |
| N(11) | 45(1) | 43(1) | 47(1) | −4(1) | −4(1) | −6(1) |
| N(12) | 62(2) | 42(1) | 48(1) | −1(1) | −10(1) | −16(1) |
| O(1) | 37(1) | 40(1) | 78(2) | −12(1) | −7(1) | −8(1) |
| O(2) | 34(1) | 43(1) | 70(2) | −19(1) | −7(1) | −6(1) |
| O(3) | 83(2) | 51(1) | 56(1) | −6(1) | −2(1) | −35(1) |
| O(4) | 40(1) | 40(1) | 77(2) | −14(1) | −8(1) | −7(1) |
| O(5) | 37(1) | 46(1) | 67(2) | −19(1) | −8(1) | −8(1) |
| O(6) | 58(1) | 51(1) | 56(1) | −7(1) | −6(1) | 3(1) |
| O(7) | 89(3) | 118(3) | 93(3) | 28(2) | 21(2) | −11(2) |
| O(8) | 118(3) | 52(1) | 72(2) | 4(1) | −43(2) | −32(2) |
| O(9) | 86(2) | 51(1) | 88(2) | 6(1) | −34(2) | −30(1) |
| O(10) | 85(2) | 57(2) | 74(2) | 9(1) | 24(1) | 3(1) |
| O(11) | 151(4) | 121(3) | 91(3) | 27(2) | −62(3) | −78(3) |
| O(12) | 61(2) | 48(1) | 89(2) | 8(1) | 11(1) | −7(1) |
| C(1) | 38(1) | 41(1) | 46(2) | −4(1) | −6(1) | −10(1) |
| C(2) | 48(2) | 38(1) | 88(3) | −13(2) | −3(2) | −6(1) |
| C(3) | 70(3) | 53(2) | 122(4) | −24(2) | −4(2) | −24(2) |
| C(4) | 37(2) | 51(2) | 68(2) | −12(2) | −4(1) | −5(1) |
| C(5) | 31(2) | 70(2) | 94(3) | −20(2) | −5(2) | −10(2) |
| C(6) | 38(2) | 67(2) | 100(3) | −24(2) | −4(2) | −21(2) |
| C(7) | 32(1) | 45(2) | 45(2) | −7(1) | −3(1) | −10(1) |
| C(8) | 31(1) | 41(1) | 59(2) | −12(1) | −4(1) | −10(1) |
| C(9) | 41(2) | 47(2) | 49(2) | −8(1) | −2(1) | −12(1) |
| C(10) | 40(2) | 38(1) | 57(2) | −5(1) | −2(1) | −7(1) |
| C(11) | 32(1) | 42(1) | 52(2) | −5(1) | −1(1) | −12(1) |
| C(12) | 40(1) | 38(1) | 55(2) | −2(1) | −9(1) | −11(1) |
| C(13) | 37(1) | 42(1) | 51(2) | −2(1) | −2(1) | −13(1) |
| C(14) | 58(2) | 41(2) | 55(2) | −9(1) | 1(2) | −13(1) |
| C(15) | 42(2) | 45(2) | 51(2) | −3(1) | −1(1) | −17(1) |
| C(16) | 52(2) | 44(2) | 51(2) | 0(1) | −2(1) | −16(1) |
| C(17) | 45(2) | 45(2) | 50(2) | −4(1) | −2(1) | −15(1) |
| C(18) | 46(2) | 37(1) | 48(2) | −5(1) | −4(1) | −12(1) |
| C(19) | 54(2) | 47(2) | 48(2) | −5(1) | −2(1) | −19(1) |
| C(20) | 64(2) | 57(2) | 57(2) | 3(2) | −15(2) | −9(2) |
| C(21) | 56(2) | 62(2) | 64(2) | −6(2) | −16(2) | −14(2) |
| C(22) | 45(2) | 52(2) | 64(2) | −5(1) | −4(1) | −14(2) |
| C(23) | 37(1) | 43(1) | 44(1) | −5(1) | −4(1) | −9(1) |
| C(24) | 52(2) | 39(2) | 80(3) | −10(2) | 0(2) | −9(1) |

TABLE D4-continued

Anisotropic displacement parameters(Å² × 10³) for Example 4, p-toluenesulfonate salt. The anisotropic displacement factor exponent takes the form: $-2\pi^2[h^2 a^{*2}U^{11} + \ldots + 2 h k a^* b^* U^{12}]$.

| | $U^{11}$ | $U^{22}$ | $U^{33}$ | $U^{23}$ | $U^{13}$ | $U^{12}$ |
|---|---|---|---|---|---|---|
| C(25) | 65(2) | 53(2) | 133(4) | −22(2) | −9(3) | −20(2) |
| C(26) | 41(2) | 52(2) | 61(2) | −9(1) | −4(1) | −6(1) |
| C(27) | 33(2) | 71(2) | 92(3) | −20(2) | −5(2) | −11(2) |
| C(28) | 42(2) | 73(2) | 106(3) | −31(2) | 0(2) | −23(2) |
| C(29) | 35(1) | 44(1) | 44(2) | −7(1) | −4(1) | −8(1) |
| C(30) | 30(1) | 41(1) | 58(2) | −13(1) | −4(1) | −9(1) |
| C(31) | 40(2) | 50(2) | 49(2) | −7(1) | −2(1) | −12(1) |
| C(32) | 41(2) | 39(1) | 52(2) | −7(1) | −4(1) | −7(1) |
| C(33) | 34(1) | 43(1) | 50(2) | −5(1) | −6(1) | −12(1) |
| C(34) | 39(2) | 38(1) | 55(2) | −2(1) | −10(1) | −9(1) |
| C(35) | 37(1) | 40(1) | 50(2) | −5(1) | −7(1) | −9(1) |
| C(36) | 56(2) | 40(2) | 54(2) | −6(1) | −6(2) | −9(1) |
| C(37) | 41(2) | 45(2) | 47(2) | −1(1) | −9(1) | −11(1) |
| C(38) | 55(2) | 39(2) | 52(2) | 0(1) | −10(1) | −11(1) |
| C(39) | 42(2) | 41(1) | 53(2) | −5(1) | −5(1) | −10(1) |
| C(40) | 43(2) | 37(1) | 46(2) | −5(1) | −4(1) | −9(1) |
| C(41) | 50(2) | 42(1) | 47(2) | −5(1) | −4(1) | −9(1) |
| C(42) | 83(3) | 56(2) | 53(2) | 4(2) | 1(2) | −30(2) |
| C(43) | 60(2) | 64(2) | 67(2) | −8(2) | 9(2) | −30(2) |
| C(44) | 51(2) | 60(2) | 61(2) | −8(2) | −3(2) | −24(2) |
| C(45) | 45(2) | 49(2) | 54(2) | 2(1) | −11(1) | −15(1) |
| C(46) | 80(3) | 68(2) | 65(3) | −11(2) | −11(2) | −22(2) |
| C(47) | 85(3) | 94(3) | 53(2) | 3(2) | −12(2) | −35(3) |
| C(48) | 57(2) | 100(3) | 77(3) | 31(2) | −27(2) | −44(2) |
| C(49) | 85(3) | 151(6) | 109(4) | 68(4) | −42(3) | −69(4) |
| C(50) | 61(2) | 59(2) | 106(4) | 15(2) | −25(2) | −25(2) |
| C(51) | 55(2) | 46(2) | 74(2) | −1(2) | −11(2) | −15(1) |
| C(52) | 44(2) | 53(2) | 55(2) | 4(1) | −7(1) | −19(1) |
| C(53) | 53(2) | 53(2) | 73(3) | −1(2) | −6(2) | −17(2) |
| C(54) | 57(2) | 55(2) | 95(4) | 15(2) | −14(2) | −20(2) |
| C(55) | 50(2) | 98(3) | 84(3) | 37(3) | −22(2) | −39(2) |
| C(56) | 82(3) | 154(6) | 110(4) | 76(4) | −42(3) | −69(4) |
| C(57) | 81(3) | 110(4) | 60(3) | 5(2) | −6(2) | −46(3) |
| C(58) | 68(2) | 65(2) | 64(3) | −1(2) | −6(2) | −19(2) |
| O(13) | 350(30) | 59(6) | 91(8) | 3(5) | −14(12) | −21(11) |
| C(60) | 590(80) | 62(10) | 75(13) | 32(9) | −40(20) | −120(20) |
| C(59) | 72(10) | 101(12) | 200(20) | 78(13) | −16(12) | −9(9) |
| O(14) | 350(40) | 87(10) | 139(15) | 51(9) | −76(19) | −60(16) |
| C(62) | 121(17) | 83(12) | 160(20) | 38(12) | −63(16) | −15(11) |
| O(61) | 114(12) | 76(9) | 133(14) | 39(9) | −40(11) | −55(9) |

Example 5

2-{5-[(3-Ethoxypyridin-2-yl)oxy]pyridin-3-yl}-N-[(3R,4R)-4-fluoropiperidin-3-yl]pyrimidine-5-carboxamide (5)

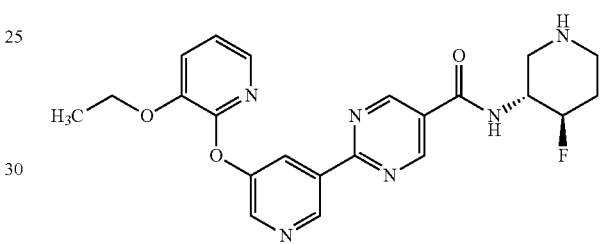

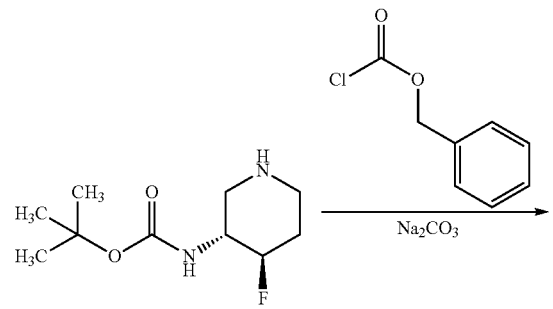

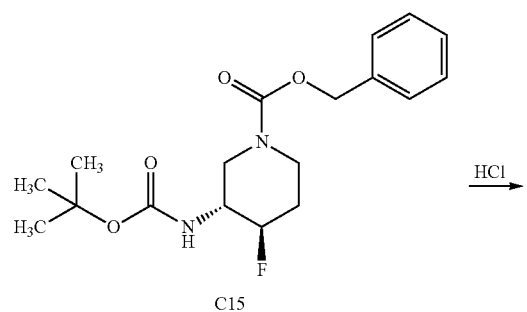

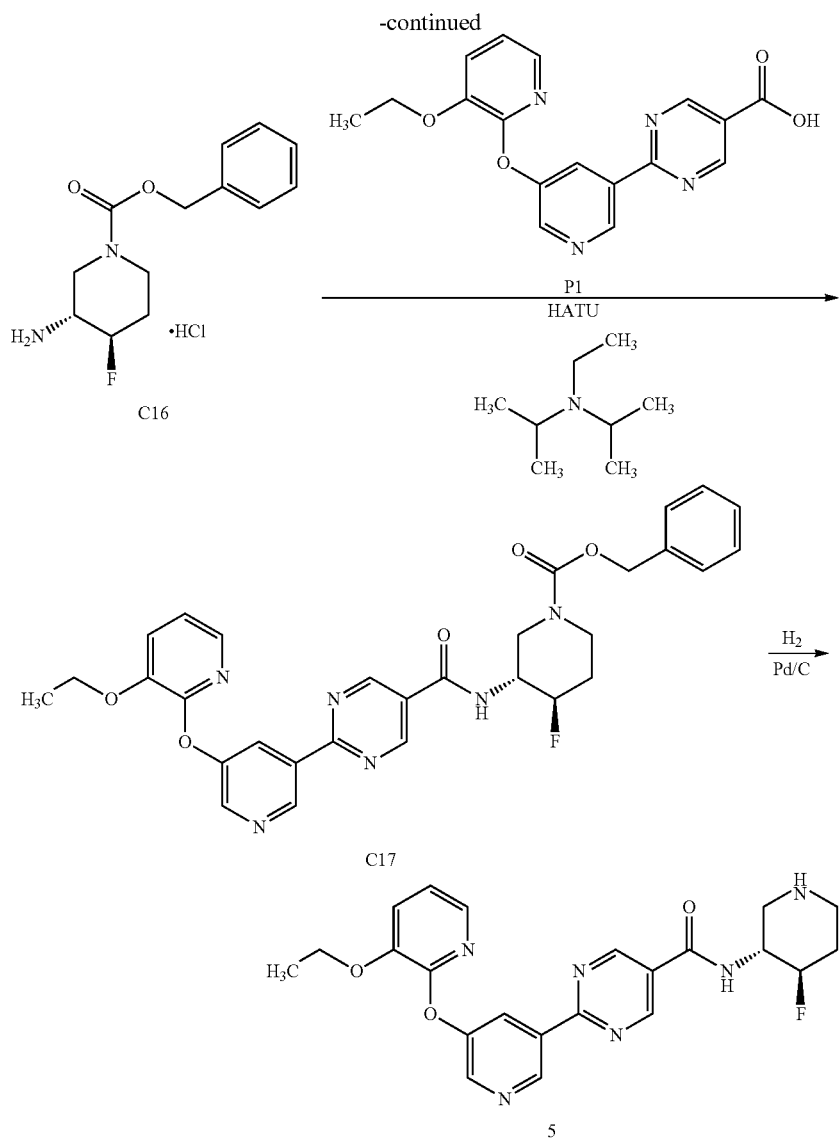

Step 1. Synthesis of benzyl (3R,4R)-3-[(tert-butoxycarbonyl)amino]-4-fluoropiperidine-1-carboxylate (C15)

Benzyl chloroformate (258 mg, 1.51 mmol) was added to a 0° C. mixture of tert-butyl [(3R,4R)-4-fluoropiperidin-3-yl]carbamate (300 mg, 1.37 mmol) in tetrahydrofuran (15 mL) and aqueous sodium carbonate solution (1 M; 2.75 mL, 2.75 mmol). After the reaction mixture had been stirred at 15° C. for 16 hours, water (20 mL) was added, and the resulting mixture was extracted with ethyl acetate (2×30 mL). The combined organic layers were washed with saturated aqueous sodium chloride solution (50 mL), dried over sodium sulfate, filtered, and concentrated in vacuo to provide C15 as a white solid. Yield: 485 mg, 1.38 mmol, quantitative. $^1$H NMR (400 MHz, chloroform-d) δ 7.43-7.28 (m, 5H), 5.14 (AB quartet, $J_{AB}$=12.3 Hz, $\Delta v_{AB}$=14.2 Hz, 2H; downfield doublet is broadened), 4.83-4.53 (m, 2H), 3.87-3.33 (m, 4H), 2.06-1.75 (m, 2H), 1.44 (s, 9H).

Step 2. Synthesis of benzyl (3R,4R)-3-amino-4-fluoropiperidine-1-carboxylate, hydrochloride Salt (C16)

A solution of C15 (485 mg, 1.38 mmol) in methanol (6 mL) was treated with hydrogen chloride (solution in ethyl acetate; 12 mL). After the reaction mixture had been stirred at 20° C. for 1 hour, it was concentrated in vacuo, affording C16 as a white solid. Yield: 370 mg, 1.28 mmol, 93%. $^1$H NMR (400 MHz, deuterium oxide) δ 7.50-7.39 (m, 5H), 5.17 (s, 2H), 4.93-4.71 (m, 1H, assumed; partially obscured by solvent peak), 4.42-4.27 (m, 1H), 4.24-3.98 (m, 1H), 3.51-3.39 (m, 1H), 3.21-2.99 (m, 2H), 2.29-2.16 (m, 1H), 1.86-1.71 (m, 1H).

Step 3. Synthesis of benzyl (3R,4R)-3-{[(2-{5-[(3-ethoxypyridin-2-yl)oxy]pyridin-3-yl}pyrimidin-5-yl)carbonyl]amino}-4-fluoropiperidine-1-carboxylate (C17)

To a mixture of P1 (170 mg, 0.502 mmol), C16 (145 mg, 0.502 mmol), and N,N-diisopropylethylamine (0.263 mL, 1.51 mmol) in N,N-dimethylformamide (8 mL) was added O-(7-azabenzotriazol-1-yl)-N,N,N',N'-tetramethyluronium hexafluorophosphate (HATU; 287 mg, 0.755 mmol). The reaction mixture was stirred at 18° C. for 2 hours, whereupon it was combined with two similar reactions carried out using C16 (42.7 mg, 0.148 mmol and 171 mg, 0.592 mmol), diluted with water (50 mL), and extracted with ethyl acetate (30 mL). The organic layer was washed with saturated aqueous sodium chloride solution (50 mL), dried over sodium sulfate, filtered, and concentrated under reduced pressure. Upon silica gel chromatography (Gradient: 0% to 100% ethyl acetate in petroleum ether), C17 was obtained as a yellow solid. Combined yield: 540 mg, 0.943 mmol, 76%. LCMS m/z 573.1 [M+H]$^+$.

Step 4. Synthesis of 2-{5-[(3-ethoxypyridin-2-yl)oxy]pyridin-3-yl}-N-[(3R,4R)-4-fluoropiperidin-3-yl]pyrimidine-5-carboxamide (5)

A mixture of C17 (300 mg, 0.524 mmol) and 10% palladium on carbon (300 mg) in ethanol (20 mL) was stirred under a balloon of hydrogen for 2 hours at 15° C. After the reaction mixture had been combined with two similar reactions carried out using C17 (200 mg, 0.349 mmol and 40 mg, 70 μmol), it was filtered through a pad of diatomaceous earth. The filtrate was concentrated, and the residue was purified using reversed-phase HPLC (Column: Agela Durashell C18, 5 μm; Mobile phase A: 0.05% ammonium hydroxide in water; Mobile phase B: acetonitrile; Gradient: 30% to 50% B), affording 2-{5-[(3-ethoxypyridin-2-yl)oxy]pyridin-3-yl}-N-[(3R,4R)-4-fluoropiperidin-3-yl]pyrimidine-5-carboxamide as a white solid. Combined yield: 174 mg, 0.397 mmol, 42%. LCMS m/z 439.2 [M+H]$^+$. $^1$H NMR (400 MHz, chloroform-d) δ 9.52 (d, J=1.8 Hz, 1H), 9.20 (s, 2H), 8.65 (d, J=2.8 Hz, 1H), 8.56 (dd, J=2.7, 1.8 Hz, 1H), 7.71 (dd, J=4.9, 1.5 Hz, 1H), 7.28-7.23 (m, 1H, assumed; partially obscured by solvent peak), 7.17 (br d, J=8 Hz, 1H), 7.02 (dd, J=7.9, 4.9 Hz, 1H), 4.86-4.66 (m, 1H), 4.37-4.26 (m, 1H), 4.18 (q, J=7.0 Hz, 2H), 3.36 (ddd, J=12.3, 3.4, 3.4 Hz, 1H), 3.09-2.99 (m, 1H), 2.86-2.75 (m, 2H), 2.11-1.81 (m, 2H), 1.50 (t, J=7.0 Hz, 3H).

Example 6

2-{5-[(3-Ethoxy-5-fluoropyridin-2-yl)oxy]pyridin-3-yl}-N-[(3R,4R)-4-fluoropiperidin-3-yl]pyrimidine-5-carboxamide (6)

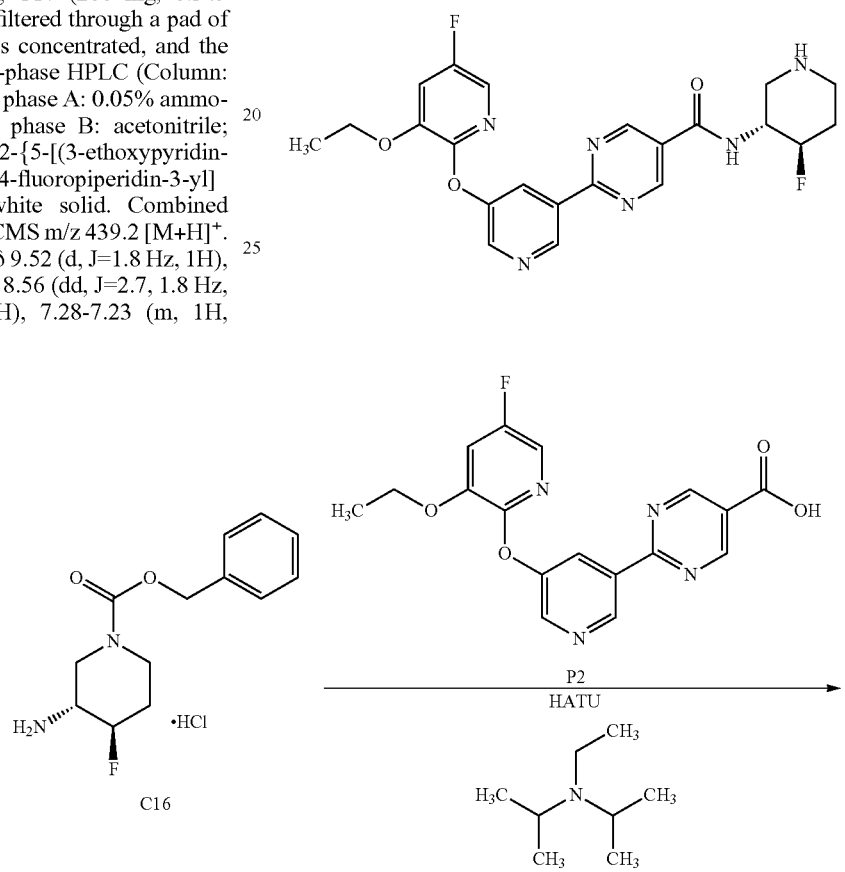

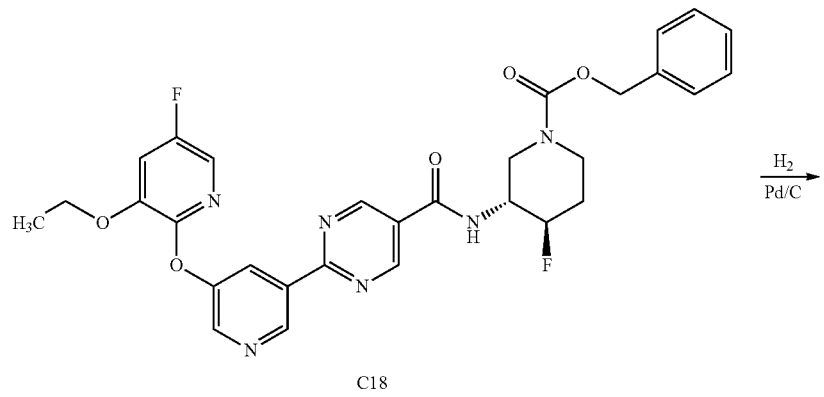

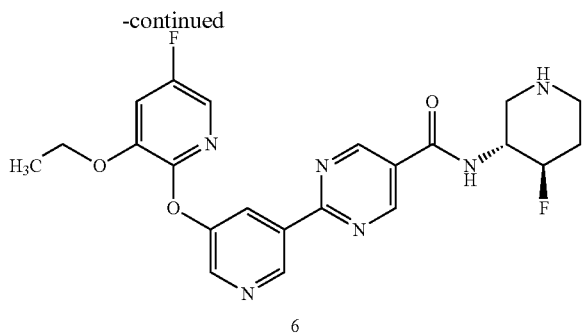

6

Step 1. Synthesis of benzyl (3R,4R)-3-{[(2-{5-[(3-ethoxy-5-fluoropyridin-2-yl)oxy]pyridin-3-yl}pyrimidin-5-yl)carbonyl]amino}-4-fluoropiperidine-1-carboxylate (C18)

To a mixture of P2 (50 mg, 0.14 mmol), C16 (40.5 mg, 0.140 mmol), and N,N-diisopropylethylamine (73.3 µL, 0.421 mmol) in N,N-dimethylformamide (2 mL) was added 0-(7-azabenzotriazol-1-yl)-N,N,N',N'-tetramethyluronium hexafluorophosphate (HATU; 80 mg, 0.21 mmol). After the reaction mixture had been stirred at 18° C. for 2 hours, it was combined with a similar reaction carried out using C16 (24.3 mg, 84.2 µmol), then quenched with water (20 mL) and extracted with ethyl acetate (20 mL). The organic layer was washed with saturated aqueous sodium chloride solution (50 mL), dried over sodium sulfate, filtered, and concentrated in vacuo. Purification of the residue via preparative thin-layer chromatography (Eluent: ethyl acetate) afforded C18 as a yellow solid. Combined yield: 90 mg, 0.152 mmol, 68%. LCMS m/z 591.1 [M+H]$^+$.

Step 2. Synthesis of 2-{5-[(3-ethoxy-5-fluoropyridin-2-yl)oxy]pyridin-3-yl}-N-[(3R,4R)-4-fluoropiperidin-3-yl]pyrimidine-5-carboxamide (6)

A mixture of C18 (70 mg, 0.12 mmol) and 10% palladium on carbon (100 mg) in ethanol (20 mL) was stirred under a balloon of hydrogen for 2 hours at 15° C., whereupon it was combined with a similar reaction carried out using C18 (20 mg, 34 µmol) and filtered through a pad of diatomaceous earth. After the filtrate had been concentrated in vacuo, the residue was purified using reversed-phase HPLC (Column: Agela Durashell C18, 5 µm; Mobile phase A: 0.05% ammonium hydroxide in water; Mobile phase B: acetonitrile; Gradient: 30% to 50% B); this afforded 2-{5-[(3-ethoxy-5-fluoropyridin-2-yl)oxy]pyridin-3-yl}-N-[(3R,4R)-4-fluoropiperidin-3-yl]pyrimidine-5-carboxamide as a white solid. Yield: 14.2 mg, 31.1 µmol, 20%. LCMS m/z 457.1 [M+H]$^+$.
$^1$H NMR (400 MHz, chloroform-d) δ 9.52 (d, J=1.8 Hz, 1H), 9.20 (s, 2H), 8.63 (d, J=2.7 Hz, 1H), 8.53 (dd, J=2.7, 1.8 Hz, 1H), 7.58 (d, J=2.6 Hz, 1H), 7.16-7.09 (br m, 1H), 7.06 (dd, J=9.2, 2.6 Hz, 1H), 4.86-4.68 (m, J$_{HF}$=47.2 Hz, 1H), 4.37-4.27 (m, 1H), 4.16 (q, J=7.0 Hz, 2H), 3.36 (ddd, J=12.2, 3.5, 3.4 Hz, 1H), 3.09-2.99 (m, 1H), 2.87-2.76 (m, 2H), 2.11-1.82 (m, 2H), 1.51 (t, J=7.0 Hz, 3H).

Examples 7-25

TABLE 1

Method of synthesis and structure for Examples 7-25. The examples below were made from analogous processes to the Example(s) identified and from appropriate analogous starting materials.

| Example Number | Method of synthesis; Non-commercial starting materials | Structure |
|---|---|---|
| 7 | Example 5$^1$; P1 | (structure shown: pyridine-ethoxy-pyridine-pyrimidine-carboxamide-fluoropiperidine · CF$_3$COOH) |

TABLE 1-continued

Method of synthesis and structure for Examples 7-25. The examples below were made from analogous processes to the Example(s) identified and from appropriate analogous starting materials.

| Example Number | Method of synthesis; Non-commercial starting materials | Structure |
|---|---|---|
| 8 | Example 1[2,3,4]; P1 | (structure, +/-) or (structure, +/-) |
| 9 | Example 1[2,3,4]; P1 | (structure, +/-) or (structure, +/-) |
| 10 | Example 9[5] | (structure, •CF$_3$COOH) one enantiomer from Example 9; ENT-1 |

TABLE 1-continued

Method of synthesis and structure for Examples 7-25. The examples below were made from analogous processes to the Example(s) identified and from appropriate analogous starting materials.

| Example Number | Method of synthesis; Non-commercial starting materials | Structure |
|---|---|---|
| 11 | Example 9[5] | 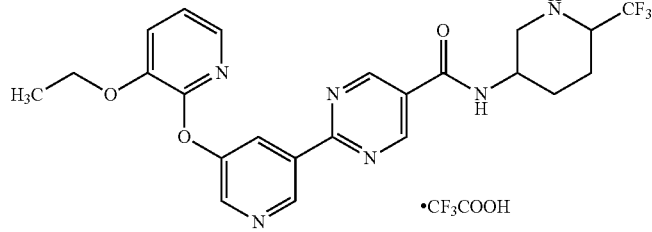<br>one enantiomer from Example 9; ENT-2 |
| 12 | Example 1; P1 | 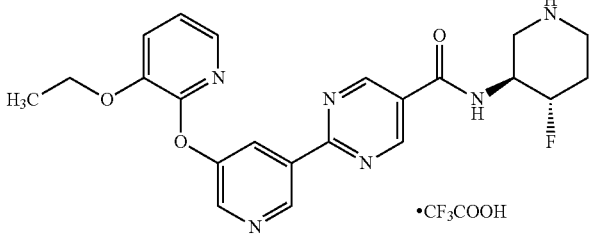 |
| 13 | Example 5[6]; P2 | 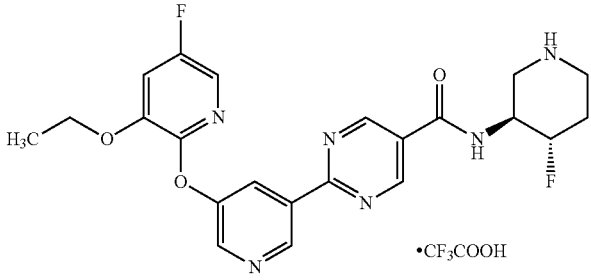 |
| 14 | Example 5[1]; P1 | 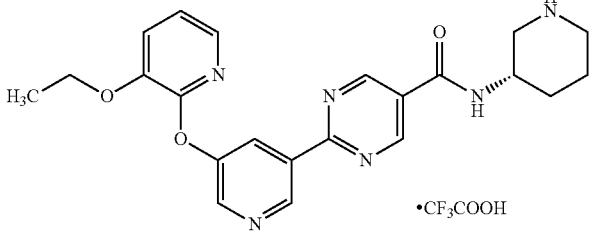 |
| 15 | Example 14[7]; P1 | 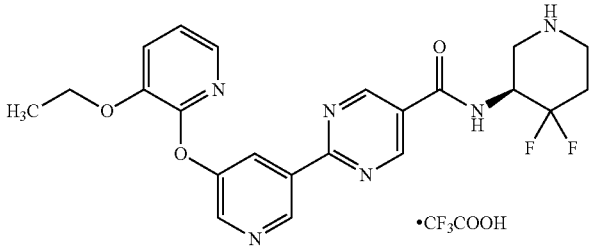<br>or |

103
104

TABLE 1-continued

Method of synthesis and structure for Examples 7-25. The examples below were
made from analogous processes to the Example(s) identified and from appropriate analogous
starting materials.

| Example Number | Method of synthesis; Non-commercial starting materials | Structure |
|---|---|---|
| | | 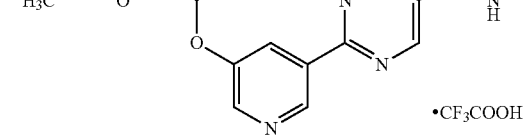From first-eluting enantiomer of intermediate (see footnote 7) |
| 16 | Example 14[7]; P1 | 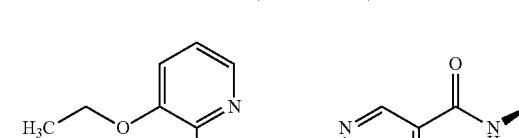or<br>From second-eluting enantiomer of intermediate (see footnote 9) |
| 17 | Example 1[1,3]; P1 | 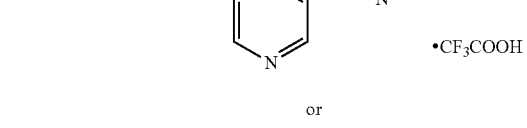 |
| 18 | Example 17[8] | 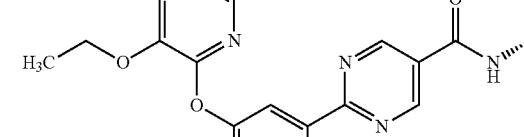or |

TABLE 1-continued

Method of synthesis and structure for Examples 7-25. The examples below were made from analogous processes to the Example(s) identified and from appropriate analogous starting materials.

| Example Number | Method of synthesis; Non-commercial starting materials | Structure |
|---|---|---|
| 19 | Example 17[8] | ENT-1 or ENT-2 |
| 20 | Example 14; P1 | (+/−) •CF₃COOH |
| 21 | Example 14; P1 | •CF₃COOH |

// 107  108
TABLE 1-continued
Method of synthesis and structure for Examples 7-25. The examples below were made from analogous processes to the Example(s) identified and from appropriate analogous starting materials.
| Example Number | Method of synthesis; Non-commercial starting materials | Structure |
|---|---|---|
| 22 | Example 14; P1 | 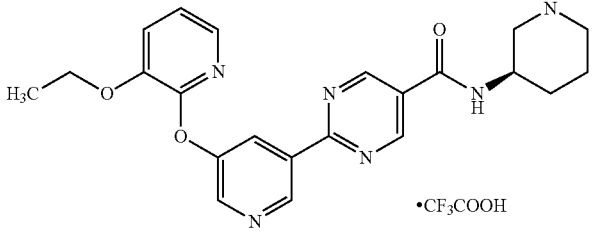 |
| 23 | Example 14; P1 | 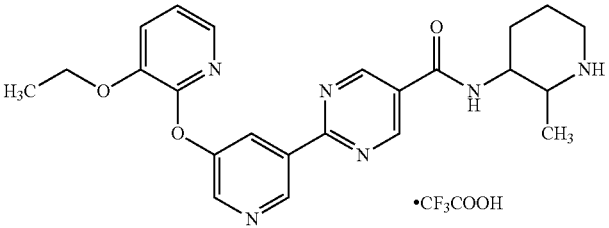<br>mixture of stereoisomers |
| 24 | Example 14; P1 | 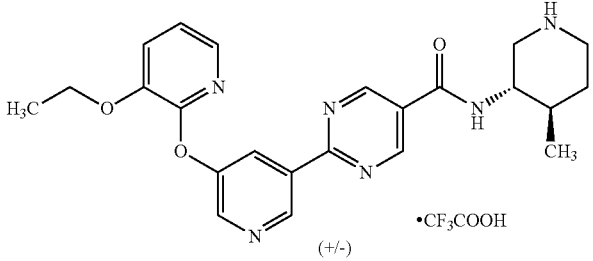 |

TABLE 1-continued

Method of synthesis and structure for Examples 7-25. The examples below were made from analogous processes to the Example(s) identified and from appropriate analogous starting materials.

| Example Number | Method of synthesis; Non-commercial starting materials | Structure |
|---|---|---|
| 25 | Example 5[9]; P1 | [structure: 2-{5-[(3-ethoxypyridin-2-yl)oxy]pyridin-3-yl}-N-[(3R,5S)-5-fluoropiperidin-3-yl]pyrimidine-5-carboxamide · CF₃COOH (+/−)] |

[1]In this case, the nitrogen of the piperidine side chain reagent was protected with a tert-butoxycarbonyl group. After the amide coupling reaction, the product was deprotected using trifluoroacetic acid.
[2]Reaction of benzyl chloroformate with tert-butyl [6-(trifluoromethyl)piperidin-3-yl]carbamate in the presence of N,N-diisopropylethylamine provided benzyl 5-[(tert-butoxycarbonyl)amino]-2-(trifluoromethyl)piperidine-1-carboxylate, which was deprotected with trifluoroacetic acid to afford the requisite benzyl 5-amino-2-(trifluoromethyl)piperidine-1-carboxylate as a mixture of stereoisomers.
[3]In this case, the amide coupling was mediated by 2-chloro-1-methylpyridinium iodide (Mukaiyama reagent) and triethylamine.
[4]The racemic cis and trans products were separated using reversed-phase HPLC (Column: Waters XBridge C18 OBD, 5 μm; Mobile phase A: water containing 0.04% ammonium hydroxide and 10 mM ammonium bicarbonate; Mobile phase B: acetonitrile; Gradient: 23% to 53% B). The first-eluting isomer was designated as Example 8, and the second-eluting isomer as Example 9.
[5]Example 9 was separated into its component enantiomers using supercritical fluid chromatography {Column: Phenomenex Lux Amylose-1, 5 μm; Mobile phase: 7:3 carbon dioxide/[ethanol containing 0.2% (7M ammonia in methanol)]}. The first-eluting enantiomer was designated as Example 10, and the second-eluting enantiomer as Example 11. Retention time for Example 10: 6.48 minutes [Column: Phenomenex Lux Amylose-1, 4.6 × 250 mm, 5 μm; Mobile phase A: carbon dioxide; Mobile phase B: ethanol containing 0.2% (7M ammonia in methanol); Gradient: 5% B for 1.0 minute, then 5% to 60% B over 8.0 minutes; Flow rate: 3.0 mL/minute; Back pressure: 120 bar]. Retention time for Example 11: 6.68 minutes (Analytical conditions identical to those used for Example 10). These two compounds are enantiomers of one another, but of undetermined relative and absolute stereochemistry.
[6]The piperidine side chain employed for Example 13 was tert-butyl (3S,4S)-3-amino-4-fluoropiperidine-1-carboxylate; after the amide coupling, deprotection was carried out using trifluoroacetic acid.
[7]Reaction of tert-butyl rac-(3R,4R)-3-amino-4-hydroxypiperidine-1-carboxylate with benzyl chloroformate and sodium carbonate, followed by oxidation of the product with 1,1,1-tris(acetyloxy)-1,1-dihydro-1,2-benziodoxol-3-(1H)-one (Dess-Martin periodinane), afforded tert-butyl 3-{[(benzyloxy)carbonyl]amino}-4-oxopiperidine-1-carboxylate. Difluorination of this material using (diethylamino)sulfur trifluoride provided tert-butyl 3-{[(benzyloxy)carbonyl]amino}-4,4-difluoropiperidine-1-carboxylate, which was separated into its component enantiomers via supercritical fluid chromatography [Column: Chiral Technologies Chiralpak AD, 10 μm; Mobile phase: 85:15 carbon dioxide/(ethanol containing 0.15% ammonium hydroxide)]. The first-eluting enantiomer had a retention time of 2.73 minutes (Column: Chiral Technologies Chiralcel OJ-H, 4.6 × 250 mm, 5 μm; Mobile phase A: carbon dioxide; Mobile phase B: ethanol containing 0.05% diethylamine; Gradient: 5% to 40% B over 5 minutes; Flow rate: 2.5 mL/minute). The second-eluting enantiomer exhibited a retention time of 3.08 minutes under the same conditions. The first-eluting enantiomer was deprotected by hydrogenation over palladium hydroxide, to afford one enantiomer of tert-butyl 3-amino-4,4-difluoropiperidine-1-carboxylate; this material exhibited a negative (−) rotation, and was used in the synthesis of Example 15. The second-eluting enantiomer was deprotected in the same manner to provide the other enantiomer of tert-butyl 3-amino-4,4-difluoropiperidine-1-carboxylate, which exhibited a positive (+) rotation, and was used in the synthesis of Example 16.
[8]Example 17 was separated into its component enantiomers using supercritical fluid chromatography [Column: Chiral Technologies Chiralpak IC, 5 μm; Mobile phase: 3:2 carbon dioxide/(ethanol containing 0.1% ammonium hydroxide)]. The first-eluting enantiomer was designated as Example 18, and gave a retention time of 3.42 minutes ([Column: Chiral Technologies Chiralpak IC, 3 μm; Mobile phase: 3:2 carbon dioxide/(ethanol containing 0.05% diethylamine); Flow rate 2.5 mL/minute]. The second-eluting enantiomer was designated as Example 19, and gave a retention time of 4.42 minutes (Analytical conditions identical to those used for Example @521).
[9]The piperidine side chain employed for Example 25 was tert-butyl rac-(3R,5S)-3-amino-5-fluoropiperidine-1-carboxylate; after the amide coupling, deprotection was carried out using trifluoroacetic acid.

TABLE 2

Compound name and physicochemical data for Examples 7-25.

| Example Number | Compound Name | ¹H NMR (400 MHz, CDCl₃) ; Mass spectrum, observed ion m/z [M + H]⁺ or HPLC retention time; Mass spectrum m/z [M + H]⁺ (unless otherwise indicated) |
|---|---|---|
| 7 | 2-{5-[(3-ethoxypyridin-2-yl)oxy]pyridin-3-yl}-N-[(3R,5R)-5-fluoropiperidin-3-yl]pyrimidine-5-carboxamide, trifluoroacetate salt | 1.82 minutes[1]; 439.1 |
| 8 | First-eluting isomer (see footnote 4 in Table 1); rac-2-{5-[(3-ethoxypyridin-2-yl)oxy]pyridin-3-yl}-N-[(3R,6S)-6-(trifluoromethyl)piperidin-3-yl]pyrimidine-5-carboxamide or rac-2-{5-[(3-ethoxypyridin-2-yl)oxy]pyridin-3-yl}-N-[(3R,6R)-6-(trifluoromethyl)piperidin-3-yl]pyrimidine-5-carboxamide | First-eluting isomer; characteristic peaks: 9.62-9.42 (m, 1H), 9.13 (s, 2H), 8.73-8.59 (m, 1H), 8.56 (s, 1H), 7.70 (dd, J = 5.0, 1.5 Hz, 1H), 7.29-7.22 (m, 1H, assumed; partially obscured by solvent peak), 7.03 (dd, J = 7.9, 4.9 Hz, 1H), 6.26 (br d, J = 7.7 Hz, 1H), 4.23-4.09 (m, 1H), 4.18 (q, J = 7.0 Hz, 2H), 3.51 (br d, J = 12 Hz, 1H), 3.24-3.12 (m, 1H), 2.63-2.54 (m, 1H), 2.29-2.18 (m, 1H), 2.08-1.96 (m, 1H), 1.78-1.66 (m, 1H), 1.50 (t, J = 7.0 Hz, 3H); 489.3 |
| 9 | Second-eluting isomer (see footnote 4 in Table 1); rac-2-{5-[(3-ethoxypyridin-2-yl)oxy]pyridin-3-yl}-N-[(3R,6S)-6- | Second-eluting isomer; 9.60-9.48 (m, 1H), 9.19 (s, 2H), 8.71-8.61 (m, 1H), 8.57 (br s, 1H), 7.71 (dd, J = 4.8, 1.5 Hz, 1H), 7.3-7.23 (m, 1H, assumed; partially obscured |

TABLE 2-continued

Compound name and physicochemical data for Examples 7-25.

| Example Number | Compound Name | $^1$H NMR (400 MHz, CDCl$_3$) ; Mass spectrum, observed ion m/z [M + H]$^+$ or HPLC retention time; Mass spectrum m/z [M + H]$^+$ (unless otherwise indicated) |
|---|---|---|
| | (trifluoromethyl)piperidin-3-yl]pyrimidine-5-carboxamide or rac-2-{5-[(3-ethoxypyridin-2-yl)oxy]pyridin-3-yl}-N-[(3R,6R)-6-(trifluoromethyl)piperidin-3-yl]pyrimidine-5-carboxamide | by solvent peak), 7.20 (br d, J = 7.8 Hz, 1H), 7.02 (dd, J = 7.9, 4.9 Hz, 1H), 4.40-4.32 (m, 1H), 4.18 (q, J = 7.0 Hz, 2H), 3.28-3.19 (m, 1H), 3.16 (br d, J = 12 Hz, 1H), 3.01 (br d, J = 12 Hz, 1H), 2.24-2.13 (m, 1H), 1.86-1.65 (m, 3H, assumed; partially obscured by water peak), 1.50 (t, J = 7.0 Hz, 3H); 489.3 |
| 10 | First-eluting enantiomer from separation of Example 9 (see footnote 5 in Table 1); 2-{5-[(3-ethoxypyridin-2-yl)oxy]pyridin-3-yl}-N-[6-(trifluoromethyl)piperidin-3-yl]pyrimidine-5-carboxamide, trifluoroacetate salt, ENT-1 | 1.91 minutes$^1$; 489.4 |
| 11 | Second-eluting enantiomer from separation of Example 9 (see footnote 5 in Table 1); 2-{5-[(3-ethoxypyridin-2-yl)oxy]pyridin-3-yl}-N-[6-(trifluoromethyl)piperidin-3-yl]pyrimidine-5-carboxamide, trifluoroacetate salt, ENT-2 | 1.91 minutes$^1$; 489.4 |
| 12 | 2-{5-[(3-ethoxypyridin-2-yl)oxy]pyridin-3-yl}-N-[(3S,4S)-4-fluoropiperidin-3-yl]pyrimidine-5-carboxamide, trifluoroacetate salt | 9.83 (br s, 2H), 9.63 (s, 1H), 9.35 (s, 2H), 9.12 (br d, J = 7.9 Hz, 1H), 9.05 (dd, J = 2.5, 1.5 Hz, 1H), 8.77 (d, J = 2.5 Hz, 1H), 7.70 (dd, J = 4.8, 1.5 Hz, 1H), 7.31 (dd, J = 8.0, 1.5 Hz, 1H), 7.12 (dd, J = 8.0, 4.8 Hz, 1H), 4.92 (br d, J$_{HF}$ = 46.1 Hz, 1H), 4.82-4.72 (m, 1H), 4.17 (q, J = 7.0 Hz, 2H), 3.58 (br AB quartet, J$_{AB}$ = 13 Hz, Δv$_{AB}$ = 55 Hz, 2H), 3.44-3.29 (m, 2H), 2.52-2.31 (m, 1H), 2.26-2.11 (m, 1H), 1.49 (t, J = 7.0 Hz, 3H); 439.4 |
| 13 | 2-{5-[(3-ethoxy-5-fluoropyridin-2-yl)oxy]pyridin-3-yl}-N-[(3S,4S)-4-fluoropiperidin-3-yl]pyrimidine-5-carboxamide, formate salt | Characteristic peaks: 9.48 (d, J = 1.7 Hz, 1H), 8.89 (s, 2H), 8.62 (d, J = 2.7 Hz, 1H), 8.52 (dd, J = 2.7, 1.7 Hz, 1H), 7.56 (d, J = 2.5 Hz, 1H), 7.05 (dd, J = 9.1, 2.5 Hz, 1H), 4.77-4.44 (m, 1H), 4.38-4.21 (m, 1H), 4.15 (q, J = 7.0 Hz, 2H), 3.44-3.34 (m, 1H), 2.30-2.12 (m, 1H), 1.95-1.71 (m, 1H), 1.50 (t, J = 7.0 Hz, 3H); 457.1 |
| 14 | 2-{5-[(3-ethoxypyridin-2-yl)oxy]pyridin-3-yl}-N-[(3S)-piperidin-3-yl]pyrimidine-5-carboxamide, trifluoroacetate salt | 2.29 minutes$^2$; 421 |
| 15 | From first-eluting enantiomer of intermediate (see footnote 7, Table 1); N-[(3S)-4,4-difluoropiperidin-3-yl]-2-{5-[(3-ethoxypyridin-2-yl)oxy]pyridin-3-yl}pyrimidine-5-carboxamide, trifluoroacetate salt or N-[(3R)-4,4-difluoropiperidin-3-yl]-2-{5-[(3-ethoxypyridin-2-yl)oxy]pyridin-3-yl}pyrimidine-5-carboxamide, trifluoroacetate salt | 2.50 minutes$^2$; 457 |
| 16 | From second-eluting enantiomer of intermediate (see footnote 7, Table 1); N-[(3S)-4,4-difluoropiperidin-3-yl]-2-{5-[(3-ethoxypyridin-2-yl)oxy]pyridin-3-yl}pyrimidine-5-carboxamide, trifluoroacetate salt or N-[(3R)-4,4-difluoropiperidin-3-yl]-2-{5-[(3-ethoxypyridin-2-yl)oxy]pyridin-3-yl}pyrimidine-5-carboxamide, trifluoroacetate salt | 2.48 minutes$^2$; 457 |
| 17 | N-(5,5-difluoropiperidin-3-yl)-2-{5-[(3-ethoxypyridin-2-yl)oxy]pyridin-3-yl}pyrimidine-5-carboxamide | 9.51 (d, J = 1.8 Hz, 1H), 9.16 (s, 2H), 8.65 (d, J = 2.8 Hz, 1H), 8.58-8.54 (m, 1H), 7.71 (br d, J = 4.8 Hz, 1H), 7.3-7.23 (m, 1H, assumed; partially obscured by solvent peak), 7.02 (dd, J = 7.9, 4.8 Hz, 1H), 6.96 |

TABLE 2-continued

Compound name and physicochemical data for Examples 7-25.

| Example Number | Compound Name | $^1$H NMR (400 MHz, CDCl$_3$) ; Mass spectrum, observed ion m/z [M + H]$^+$ or HPLC retention time; Mass spectrum m/z [M + H]$^+$ (unless otherwise indicated) |
|---|---|---|
| | | (br d, J = 8.5 Hz, 1H), 4.58-4.48 (m, 1H), 4.18 (q, J = 7.0 Hz, 2H), 3.28-3.16 (m, 1H), 3.07-2.89 (m, 3H), 2.39-2.12 (m, 2H), 1.50 (t, J = 7.0 Hz, 3H); 457.4 |
| 18 | First-eluting enantiomer (see footnote 8 in Table 1); N-[(3S)-5,5-difluoropiperidin-3-yl]-2-{5-[(3-ethoxypyridin-2-yl)oxy]pyridin-3-yl}pyrimidine-5-carboxamide or N-[(3R)-5,5-difluoropiperidin-3-yl]-2-{5-[(3-ethoxypyridin-2-yl)oxy]pyridin-3-yl}pyrimidine-5-carboxamide | 9.55-9.49 (m, 1H), 9.16 (s, 2H), 8.68-8.62 (m, 1H), 8.56 (br s, 1H), 7.71 (br d, J = 5.0 Hz, 1H), 7.3-7.23 (m, 1H, assumed; partially obscured by solvent peak), 7.02 (dd, J = 7.9, 4.9 Hz, 1H), 6.95 (br d, J = 8 Hz, 1H), 4.58-4.49 (m, 1H), 4.18 (q, J = 7.0 Hz, 2H), 3.28-3.17 (m, 1H), 3.08-2.89 (m, 3H), 2.39-2.11 (m, 2H), 1.50 (t, J = 7.0 Hz, 3H); 457.4 |
| 19 | Second-eluting enantiomer(see footnote 8 in Table 1); N-[(3S)-5,5-difluoropiperidin-3-yl]-2-{5-[(3-ethoxypyridin-2-yl)oxy]pyridin-3-yl}pyrimidine-5-carboxamide or N-[(3R)-5,5-difluoropiperidin-3-yl]-2-{5-[(3-ethoxypyridin-2-yl)oxy]pyridin-3-yl}pyrimidine-5-carboxamide | 9.52 (d, J = 1.7 Hz, 1H), 9.16 (s, 2H), 8.65 (d, J = 2.7 Hz, 1H), 8.56 (dd, J = 2, 2 Hz, 1H), 7.73-7.69 (m, 1H), 7.3-7.23 (m, 1H, assumed; partially obscured by solvent peak), 7.03 (dd, J = 7.9, 5.0 Hz, 1H), 6.92 (br d, J = 8 Hz, 1H), 4.57-4.49 (m, 1H), 4.18 (q, J = 7.0 Hz, 2H), 3.28-3.17 (m, 1H), 3.06-2.89 (m, 3H), 2.39-2.12 (m, 2H), 1.50 (t, J = 7.0 Hz, 3H); 457.4 |
| 20 | rac-2-{5-[(3-ethoxypyridin-2-yl)oxy]pyridin-3-yl}-N-[(3R,4R)-4-methylpiperidin-3-yl]pyrimidine-5-carboxamide, trifluoroacetate salt | 2.38 minutes$^2$; 435 |
| 21 | 2-{5-[(3-ethoxypyridin-2-yl)oxy]pyridin-3-yl}-N-(piperidin-3-yl)pyrimidine-5-carboxamide, trifluoroacetate salt | 2.37 minutes$^2$; 421 |
| 22 | 2-{5-[(3-ethoxypyridin-2-yl)oxy]pyridin-3-yl}-N-[(3R)-piperidin-3-yl]pyrimidine-5-carboxamide, trifluoroacetate salt | 2.64 minutes$^2$; 421 |
| 23 | 2-{5-[(3-ethoxypyridin-2-yl)oxy]pyridin-3-yl}-N-(2-methylpiperidin-3-yl)pyrimidine-5-carboxamide, trifluoroacetate salt, mixture of stereoisomers | 2.39 minutes$^2$; 435 |
| 24 | rac-2-{5-[(3-ethoxypyridin-2-yl)oxy]pyridin-3-yl}-N-[(3R,4S)-4-methylpiperidin-3-yl]pyrimidine-5-carboxamide, trifluoroacetate salt | 2.42 minutes$^2$; 435 |
| 25 | rac-2-{5-[(3-ethoxypyridin-2-yl)oxy]pyridin-3-yl}-N-[(3R,5S)-5-fluoropiperidin-3-yl]pyrimidine-5-carboxamide, trifluoroacetate salt | $^1$H NMR (400 MHz, DMSO-d$_6$) δ 9.40 (d, J = 1.8 Hz, 1H), 9.27 (s, 2H), 9.15-8.93 (br s, 2H), 8.79 (br d, J = 6.9 Hz, 1H), 8.65 (d, J = 2.7 Hz, 1H), 8.38 (dd, J = 2.7, 1.8 Hz, 1H), 7.68 (dd, J = 4.9, 1.5 Hz, 1H), 7.58 (dd, J = 8.0, 1.5 Hz, 1H), 7.18 (dd, J = 8.0, 4.8 Hz, 1H), 5.01 (br d, J$_{HF}$ = 45.8 Hz, 1H), 4.36-4.25 (m, 1H), 4.18 (q, J = 7.0 Hz, 2H), 3.57-3.45 (m, 1H), 3.39 (br d, J = 12.4 Hz, 1H), 3.31-3.19 (m, 1H), 3.06 (dd, J = 12.4, 8.1 Hz, 1H), 2.43-2.29 (m, 1H), 2.08-1.95 (m, 1H), 1.37 (t, J = 7.0 Hz, 3H); 439.2 |

$^1$Conditions for analytical HPLC. Column: Waters Atlantis dC18, 4.6 × 50 mm, 5 μm; Mobile phase A: 0.05% trifluoroacetic acid in water (v/v); Mobile phase B: 0.05% trifluoroacetic acid in acetonitrile (v/v); Gradient: 5.0% to 95% B, linear over 4.0 minutes; Flow rate: 2 mL/minute.
$^2$Conditions for analytical HPLC. Column: Waters XBridge C18, 2.1 × 50 mm, 5 μm; Mobile phase A: 0.0375% trifluoroacetic acid in water; Mobile phase B: 0.01875% trifluoroacetic acid in acetonitrile; Gradient: 1% to 5% B over 0.6 minutes; 5% to 100% B over 3.4 minutes; Flow rate: 0.8 mL/minute.

Examples D1-D3

Table 3 includes three prophetic examples incorporating a deuterated ethyl group. The preparation of these compounds would employ variations of the methods described above using ordinary skill in the art. Example D1 could be prepared from intermediates P3 and P4, in a manner analogous to that described for Example 4. Examples D2 and D3 could be prepared from a deuterated version of P2 via the methods employed for Examples 2 and 1, respectively.

TABLE 3

Compound name and structure for Examples D1-D3

| Example Number | Compound Name | Structure |
|---|---|---|
| D1 | 2-{5-[((3-Ethoxy-d₅)pyridin-2-yl)oxy]pyridin-3-yl}-N-[(3S,5S)-5-fluoropiperidin-3-yl]pyrimidine-5-carboxamide | 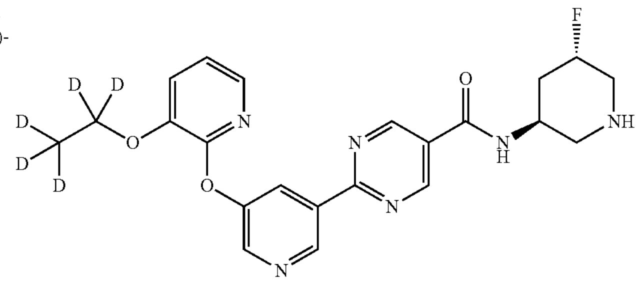 |
| D2 | 2-{5-[((3-Ethoxy-d₅)-5-fluoropyridin-2-yl)oxy]pyridin-3-yl}-N-[(3S,5S)-5-fluoropiperidin-3-yl]pyrimidine-5-carboxamide | 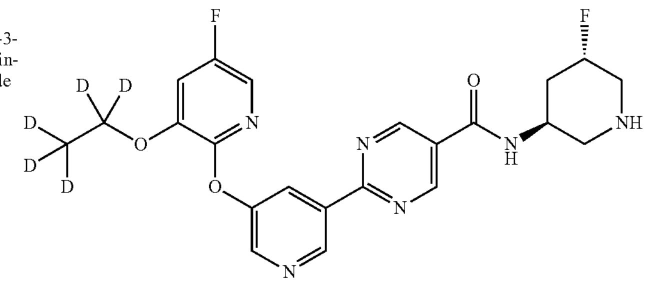 |
| D3 | 2-{5-[((3-Ethoxy-d₅)-5-fluoropyridin-2-yl)oxy]pyridin-3-yl}-N-[(3R,4S)-4-fluoropiperidin-3-yl]pyrimidine-5-carboxamid | 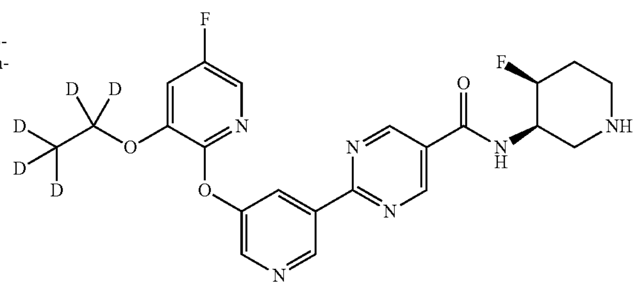 |

Pharmacological Data

The following protocols may of course be varied by those skilled in the art.

Generation of Human DGAT2 (hDGAT2) Construct

A construct for hDGAT2 was generated with an N-terminal FLAG tag (an octapeptide with the amino acid sequence of AspTyrLysAspAspAspAspLys). For the FLAG-tagged hDGAT2 construct, the cDNA for hDGAT2 was custom-synthesized at Genscript and cloned into the pFastBac1 vector (Invitrogen) by using BamHI/XhoI restriction enzymes to generate an N-terminally FLAG-tagged pFast-Bac1-FLAG-hDGAT2 construct (amino acids 1-388). The construct was confirmed by sequencing in both directions.

DGAT2 Expression and Preparation of the DGAT2 Membrane Fraction

Recombinant baculovirus for the FLAG-tagged hDGAT2 was generated in SF9 insect cells using Bac-to-Bac baculovirus expression system (Invitrogen) according to the manufacturer's protocol. For the expression of hDGAT2, SF9 cells (20 L) grown in Sf900II media were infected with hDGAT2 baculovirus at a multiplicity of infection of 1 in a Wave Bioreactor System 20/50P wave bag (GE Healthcare). After 40 hours of infection, the cells were then harvested by centrifugation at 5,000×g. The cell pellets were washed by resuspending in phosphate buffered saline (PBS) and collected by centrifugation at 5,000×g. The cell paste was flash frozen in liquid N2 and stored at −80° C. until needed. All operations below were at 4° C. unless otherwise noted. The cells were resuspended in lysis buffer (50 mM Tris-HCl, pH 8.0, 250 mM sucrose) including 1 mM ethylenediaminetetraacetic acid (EDTA) and the complete protease inhibitor cocktail (Roche Diagnostics) at a ratio of 3 mL buffer per 1 g cell paste. The cells were lysed by dounce homogenizer. The cell debris was removed by centrifugation at 1,000×g for 20 min, and the supernatant was centrifuged at 100,000×g for 1 hour. The resulting pellet was rinsed three times by filling ultracentrifuge tubes to the top with ice cold PBS before decanting. The washed pellet was resuspended with gentle stirring for 1 hour in lysis buffer containing 8 mM 3-[(3-cholamidopropyl)dimethylammonio]-1-propanesulfonate (CHAPS) at a ratio of 1 mL buffer per 1 g of original cell paste and centrifuged again at 100,000×g for 1 hour. The resulting supernatant was aliquotted, flash frozen in liquid N₂, and stored at −80° C. until use.

In Vitro DGAT2 Assay and Determination of $IC_{50}$ Values for DGAT2 Inhibitors

For determination of $IC_{50}$ values, the reactions were carried out in 384-well white polypropylene plates (Nunc) in a total volume of 20 µL. To 1 µL of compounds dissolved in 100% DMSO and spotted at the bottom of each well, 5 µL of 0.04% bovine serum albumin (BSA) (fatty acid free, Sigma Aldrich) was added and the mixture was incubated at room temperature for 15 minutes. hDGAT2 membrane fractions were diluted in 100 mM Hepes-NaOH, pH 7.4, 20 mM $MgCl_2$ containing 200 nM methyl arachidonyl fluorophosphonate (Cayman Chemical; dried from ethyl acetate stock solution under argon gas and dissolved in DMSO as 5 mM stock). 10 µL of this enzyme working solution was added to the plates and incubation continued for 2 hours at room temperature. DGAT2 reactions were initiated by the addition of 4 µL of substrates containing 30 µM [1-$^{14}$C]decanoyl-CoA (custom-synthesized by Perkin Elmer, 50 mCi/mmol) and 125 µM 1,2-didecanoyl-sn-glycerol (Avanti Polar Lipids) dissolved in 12.5% acetone. The reaction mixtures were incubated at room temperature for 40 min and the reactions were stopped by addition of 5 µL of 1% $H_3PO_4$. After the addition of 45 µL MicroScint-E (Perkin-Elmer), plates were sealed with Top Seal-A covers (Perkin-Elmer) and phase partitioning of substrates and products was achieved using a HT-91100 microplate orbital shaker (Big Bear Automation, Santa Clara, Calif.). Plates were centrifuged at 2,000×g for 1 minute in an Allegra 6R Centrifuge (Beckman Coulter) and then were sealed again with fresh covers before reading in a 1450 Microbeta Wallac Trilux Scintillation Counter (Perkin Elmer). DGAT2 activity was measured by quantifying the generated product [$^{14}$C]tridecanoylglycerol in the upper organic phase.

Background activity obtained using 50 µM of ((R)-1-(2-((S)-1-(4-chloro-1H-pyrazol-1-yl)ethyl)-3H-imidazo[4,5-b]pyridin-5-yl)piperidin-3-yl)(pyrrolidin-1-yl)methanone (WO 2013150416, Example 196-A) for complete inhibition of DGAT2 was subtracted from all reactions. Inhibitors were tested at eleven different concentrations to generate $IC_{50}$ values for each compound. The eleven inhibitor concentrations employed typically included 50, 15.8, 5, 1.58, 0.50, 0.16, 0.05, 0.016, 0.005, 0.0016, and 0.0005 µM. The data were plotted as percentage of inhibition versus inhibitor concentration and fit to the equation, $y=100/[1+(x/IC_{50})^z]$, where $IC_{50}$ is the inhibitor concentration at 50% inhibition and z is the Hill slope (the slope of the curve at its inflection point).

Table 4 below provides the $IC_{50}$ values of the Examples for inhibition of DGAT2 in accordance with the above-described assay. Results are reported as geometric mean $IC_{50}$ values, with the number of replicates (n) shown.

TABLE 4

$IC_{50}$ values of Examples for inhibition of DGAT2

| Example | DGAT2 $IC_{50}$ [nM] | n | Example | DGAT2 $IC_{50}$ [nM] | n |
|---|---|---|---|---|---|
| 1 | 5.8 | 8 | 2 | 8.6 | 13 |
| 3 | 40 | 15 | 4 | 10 | 22 |
| 5 | 110 | 11 | 6 | 80 | 7 |
| 7 | 42 | 5 | 8 | 650 | 3 |
| 9 | 19 | 6 | 10 | 39 | 3 |
| 11 | 4.4 | 3 | 12 | 590 | 9 |
| 13 | 57 | 3 | 14 | 3100 | 3 |
| 15 | 3300 | 3 | 16 | 480 | 3 |
| 17 | 230 | 3 | 18 | 140 | 3 |
| 19 | 240 | 3 | 20 | 2100 | 3 |
| 21 | 5000 | 3 | 22 | 21000 | 1 |
| 23 | 14000 | 1 | 24 | 16000 | 1 |
| 25 | 200 | 5 | WO2018033832 Ex. 1 | 17 | 6 |
| WO2018033832 Ex. 2 | 200 | 3 | WO2018033832 Ex. 3.1 | 13 | 4 |
| WO2018033832 Ex. 3.3 | 200 | 3 | WO2018033832 Ex. 6a | 25 | 9 |
| WO2018033832 Ex. 6b | 29 | 9 | WO2018033832 Ex. 8 | 3.3 | 8 |

Wherein the Examples of WO2018033832 referenced herein are shown in Table 4A below:

TABLE 4A

Chemical Structures for Examples from WO2018033832 (note: stereochemistry configurations depicted below as shown/described in WO2018033832)

| Example Number | Chemical Structure |
|---|---|
| 1 | 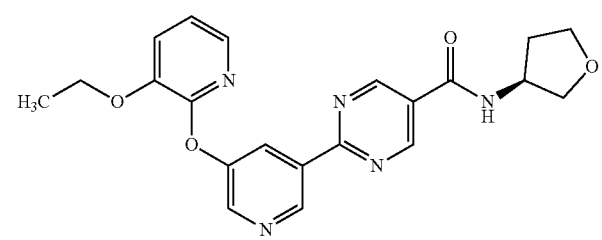 [SMILES: CCOc1cccnc1Oc1cncc(-c2ncc(C(=O)N[C@H]3CCOC3)cn2)c1] |

TABLE 4A-continued

Chemical Structures for Examples from WO2018033832 (note: stereochemistry configurations depicted below as shown/described in WO2018033832)

| Example Number | Chemical Structure |
|---|---|
| 2 | 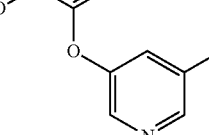 |
| 3.1 | 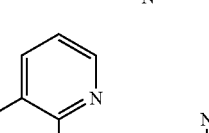 |
| 3.3 | 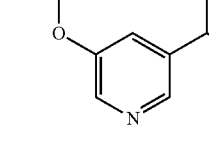 |
| 6a and 6b | 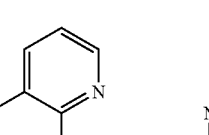 |
| 8 | 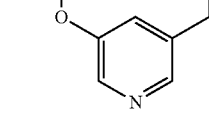 |

Determination of $IC_{50}$ Values for DGAT2 Inhibitors in Human Hepatocytes

For evaluation of the effects of DGAT2 inhibitors in a cell-based setting, cryopreserved human hepatocytes (Lot DOO, Celsis, Baltimore, Md.) were thawed and plated onto type I collagen-coated plates according to the manufacturer's instructions. After 18 hours overnight recovery period, the cells were overlayed with media containing 250 µg/mL Geltrex Basement Membrane Matrix (Thermo Fisher). The following day, media was aspirated and replaced with serum-free Williams Media E (Thermo Fisher) containing 400 µM sodium dodecanoate (Sigma-Aldrich, St. Louis, Mo.) and 2 mM GlutaMAX (Thermo Fisher). Forty-five minutes later, a selective DGAT1 inhibitor (Example 2, WO2009016462, prepared as a 100× stock in 25% DMSO, 75% PBS) was added to all wells at a final concentration (3 µM) that completely suppressed endogenous DGAT1 activity. DGAT2 inhibitors were then added to the desired final concentration. After a 15 minute preincubation, 0.2 µCi [$^{14}$C(U)]-glycerol (Perkin Elmer) was added to each well followed by a 3 hour incubation. At this point the media was removed, and the cells lysed via orbital shaking in isopropyl alcohol: tetrahydrofuran (9:1) for 15 minutes prior to centrifugation at 3000 rpm for 10 minutes. Radiolabeled lipids were resolved using a solvent system by thin layer chromatography with the solvent consisting of hexanes:diethyl ether:glacial acetic acid (75:23:2, v/v/v). After separation, radiolabeled lipids were visualized using the Typhoon 9500 phosphorimaging system (GE). The half maximal inhibitory concentrations ($IC_{50}$ values) were determined by nonlinear regression analysis of the % inhibition dose response curve using GraphPad Prism (GraphPad Software, Inc., La Jolla, Calif.).

Table 5 below provides the $IC_{50}$ values of selected Examples for inhibition of DGAT2 in human hepatocytes in accordance with the above-described assay. Results are reported as geometric mean $IC_{50}$ values, with the number of replicates (n) shown.

TABLE 5

$IC_{50}$ values of Examples for inhibition of DGAT2 in human hepatocytes

| Example | DGAT2 $IC_{50}$ [nM] | n | Example | DGAT2 $IC_{50}$[nM] | n |
|---|---|---|---|---|---|
| 2 | 4.1 | 4 | 3 | 23 | 3 |
| 4 | 11 | 13 | 5 | 26 | 6 |
| 6 | 2.4 | 2 | 7 | 100 | 3 |
| 13 | 3.8 | 2 | 18 | 20 | 2 |
| 25 | >130 | 3 | WO2018033832 Ex. 1 | 2.8 | 10 |

In Vivo Effects of DGAT2 Inhibitors on Plasma and Hepatic Triglyceride Levels

The rat western diet model was utilized to assess the effects of DGAT2 inhibitor treatment on plasma triglyceride production and hepatic triglyceride content in vivo. Male Sprague-Dawley rats were housed under standard laboratory conditions on a 12-hour light, 12-hour dark cycle (lights on at 06:00). Two weeks prior to study start animals were placed on a high-fat, high sucrose, high-cholesterol diet (D12079b, provided by Research Diets, New Brunswick, N.J.). This diet provides ~43% of kilocalories from carbohydrate and ~41% of kilocalories from fat. Example 4 was administered orally as a solution (10 mL/kg dosing volume) in 0.5% methylcellulose in deionized water, pH 7.0-7.5 (methylcellulose was obtained from Sigma-Aldrich, St. Louis, Mo.). Vehicle-treated animals received an aqueous solution of 0.5% methylcellulose in deionized water alone, pH 7.0-7.5. Each treatment was administered orally twice daily for 7 days at 08:00 and 16:00 at 3, 10, 30 and 100 mg/kg, for a total daily dose of 6, 20, 60 and 200 mg/kg/day. On day 8, animals were dosed with vehicle or Example 4 at 10:00 and sacrificed 2 hours post-dose. Rats were sacrificed by carbon dioxide asphyxiation and blood collected via lateral tail vein. Plasma TG levels were determined using a Roche Hitachi Chemistry analyzer according to the manufacturer's instructions (Roche Diagnostics Corporation, Indianapolis, Ind.) and data was analyzed using GraphPad Prism (GraphPad Software, Inc., La Jolla, Calif.). The liver was collected at sacrifice for determination of hepatic triglyceride and the tissue was immediately frozen in liquid nitrogen, and held at −80° C. until analysis. For assessment of hepatic triglyceride levels, a section of liver wrapped in aluminum foil was pulverized with a hammer, on an aluminum heat block in a liquid nitrogen bath. Pulverization of the liver tissue produced a homogeneous powder. Homogenization buffer, Tris pH 7.4, 98.9 milliliters 0.9% NaCl and 100 microliters of Triton X 100, was mixed on a stir plate for 10 minutes prior to using. Sample weights of approximately one-hundred milligrams of homogenous liver tissue were weighed and placed in Lysing Matrix D tube (MP Biomedicals, Cat #6913-100) with 1 mL of homogenization buffer. All samples were then placed in the FastPrep FP120 (MP Biomedicals, Cat #6001-120) for 2 minutes or until tissue was homogenized. All samples were then spun for 30 seconds at 10,000 g, to clear foam from homogenization. 50 Microliters of sample was transferred to a sterile mixing plate with 450 microliters of Dulbecco's phosphate-buffered saline (DPBS) to create a 1:10 dilution. Upon re-suspension of the new sample, all samples were transferred to sampling tubes for the Siemens Advia XPT Clinical Analyzer. The triglyceride assay was performed through absorbance and reported as milligrams per deciliter. Triglycerides were then normalized per gram of tissue in Microsoft excel. As summarized in FIGS. 4 and 5, there was a dose dependent reduction in plasma (up to ~70%) and liver (up to 48%) triglycerides in rats administered Example 4. In the instance of the circulating triglyceride response, the resulting levels observed with Example 4 approached those of the chow-fed vehicle animals.

Figure 4:
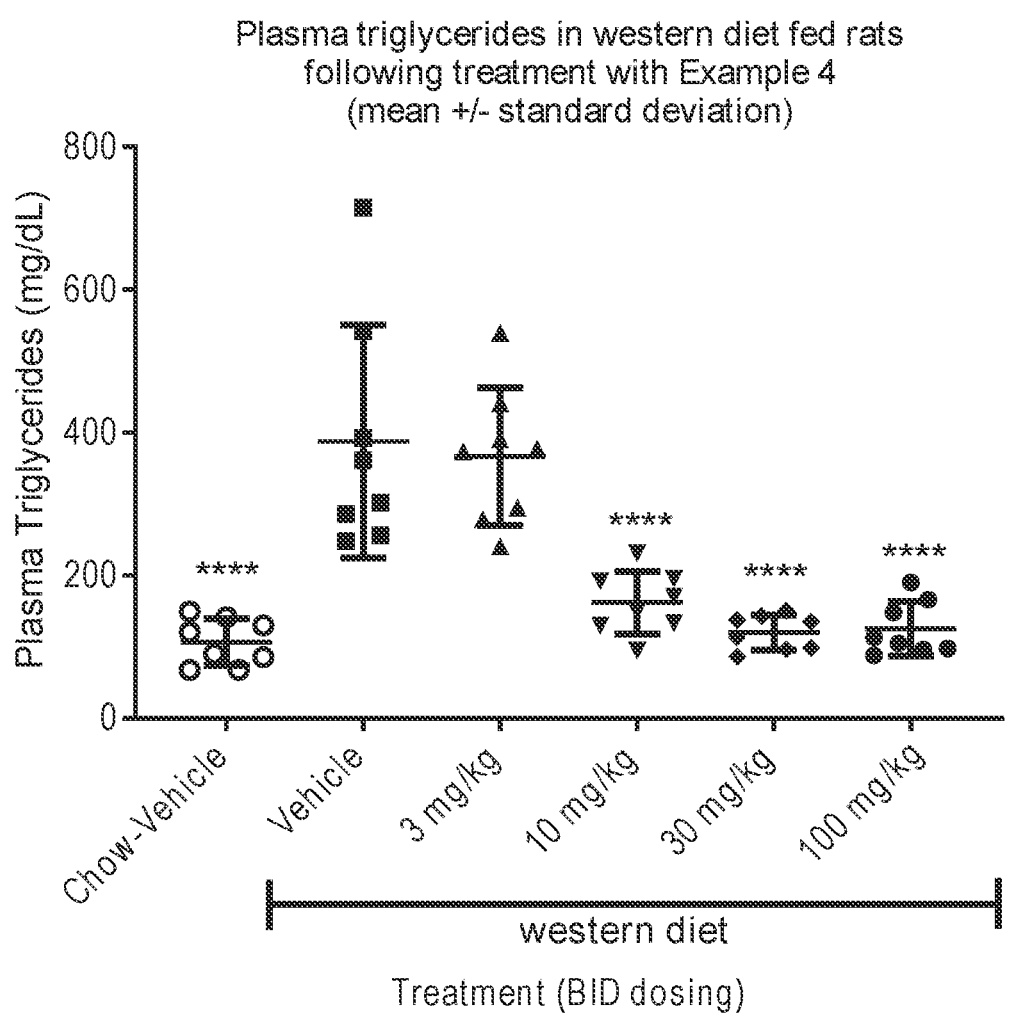
FIG. 4 plots the multiple dose effects of Example 4 on plasma triglyceride in Western diet fed Sprague-Dawley rats (Vertical Axis: plasma triglyceride (mg/dL), Horizontal Axis: Western Diet BID dosing (mg/kg)).

FIG. 4 plots the multiple dose effects of Example 4 on Plasma Triglyceride in Western Diet Fed Sprague-Dawley Rats where plasma triglyceride levels were determined from blood drawn from the lateral tail vein 2-hours following the final dose of Example 4. Data are mean±standard deviation from 8 animals. Difference between group means relative to vehicle was performed by a 1-way ANOVA followed by a Dunnett's multiple comparisons test. ****=p<0.0001 relative to western diet vehicle animals.

Figure 5:
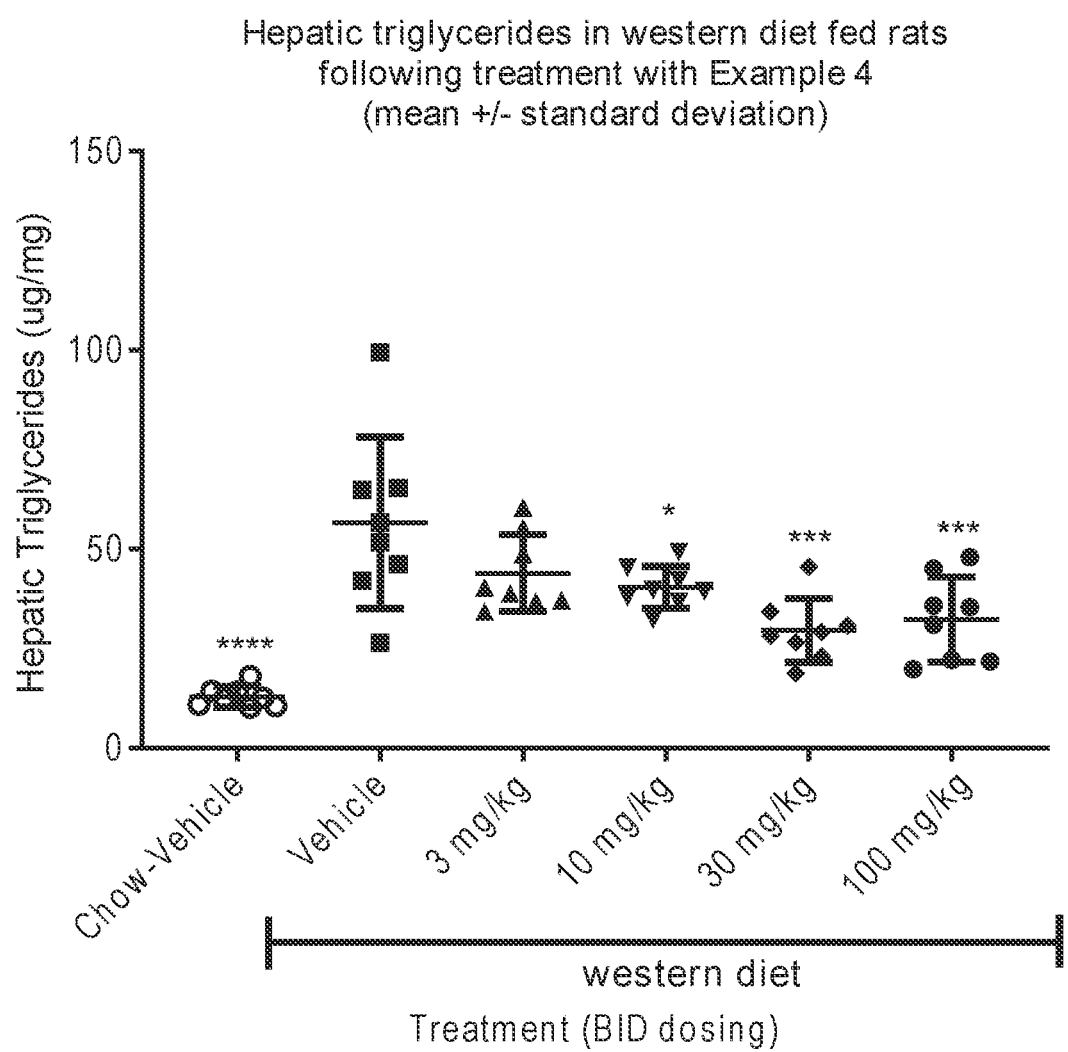
FIG. 5 plots the multiple dose effects of Example 4 on hepatic triglyceride in Western diet fed Sprague-Dawley rats (Vertical Axis: hepatic triglyceride (µg/mg), Horizontal Axis: Western Diet BID dosing (mg/kg)).

FIG. 5 plots the multiple dose effects of Example 4 on Hepatic Triglyceride in Western Diet Fed Sprague-Dawley Rats where hepatic triglyceride levels were determined from blood drawn from the lateral tail vein 2-hours following the final dose of Example 4. Data are mean±standard deviation from 8 animals. Difference between group means relative to western diet vehicle was performed by a 1-way ANOVA followed by a Dunnett's multiple comparisons test. *=p<0.05, *=p<0.001, **=p<0.0001 relative to western diet vehicle animals.

Determination of pKa

The exemplified compounds were designed to be basic inhibitors of DGAT2. The pKa of selected examples was determined by Analiza, Inc. (Cleveland, Ohio), according to the capilliary electrophoresis method described in Shalaeva, M., et al. 2008, *J. Pharm. Sci.*, 97, 2581-2606. Table 6 below shows the most basic pKa determined for the examples and are presented as the mean along with the number of replicates (n). Basic compounds are associated with higher volume of distribution in vivo (Obach, R. S., et al. 2009, *Drug Metab. Dispos.*, 36, 1385-1405; Smith, D. A., et al. 2015, *J. Med. Chem.*, 58. 5691-5698).

TABLE 6

Most basic pKa for selected Examples

| Example | Basic pKa | n | Example | Basic pKa | n |
|---|---|---|---|---|---|
| 1 | 7.7 | 1 | 2 | 7.3 | 3 |
| 3 | 8.1 | 3 | 4 | 7.5 | 3 |
| 5 | 7.3 | 2 | 6 | 7.4 | 2 |
| 7 | 7.5 | 1 | 8 | 5.3 | 1 |
| 9 | 4.0 | 1 | 10 | 4.7 | 1 |
| 11 | 4.5 | 1 | 12 | 7.5 | 1 |
| 13 | 6.7 | 2 | 14 | 9.5 | 1 |
| 16 | 6.4 | 1 | 17 | 5.4 | 2 |
| 18 | 5.2 | 1 | 19 | 5.2 | 1 |
| 21 | 9.1 | 1 | 25 | 6.8 | 1 |
| WO2018033832 Ex. 1 | 2.4 | 1 | WO2018033832 Ex. 2 | 2.5 | 1 |
| WO2018033832 Ex. 6a | 2.3 | 1 | WO2018033832 Ex. 6b | 2.4 | 1 |

Determination of Intrinsic Clearance in Human Hepatocytes (Relay Method)

For intrinsic clearance ($CL_{int}$) measurement, hepatocyte relay method was used (Di, L., et al. 2012, *Drug Metab. Dispos.*, 40, 1860-1865 and Di, L., et al. 2013, *Drug Metab. Dispos.*, 41, 2018-2023). Cryopreserved human hepatocytes (Lot DCM from BioreclamationIVT) were used. Upon thawing, the hepatocytes were resuspended in Williams' medium E (custom formula number 91-5233EA; Gibco, Grand Island, N.Y.) supplemented with Hepes and $Na_2CO_3$. The cells were counted using the trypan blue exclusion method, and the 24-well hepatocyte plates containing 0.5 million cells/mL were spiked with the test compound at a final concentration of 1 µM (dimethyl sulfoxide, final concentration 0.025%; methanol, final concentration 0.1125%), in a final incubation volume of 0.50 mL. The plates were incubated at 37° C. with 95% air/5% $CO_2$, 75% relative humidity for 4 h at 150 rpm in a humidified incubator. At time 0 and 4 h, 25 µL of hepatocyte suspension was removed from the incubation and added to 50 µL of ice-cold acetonitrile (containing metoprolol, indomethacin, and terfenadine as internal standards) to quench the reaction. The samples were centrifuged (Eppendorf, Hauppauge, N.Y.) at 3000 rpm (1439×g) for 10 min at room temperature, and 50 µL of supernatant was transferred to a clean plate, dried completely, and reconstituted before liquid chromatography/tandem mass spectrometry (LC-MS/MS) analysis. The remaining hepatocyte suspensions in the incubation plate were centrifuged (3000 rpm, 1439×g, 10 min, room temperature). The supernatant of 300 µL was transferred to a clean 24-well plate and stored at −80° C. until the next relay experiment. For the second relay experiment, the supernatant plates were warmed first to room temperature for 30 minutes, then to 37° C. for 30 min, and hepatocytes were added to the samples to give a final cell density of 0.5 million cells/mL. The plates were incubated at 37° C. for 4 h, sampled, and processed as described above. Five relays were performed to give a total incubation time of 20 h, with sampling points at (0, 4, 8, 12, 16 and 20 h). The concentrations of test compound determined at each time point by the LC-MS/MS analysis were used to calculate the intrinsic clearance.

Table 7 below shows the intrinsic clearance for selected Examples as determined by the method described above. The data are presented as the mean+/− standard deviation, with the number of replicates (n) shown.

TABLE 7

$CL_{int, u}$ in the relay hepatocyte assay

| Example number | $CL_{int}$ (µL/min/million cells) (+/− Std Dev) | n |
|---|---|---|
| 4 | 0.98 +/− 0.22 | 2 |
| 5 | 1.9 +/− 0.47 | 2 |
| WO2018033832 Ex. 1 | 3.9 +/− 0.52 | 6 |
| WO2018033832 Ex. 2 | 4.9 +/− 0.17 | 2 |
| WO2018033832 Ex. 6a | 3.2 +/− 0.21 | 2 |
| WO2018033832 Ex. 6b | 2.9 +/− 0.057 | 2 |

High Throughput Determination of Intrinsic Clearance in Human Hepatocytes

The high throughput human hepatocyte stability assay was performed in a 384-well format (Di, L., et al. 2012, *Eur. J. Med. Chem.*, 57, 441-448). Pooled cryopreserved human hepatocytes of 10 donors were purchased from BioreclamationIVT (Baltimore, Md., Lot DCM). The cryopreserved human hepatocytes were thawed, and re-suspended in Williams E medium (WEM GIBCO, custom formula #A28859EA) supplemented with HEPES and $Na_2CO_3$. The cells were counted using the Trypan Blue exclusion method. The Multidrop® liquid dispenser (Multidrop DW, Thermo Scientific, Waltham, Mass.) was used to add the hepatocyte suspensions to the 384-well plates. The cell plates were covered and transferred to a Sciclone® ALH 3000 workstation (Caliper Life Sciences, Hopkinton, Mass.), equipped with two 6-position Mecour heat exchangers. Test compounds were diluted on the Sciclone® with buffer and added to the hepatocytes. The final incubation contained 0.5 million cells/mL and 1 µM test compound in 15 µL total volume with 0.01% DMSO. The incubation was carried out at 37° C. At various time points (0, 3, 10, 30, 60, 120, 240 min), the reactions were quenched with cold acetonitrile containing internal standard (Example 39A, WO1999/57125). The samples were centrifuged (Eppendorf, Hauppauge, N.Y.) at 3000 rpm for 5 min at 4° C. The supernatants were transferred using the BioMek® FX liquid handler (Beckman Coulter, Inc. Danvers Mass.) to new plates with water addition, which were sealed prior to LC-MS/MS analysis. Table 8 below shows the intrinsic clearance for selected examples as determined in the high throughput human hepatocyte assay described above. The data are presented as the mean+/− standard deviation, with the number of replicates (n) shown.

TABLE 8

CL$_{int}$ in the high throughput human hepatocyte assay

| Example | CL$_{int}$ (µL/min/10$^6$ cells) (+/− Std Dev) | n | Example | CL$_{int}$ (µL/min/10$^6$ cells) (+/− Std Dev) | n |
|---|---|---|---|---|---|
| 1 | <2.7 +/− 0.72 | 10 | 2 | 3.6 +/− 1.2 | 22 |
| 3 | <1.9 +/− 0.35 | 20 | 4 | <1.8 +/− 0.041 | 14 |
| 5 | <1.9 +/− 0.39 | 10 | 6 | 4.7 +/− 1.0 | 12 |
| 7 | <1.8 +/− 0.30 | 10 | 8 | 12 +/− 1.6 | 2 |
| 9 | 54 +/− 8.4 | 2 | 10 | 27 +/− 3.6 | 2 |
| 11 | 38 +/− 2.0 | 2 | 12 | <2.6 +/− 0.56 | 10 |
| 13 | 12 +/− 0.23 | 2 | 14 | <1.8 +/− 0.11 | 10 |
| 15 | 5.3 +/− 0.68 | 2 | 16 | 4.7 +/− 1.4 | 10 |
| 17 | 8.3 +/− 0.71 | 2 | 18 | 9.3 +/− 1.2 | 2 |
| 19 | 14 +/− 1.4 | 2 | 25 | 6.5 +/− 2.1 | 10 |
| WO2018033832 Ex. 1 | <3.8 +/− 1.1 | 15 | WO2018033832 Ex. 2 | 4.7 +/− 0.55 | 4 |
| WO2018033832 Ex. 3.1 | 9.3 +/− 1.1 | 2 | WO2018033832 Ex. 3.3 | 5.1 +/− 0.69 | 2 |
| WO2018033832 Ex. 6a | <3.8 +/− 1.1 | 4 | WO2018033832 Ex. 6b | <3.3 +/− 0.49 | 4 |
| WO2018033832 Ex. 8 | 9.3 +/− 0.52 | 2 | | | |

Determination of Intrinsic Clearance in Human Liver Microsomes

The high throughput human microsomal stability assay was performed in a 384-well format (Di, L., et al. 2012, Eur. J. Med. Chem., 57, 441-448). All liquid handling and incubation were conducted with a Biomek FX (Beckman Coulter, Inc., Indianapolis, Ind.), equipped with one 3-position Mecour heated deck positions. Pooled human liver microsomes of 50 donors (Lot: HLM-103) were purchased from BD Biosciences (Bedford, Mass.). Each incubation contained test compound (1 µM), human liver microsomes (0.25 µM CYP protein equivalent to 0.806 mg/mL protein concentration), NADPH 20.9 mM, MgCl$_2$ (3.3 mM) and potassium phosphate buffer (100 mM at pH 7.4). The final reaction volume was 45 µL containing 0.1% DMSO. The incubations were conducted at 37° C. At various time points (e.g. 1, 4, 7, 12, 20, 25, 45 and 60 min), cold acetonitrile with mass spectrometry (MS) internal standard (Example 39A, WO1999/57125) was added to quench the reaction. The plates were centrifuged at 3000 rpm for 1 min at 4° C. (Sorvall RC 3C Plus, Thermo Scientific, Waltham, Mass.). The plates were sealed and subsequently analyzed using LC-MS/MS. Control plates were prepared in the same manner without adding the NADPH cofactor to monitor any non-CYP/FMO catalyzed decline. Table 9 below shows the intrinsic clearance for selected examples as determined in the human liver microsome assay described above. The data are presented as the mean+/− standard deviation, with the number of replicates (n) shown.

TABLE 9

CL$_{int}$ in the human liver microsome assay

| Example | CL$_{int}$ (µL/min/mg) (+/− STD Dev) | n | Example | CL$_{int}$ (µL/min/mg) (+/− STD Dev) | n |
|---|---|---|---|---|---|
| 1 | <7 | 1 | 2 | <7 | 3 |
| 3 | <7 | 3 | 4 | <7 | 6 |
| 5 | <7 | 3 | 6 | <7.8 +/− 1.5 | 3 |
| 7 | <7 | 1 | 8 | <14 +/− 10 | 2 |
| 9 | >290 | 2 | 10 | 270 +/− 12 | 2 |
| 11 | >290 | 2 | 12 | <7 | 1 |
| 13 | 35 +/− 3.4 | 3 | 14 | <8 | 1 |
| 15 | 21 | 1 | 16 | 17 | 1 |
| 17 | 23 | 1 | 18 | 19 +/− 1.5 | 2 |
| 19 | 34 +/− 1.9 | 2 | 20 | 8.9 | 1 |
| 21 | <8 | 1 | 22 | <8 | 1 |
| 23 | <8 | 1 | 24 | <8 | 1 |
| 25 | 11 +/− 2.3 | 3 | WO2018033832 Ex. 1 | 11 +/− 2.9 | 2 |
| WO2018033832 Ex. 2 | 17 +/− 1.3 | 2 | WO2018033832 Ex. 3.1 | 30 | 1 |
| WO2018033832 Ex. 3.3 | <8 | 1 | WO2018033832 Ex. 6a | 13 +/− 2.0 | 2 |
| WO2018033832 Ex. 6b | <11 +/− 3.5 | 3 | WO2018033832 Ex. 8 | <9.6 | 3 |

Determination of Thermodynamic Solubility in Various Media

The solubility of active pharmaceutical ingredients is an important characteristic in determining biological performance and ease of formulation during drug development, with high solubility being preferred (Klein, S. 2010, The AAPS Journal, 12, 397-406; Di, L., et al 2012, Drug Disc.

Today, 17. 486-495). Thermodynamic solubility was measured in various biorelevant media, as shown in Table 10. A test sample of crystalline solid (~7 mg) was combined in a vial with 1 mL of the relevant buffer solution and the mixture vortexed to combine. If the solid dissolved completely, additional solid was added with vortexing until a saturated solution was obtained. The saturated solution/solid mixture was capped and subjected to temperature cycling as follows: 1 min at 25° C., 8 h at 40° C., 5 h at 15° C. and 12 h at 25° C. The mixture was filtered in a centrifugal filtration device (0.22 μm PVDF filter, MilliporeSigma, Milwaukee, Wis.) at 13,000 rpm and the concentration of the test compound in the filtrate was determined by HPLC/UPLC with reference to a three point standard curve. Phosphate buffered saline (PBS, pH 6.8, 50 mM phosphate buffer, 250 mM NaCl). Simulated gastric fluid (SGN pH 1.2, USP recipe). Fasted state simulated intestinal fluid (FaSSIF, 3 mM sodium taurocholate, 0.75 mM phospholipid from soybean lecithin, 50 mM phosphate buffer, ionic strength adjusted to 250 mM with NaCl, pH 6.8) and fed state simulated intestinal fluid (FeSSIF, 15 mM sodium taurocholate, 3.75 mM phospholipid from soybean lecithin, 144 mM acetic acid, 50 mM phosphate buffer, ionic strength adjusted to 250 mM with NaCl, pH 6.8).

TABLE 10

Thermodynamic Solubility in Biorelevant Media

| Example number | Buffer | Solubility (mg/mL) |
| --- | --- | --- |
| 4 | PBS, pH 6.8 | 0.58 |
| WO2018033832 Ex. 1, Form 1 | PBS, pH 6.8 | 0.043 |
| WO2018033832 Ex. 1, Form 2 | PBS, pH 6.8 | 0.060 |
| 4 | SGN pH 1.2 | >27 |
| WO2018033832 Ex. 1, Form 1 | SGN pH 1.2 | 0.078 |
| WO2018033832 Ex. 1, Form 2 | SGN pH 1.2 | 1.082 |
| 4 | FaSSIF pH 6.8 | 0.955 (n = 2) |
| WO2018033832 Ex. 1, Form 1 | FaSSIF pH 6.8 | 0.069 |
| WO2018033832 Ex. 1, Form 2 | FaSSIF pH 6.8 | 0.093 |

Throughout this application, various publications are referenced. The disclosures of these publications in their entireties are hereby incorporated by reference into this application for all purposes.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of treating fatty liver, nonalcoholic fatty liver disease, nonalcoholic steatohepatitis, nonalcoholic steatohepatitis with liver fibrosis, nonalcoholic steatohepatitis with cirrhosis or nonalcoholic steatohepatitis with cirrhosis and hepatocellular carcinoma comprising administering to a human in need of such treatment a therapeutically effective amount of a compound selected from the croup consisting of:

2-(5-((3-ethoxy-5-fluoropyridin-2-yl)oxy)pyridin-3-yl)-N-((3R,4S)-4-fluoropiperidin-3-yl)pyrimidine-5-carboxamide;

2-(5-((3-ethoxy-5-fluoropyridin-2-yl)oxy)pyridin-3-yl)-N-((3S,5S)-5-fluoropiperidin-3-yl)pyrimidine-5-carboxamide;

2-(5-((3-ethoxypyridin-2-yl)oxy)pyridin-3-yl)-N-((3R,4S)-4-fluoropiperidin-3-yl)pyrimidine-5-carboxamide;

2-(5-((3-ethoxypyridin-2-yl)oxy)pyridin-3-yl)-N-((3R,4R)-4-fluoropiperidin-3-yl)pyrimidine-5-carboxamide;

2-(5-((3-ethoxy-5-fluoropyridin-2-yl)oxy)pyridin-3-yl)-N-((3R,4R)-4-fluoropiperidin-3-yl)pyrimidine-5-carboxamide; and 2-(5-((3-ethoxypyridin-2-yl)oxy)pyridin-3-yl)-N-((3S,5S)-5-fluoropiperidin-3-yl)pyrimidine-5-carboxamide, or a pharmaceutically acceptable salt of said compound.

2. The method as recited in claim 1 wherein nonalcoholic steatohepatitis is treated.

3. The method as recited in claim 1 wherein nonalcoholic fatty liver disease is treated.

4. The method as recited in claim 1 wherein nonalcoholic steatohepatitis with liver fibrosis is treated.

5. A method for the reduction of at least one point in severity of nonalcoholic fatty liver disease (NAFLD) Activity Score (NAS) from baseline comprising the step of measuring the baseline NAS in a human, administering to said human an effective amount of a compound selected from the croup consisting of:

2-(5-((3-ethoxy-5-fluoropyridin-2-yl)oxy)pyridin-3-yl)-N-((3R,4S)-4-fluoropiperidin-3-yl)pyrimidine-5-carboxamide;

2-(5-((3-ethoxy-5-fluoropyridin-2-yl)oxy)pyridin-3-yl)-N-((3S,5S)-5-fluoropiperidin-3-yl)pyrimidine-5-carboxamide;

2-(5-((3-ethoxypyridin-2-yl)oxy)pyridin-3-yl)-N-((3R,4S)-4-fluoropiperidin-3-yl)pyrimidine-5-carboxamide;

2-(5-((3-ethoxypyridin-2-yl)oxy)pyridin-3-yl)-N-((3R,4R)-4-fluoropiperidin-3-yl)pyrimidine-5-carboxamide;

2-(5-((3-ethoxy-5-fluoropyridin-2-yl)oxy)pyridin-3-yl)-N-((3R,4R)-4-fluoropiperidin-3-yl)pyrimidine-5-carboxamide; and 2-(5-((3-ethoxypyridin-2-yl)oxy)pyridin-3-yl)-N-((3S,5S)-5-fluoropiperidin-3-yl)pyrimidine-5-carboxamide, or a pharmaceutically acceptable salt of said compound, and measuring the NAS of said human.

6. A method for the reduction of at least two points in severity of nonalcoholic fatty liver disease (NAFLD) Activity Score (NAS) from baseline comprising the step of measuring the baseline NAS in a human, administering to said human an effective amount of a compound selected from the group consisting of:

2-(5-((3-ethoxy-5-fluoropyridin-2-yl)oxy)pyridin-3-yl)-N-((3R,4S)-4-fluoropiperidin-3-yl)pyrimidine-5-carboxamide;

2-(5-((3-ethoxy-5-fluoropyridin-2-yl)oxy)pyridin-3-yl)-N-((3S,5S)-5-fluoropiperidin-3-yl)pyrimidine-5-carboxamide;

2-(5-((3-ethoxypyridin-2-yl)oxy)pyridin-3-yl)-N-((3R,4S)-4-fluoropiperidin-3-yl)pyrimidine-5-carboxamide;

2-(5-((3-ethoxypyridin-2-yl)oxy)pyridin-3-yl)-N-((3R,4R)-4-fluoropiperidin-3-yl)pyrimidine-5-carboxamide;

2-(5-((3-ethoxy-5-fluoropyridin-2-yl)oxy)pyridin-3-yl)-N-((3R,4R)-4-fluoropiperidin-3-yl)pyrimidine-5-carboxamide; and 2-(5-((3-ethoxypyridin-2-yl)oxy)pyridin-3-yl)-N-((3S,5S)-5-fluoropiperidin-3-yl)pyrimidine-5-carboxamide, or a pharmaceutically acceptable salt of said compound, and measuring the NAS of said human.

7. A method of treating hypertriglyceridemia, atherosclerosis, myocardial infarction, dyslipidemia, coronary heart disease, hyper apo B lipoproteinemia, ischemic stroke, type 2 diabetes mellitus, glycemic control in patients with type 2 diabetes mellitus, conditions of impaired glucose tolerance (IGT), conditions of impaired fasting plasma glucose, metabolic syndrome, syndrome X, hyperglycemia, hyperinsulinemia, insulin resistance, impaired glucose metabolism, comprising administering to a human in need of such treatment a therapeutically effective amount of a compound selected from the group consisting of:

2-(5-((3-ethoxy-5-fluoropyridin-2-yl)oxy)pyridin-3-yl)-N-((3R,4S)-4-fluoropiperidin-3-yl)pyrimidine-5-carboxamide;

2-(5-((3-ethoxy-5-fluoropyridin-2-yl)oxy)pyridin-3-yl)-N-((3S,5S)-5-fluoropiperidin-3-yl)pyrimidine-5-carboxamide;

2-(5-((3-ethoxypyridin-2-yl)oxy)pyridin-3-yl)-N-((3R,4S)-4-fluoropiperidin-3-yl)pyrimidine-5-carboxamide;

2-(5-((3-ethoxypyridin-2-yl)oxy)pyridin-3-yl)-N-((3R,4R)-4-fluoropiperidin-3-yl)pyrimidine-5-carboxamide;

2-(5-((3-ethoxy-5-fluoropyridin-2-yl)oxy)pyridin-3-yl)-N-((3R,4R)-4-fluoropiperidin-3-yl)pyrimidine-5-carboxamide; and 2-(5-((3-ethoxypyridin-2-yl)oxy)pyridin-3-yl)-N-((3S,5S)-5-fluoropiperidin-3-yl)pyrimidine-5-carboxamide, or a pharmaceutically acceptable salt thereof.

8. The method as recited in claim 7 wherein hypertriglyceridemia is treated.

9. A pharmaceutical composition which comprises a therapeutically effective amount of a compound selected from the group consisting of:

2-(5-((3-ethoxy-5-fluoropyridin-2-yl)oxy)pyridin-3-yl)-N-((3R,4S)-4-fluoropiperidin-3-yl)pyrimidine-5-carboxamide;

2-(5-((3-ethoxy-5-fluoropyridin-2-yl)oxy)pyridin-3-yl)-N-((3S,5S)-5-fluoropiperidin-3-yl)pyrimidine-5-carboxamide;

2-(5-((3-ethoxypyridin-2-yl)oxy)pyridin-3-yl)-N-((3R,4S)-4-fluoropiperidin-3-yl)pyrimidine-5-carboxamide;

2-(5-((3-ethoxypyridin-2-yl)oxy)pyridin-3-yl)-N-((3R,4R)-4-fluoropiperidin-3-yl)pyrimidine-5-carboxamide;

2-(5-((3-ethoxy-5-fluoropyridin-2-yl)oxy)pyridin-3-yl)-N-((3R,4R)-4-fluoropiperidin-3-yl)pyrimidine-5-carboxamide; and 2-(5-((3-ethoxypyridin-2-yl)oxy)pyridin-3-yl)-N-((3S,5S)-5-fluoropiperidin-3-yl)pyrimidine-5-carboxamide, or a pharmaceutically acceptable salt of said compound and a pharmaceutical acceptable carrier, vehicle or diluent.

10. A pharmaceutical combination composition comprising: a therapeutically effective amount of a composition comprising:

a first compound, said first compound being a compound selected from the group consisting of:

2-(5-((3-ethoxy-5-fluoropyridin-2-yl)oxy)pyridin-3-yl)-N-((3R,4S)-4-fluoropiperidin-3-yl)pyrimidine-5-carboxamide;

2-(5-((3-ethoxy-5-fluoropyridin-2-yl)oxy)pyridin-3-yl)-N-((3S,5S)-5-fluoropiperidin-3-yl)pyrimidine-5-carboxamide;

2-(5-((3-ethoxypyridin-2-yl)oxy)pyridin-3-yl)-N-((3R,4S)-4-fluoropiperidin-3-yl)pyrimidine-5-carboxamide;

2-(5-((3-ethoxypyridin-2-yl)oxy)pyridin-3-yl)-N-((3R,4R)-4-fluoropiperidin-3-yl)pyrimidine-5-carboxamide;

2-(5-((3-ethoxy-5-fluoropyridin-2-yl)oxy)pyridin-3-yl)-N-((3R,4R)-4-fluoropiperidin-3-yl)pyrimidine-5-carboxamide; and 2-(5-((3-ethoxypyridin-2-yl)oxy)pyridin-3-yl)-N-((3S,5S)-5-fluoropiperidin-3-yl)pyrimidine-5-carboxamide, or a pharmaceutically acceptable salt of said compound;

a second compound, said second compound being an anti-diabetic agent; a non-alcoholic steatohepatitis treatment agent, a non-alcoholic fatty liver disease treatment agent, a cholesterol or lipid lowering agent, or an anti-heart failure treatment agent and a pharmaceutical carrier, vehicle or diluent.

11. The pharmaceutical combination composition as recited in claim 10 wherein said non-alcoholic steatohepatitis treatment agent or non-alcoholic fatty liver disease treatment agent is an ACC inhibitor, a KHK inhibitor, a BCKDK inhibitor, an FXR agonist, metformin, an incretin analog, or a GLP-1 receptor agonist.

12. The pharmaceutical combination composition as recited in claim 10 wherein said non-alcoholic steatohepatitis treatment agent or non-alcoholic fatty liver disease treatment agent is 4-(4-(1-isopropyl-7-oxo-1,4,6,7-tetrahydrospiro[indazole-5,4'-piperidine]-t-carbonyl)-6-methoxypyridin-2-yl)benzoic acid; [(1R,5S,6R)-3-{2-[(2S)-2-methylazetidin-1-yl]-6-(trifluoromethyl)pyrimidin-4-yl}-3-azabicyclo[3.1.0]hex-6-yl]acetic acid; 2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid; 2-((4-((S)-2-(5-chloropyridin-2-yl)-2-methylbenzo[d][1,3]dioxol-4-yl)piperidin-1-yl)methyl)-1-(((S)-oxetan-2-yl)methyl)-1H-benzo[d]imidazole-6-carboxylic acid; or 2-[(4-{6-[(4-cyano-2-fluorobenzyl)oxy]pyridin-2-yl}piperidin-1-yl)methyl]-1-[(2S)-oxetan-2-ylmethyl]-1H-benzimidazole-6-carboxylic acid or a pharmaceutically acceptable salt thereof.

13. The pharmaceutical combination composition as recited in claim 10 wherein said anti-diabetic agent is an SGLT-2 inhibitor, a BCKDK inhibitor, metformin, an incretin analog, an incretin receptor modulator, a DPP-4 inhibitor, or a PPAR agonist.

14. The pharmaceutical combination composition as recited in claim 13 wherein said anti-diabetic agent is metformin, sitagliptin, ertuglifozin, 2-[(4-{6-[(4-cyano-2-fluorobenzyl)oxy]pyridin-2-yl}piperidin-1-yl)methyl]-1-[(2S)-oxetan-2-ylmethyl]-1H-benzimidazole-6-carboxylic acid or 2-((4-((S)-2-(5-chloropyridin-2-yl)-2-methylbenzo[d][1,3]dioxol-4-yl)piperidin-1-yl)methyl)-1-(((S)-oxetan-2-yl)methyl)-1H-benzo[d]imidazole-6-carboxylic acid.

15. The pharmaceutical combination composition as recited in claim 10 wherein said anti-heart failure agent or cholesterol or lipid lowering agent is an ACE inhibitor, an angiotensin receptor blocker, a BCKDK inhibitor, an angiotensin receptor blocker—neprilysin inhibitor, a beta adrenergic receptor blocker, a calcium channel blocker, a fibrate, an HMG CoA reductase inhibitor or a vasodilator.

16. The method as recited in claim 5 wherein the compound is 2-(5-((3-ethoxypyridin-2-yl)oxy)pyridin-3-yl)-N-((3S,5S)-5-fluoropiperidin-3-yl)pyrimidine-5-carboxamide or a pharmaceutically acceptable salt thereof.

17. The method as recited in claim 6 wherein the compound is 2-(5-((3-ethoxypyridin-2-yl)oxy)pyridin-3-yl)-N-((3S,5S)-5-fluoropiperidin-3-yl)pyrimidine-5-carboxamide or a pharmaceutically acceptable salt thereof.

* * * * *